(12) United States Patent
Chalmers et al.

(10) Patent No.: US 7,151,609 B2
(45) Date of Patent: Dec. 19, 2006

(54) DETERMINING WAFER ORIENTATION IN SPECTRAL IMAGING

(75) Inventors: Scott A. Chalmers, San Diego, CA (US); Randall S. Geels, San Diego, CA (US)

(73) Assignee: Filmetrics, Inc., San Diego, CA (US)

( * ) Notice: Subject to any disclaimer, the term of this patent is extended or adjusted under 35 U.S.C. 154(b) by 0 days.

(21) Appl. No.: 11/327,222

(22) Filed: Jan. 7, 2006

(65) Prior Publication Data
US 2006/0164657 A1   Jul. 27, 2006

Related U.S. Application Data

(63) Continuation-in-part of application No. 09/899,383, filed on Jul. 3, 2001, now Pat. No. 7,095,511, which is a continuation-in-part of application No. 09/611,219, filed on Jul. 6, 2000, now abandoned.

(60) Provisional application No. 60/642,202, filed on Jan. 7, 2005.

(51) Int. Cl.
*G01B 11/28* (2006.01)

(52) U.S. Cl. .................................... 356/630; 356/326
(58) Field of Classification Search ........ 356/630–632, 356/364–369, 326, 614; 382/145
See application file for complete search history.

(56) References Cited

U.S. PATENT DOCUMENTS

| 5,333,049 | A | * | 7/1994 | Ledger ..................... 356/504 |
| 5,543,919 | A | * | 8/1996 | Mumola .................... 356/632 |
| 5,659,172 | A | * | 8/1997 | Wagner et al. ............. 250/307 |
| 5,787,190 | A | * | 7/1998 | Peng et al. ................. 382/145 |
| 5,856,871 | A | * | 1/1999 | Cabib et al. ............... 356/503 |

* cited by examiner

*Primary Examiner*—Hoa Q. Pham
(74) *Attorney, Agent, or Firm*—Courtney Staniford & Gregory LLP

(57) ABSTRACT

Devices and methods for determining wafer orientation in spectral imaging are described. The devices and methods generate an image of a wafer that includes at least one spectral dimension. One or more properties are determined from the spectral dimension, and a map is generated based on the property. The generated map is compared to at least one other map, and data or information of the comparison is used to locate a region of the wafer, for example a measurement pad or other structure.

37 Claims, 42 Drawing Sheets

DETERMINING WAFER ORIENTATION IN SPECTRAL IMAGING

RELATED APPLICATIONS

This application is a continuation-in-part of U.S. patent application Ser. No. 09/899,383, filed Jul. 3, 2001 now U.S. Pat. No. 7,095,511, which is a continuation-in-part of U.S. patent application Ser. No. 09/611,219, filed Jul. 6, 2000 now abandoned.

This application claims the benefit of U.S. Patent Application No. 60/642,202, filed Jan. 7, 2005.

This application is related to U.S. patent application Ser. No. 11/056,350, filed Feb. 10, 2005, and U.S. patent application Ser. No. 11/065,182, filed Feb. 23, 2005.

FIELD

This invention relates generally to the field of semiconductor film metrology, and, more specifically, to the field of film measurement during semiconductor wafer fabrication and processing, for pattern recognition, and for determining film thickness and goodness-of-fit.

BACKGROUND

Many industrial processes require precise control of film thickness. In semiconductor processing, for example, a semiconductor wafer is fabricated in which one or more layers of material from the group comprising metals, metal oxides, insulators, silicon dioxide ($SiO_2$), silicon nitride (SiN), polysilicon or the like, are stacked on top of one another over a substrate, made of a material such as silicon. Often, these layers are added through a process known as chemical vapor deposition (CVD), or removed by etching or removed by polishing through a process known as chemical mechanical polishing (CMP). The level of precision required can range from 0.0001 µm (less than an atom thick) to 0.1 µm (hundreds of atoms thick).

To determine the accuracy of these processes after they occur, or to determine the amount of material to be added or removed by each process, it is advantageous to measure the thickness of the layers on each product wafer (i.e., on each wafer produced that contains partially processed or fully processed and saleable product), which is generally patterned with features on the order of 0.1 µm to 10 µm wide. Because the areas covered by these features are generally unsuitable for measurement of film properties, specific measurement sites called "pads" are provided at various locations on the wafer. To minimize the area on the wafer that is taken up by these measurement pads, they are made to be very small, usually about 100 µm by 100 µm square. This small pad size presents a challenge for the film measurement equipment, both in measurement spot size and in locating the measurement pads on the large patterned wafer. A measurement spot size of an optical system refers to the size of a portion of an object being measured that is imaged onto a single pixel of an imaging detector positioned in an image plane of the optical system.

To date, though its desirable effects on product yield and throughput are widely recognized, thickness measurements are only made after certain critical process steps, and then generally only on a small percentage of wafers. This is because current systems that measure thickness on patterned wafers are slow, complex, expensive, and require substantial space in the semiconductor fabrication cleanroom.

Spectral reflectance is the most widely used technique for measuring thin-film thickness on both patterned and unpatterned semiconductor wafers. Conventional systems for measuring thickness on patterned wafers employ high-magnification microscope optics along with pattern recognition software and mechanical translation equipment to find and measure the spectral reflectance at predetermined measurement pad locations. Examples of this type of system are those manufactured by Nanometrics, Inc., and KLA-Tencor. Such systems are too slow to be used concurrently with semiconductor processing, so the rate of semiconductor processing must be slowed down to permit film monitoring. The result is a reduced throughput of semiconductor processing and hence higher cost.

A newer method for measuring thickness of patterned films is described in U.S. Pat. No. 5,436,725. This method uses a CCD camera to image the spectral reflectance of a full patterned wafer by sequentially illuminating the wafer with different wavelengths of monochromatic light. Because the resolution and speed of available CCD imagers are limited, higher magnification sub-images of the wafer are required to resolve the measurement pads. These additional sub-images require more time to acquire and also require complex moving lens systems and mechanical translation equipment. The result is a questionable advantage in speed and performance over traditional microscope/pattern recognition-based spectral reflectance systems.

Ellipsometry is another well-known technique for measuring thin film thickness. This technique involves measuring the reflectance of p-polarized and s-polarized light incident on a sample. Systems exploiting this technique include a light source, a first polarizer to establish the polarization of light, a sample to be tested, a second polarizer (often referred to as an analyzer) that analyzes the polarization of light reflected from the sample, and a detector to record the analyzed light. Companies such as J. A. Woolam, Inc. (Lincoln, Nebr.) and Rudolph Technologies, Inc. (Flanders, N.J.) manufacture ellipsometer systems.

Taking reflectance measurements from measurement pads on semiconductor wafers requires that the measurement pads first be located relative to the measurement apparatus. In traditional microscope-based systems this is usually done by using a video imaging device such as a CCD camera in conjunction with pattern recognition software, which compares the wafer image to a known (learned) image, to determine the wafer orientation. Once the wafer orientation is determined, the microscope objective can then be moved relative to the wafer so that it is positioned above the measurement pad and then the reflectance data taken. With spectral imaging techniques, the problem is similar, except that the imaging device and the reflectance measurement apparatus are the same, and the reflectance spectra are taken from the image in software after the pattern recognition step has determined the wafer orientation.

A problem in employing the methods described above is that images taken of nominally identical patterns on a wafer can vary greatly depending upon the film thicknesses present. The variations may arise either because the images are taken from different areas on the same wafer that have different film thicknesses, or because they are taken from different times in the process sequence, which results in different film stacks and/or film thicknesses. For example, fabrication systems that employ processing steps such as chemical mechanical polishing (CMP) can cause contrast variations to occur in images taken at the same location but at different times. In another example, shown in FIG. 39 herein, two images are taken from the same wafer, but in different locations that have different film thicknesses. In these images, the measurement pads appear as a column of square boxes in the center. A noticeable contrast variation occurs between similar areas on the two images. When the image contrast of the wafer changes such that shapes and edges invert or disappear, the software can no longer reliably determine wafer orientation. Thus, pattern recognition software that relies on edge and/or shape detection can be ineffective or unreliable during wafer processing.

INCORPORATION BY REFERENCE

Each publication, patent and/or patent application mentioned in this specification is herein incorporated by reference in its entirety to the same extent as if each individual publication, patent and/or patent application was specifically and individually indicated to be incorporated by reference.

BRIEF DESCRIPTION OF THE DRAWINGS

The components in the figures are not necessarily to scale, emphasis instead being placed upon illustrating the principles of the embodiments. In the figures, like reference numerals designate corresponding parts throughout the different views.

DETAILED DESCRIPTION

Figure 1:
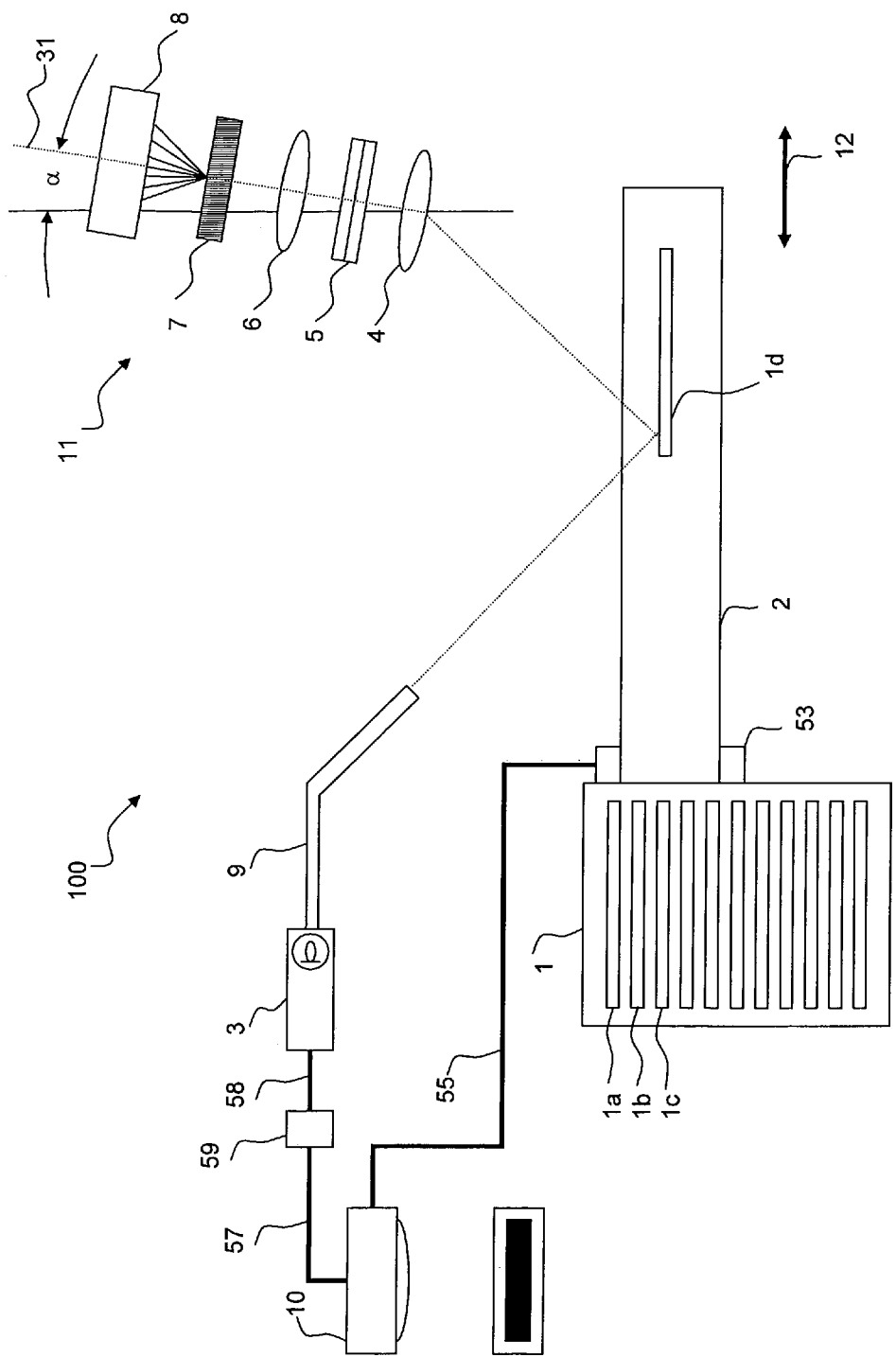
FIG. 1 illustrates a first embodiment of a system in accordance with the subject invention.

Devices and methods for determining wafer orientation in spectral imaging are described herein. The devices and methods of an embodiment, collectively referred to herein as imaging, provide a spectrometer configured to simultaneously capture a reflectance spectrum for each of a plurality of spatial locations on the surface of a sample. The spectrometer includes a wavelength-dispersive element, such as a prism or diffraction grating, for receiving light representative of the plurality of spatial locations, and separating the light for each such location into its constituent wavelength components. The spectrometer further includes an imager for receiving the constituent wavelength components for each of the locations, and determining therefrom the reflectance spectrum for each location.

The devices and methods of an embodiment also provide a system for measuring one or more properties of a layer of a sample. The system includes a light source for directing light to the surface of the layer at an angle that deviates from the layer normal by a small amount. Also included is a sensor for receiving light reflected from and representative of a plurality of spatial locations on the surface of the layer, and simultaneously determining therefrom reflectance spectra for each of the plurality of spatial locations on the surface. The system also includes a processor for receiving at least a portion of the data representative of the reflectance spectra for each of the plurality of spatial locations and determining therefrom one or more properties of the layer.

The devices and methods of an embodiment further include one or more polarizers to provide for measuring the reflectance spectrum of polarized light. In this embodiment, broad spectral light passes through a first polarizer, reflects and mixes with light reflecting from one or more layers at a plurality of locations on the surface of a sample, and passes through a second polarizing element that allows the spectrometer to disperse and image the reflected light according to its polarization for each location.

The devices and methods of an embodiment also include a method for measuring one or more properties of a layer of a sample. The method includes directing light to a surface of the layer. It also includes receiving light at a small angle reflected from the surface of the layer, and determining reflectance spectra representative of each of a plurality of spatial locations on the surface of the layer. The sample may be relatively translated with respect to the directed and received light until reflectance spectra for all or a substantial portion of the layer has been determined. One or more properties of the layer may be determined from at least a portion of the reflectance spectra for all or a substantial portion of the layer.

The devices and methods of an embodiment include a system of and method for measuring at least one film on a sample from light reflected from the sample having a plurality of wavelength components, each having an intensity. A set of successive, spatially contiguous, one-spatial-dimension spectral reflectance images may be obtained by scanning the wafer with a one-spatial-dimension spectroscopic imager. The resulting series of one-spatial-dimension spectral images may be arranged to form a two-spatial-dimension spectral image of the wafer. The spectral data at one or more of the desired measurement locations may then be analyzed to determine a parameter such as film thickness.

The devices and methods of an embodiment further provide a system of and method for measuring at least one film on a sample from polarized light reflected from the sample having a plurality of wavelength components, each having an intensity. A set of successive, spatially contiguous, one-spatial-dimension spectral reflectance with s-polarized and/or p-polarized images may be obtained by scanning the wafer with a one-spatial-dimension spectroscopic imager. The resulting series of one-spatial-dimension spectral images may be arranged to form an s-polarized two-spatial-dimension spectral image (s-polarized image) of the wafer and a p-polarized two-spatial-dimension spectral image (p-polarized image) of the wafer, where the s-polarized image and the p-polarized image map in a one-to-one way each of the plurality of spatial locations on the sample. The s-polarized image and the p-polarized image data at one or more of the desired measurement locations may then be analyzed to determine a parameter such as film thickness.

In yet another embodiment, the devices and methods provide a system and method for determining wafer orientation from a spectral image. This embodiment uses any of the systems and/or methods described herein to obtain an image of a portion of a wafer surface, the image including a spectral dimension. During wafer processing, one or more film properties such as thickness are derived from the image. Using a processor, a new image is generated according to a derived film property, and then compared to previously generated criteria. Based on the comparison, a region of interest having specified characteristics is located by means of pattern recognition software. In one example, the region of interest is the location of a measurement pad or other measurement site. In another aspect, wafer orientation is determined in general.

The devices and methods of an embodiment provide a method and apparatus for achieving rapid measurement of film thickness and other properties on patterned wafers during, between, or after various semiconductor processing steps.

The devices and methods of an embodiment also include a spectral imaging method and apparatus for accurately determining measurement pad location and film properties, between, or after various semiconductor processing steps.

The devices and methods of an embodiment also include a method and apparatus for film measurement that is capable of providing an accurate measurement of film thickness and other properties of individual films in a multi-layered or patterned sample.

The devices and methods of an embodiment further include a method and apparatus for film measurement that is capable of providing an accurate measurement of film thickness and other properties of individual films in a multi-layered or patterned sample based on image analysis.

System for Measurements at an Angle

A first embodiment of an imaging system 100, suitable for use in applications such as measuring the thickness of transparent or semi-transparent films, is illustrated in FIG. 1. Advantageously, the film to be measured ranges in thickness from 0.001 µm to 50 µm, but it should be appreciated that this range is provided by way of example only, and not by way of limitation. This embodiment is advantageously configured for use with a wafer transfer station 1 to facilitate rapid measurement of a cassette of wafers. The station houses a plurality of individual wafers 1*a*, 1*b*, 1*c*, and is configured to place a selected one of these wafers, identified with numeral 1*d* in the figure, onto a platform 2. Each of wafers 1*a*, 1*b*, 1*c*, 1*d* has a center point and an edge. This embodiment also comprises a light source 3 coupled to an optical fiber 9 or fiber bundle for delivering light from the light source 3 to the wafer 1d situated on platform 2. Preferably, the light source 3 is a white light source. Advantageously, the light source 3 is a tungsten-halogen lamp or the like in which the output is regulated so that it is substantially invariant over time. For purposes of illustration, this embodiment is shown being used to measure the thickness of film on wafer 1d, which together comprises a sample, but it should be appreciated that this embodiment can advantageously be employed to measure the thickness of individual films in samples comprising multi-layer stacks of films, whether patterned or not. Light source 3 may optionally include a diffuser disposed between light source 3 and optical fiber 9 to even out light source non-uniformities so that light entering optical fiber 9 is uniform in intensity.

The first embodiment of imaging system 100 further includes a line imaging spectrometer 11 comprising a lens assembly 4, a slit 5 having a slit width, a lens assembly 6, a diffraction grating 7, and a two-dimensional imager 8. Line imaging spectrometer 11 has an optical axis 31, and is disposed in imaging system 100 so that optical axis 31 is aligned at a small angle $\alpha$ to the wafer 1d normal. Lens assembly 4 and lens assembly 6 each have a magnification.

Two-dimensional imager 8 has an integration time during which it absorbs light incident upon it to create a detected signal. This integration time is selectable over a broad range of values with preferred values being 10 to 1000 us.

Angle $\alpha$ defines near normal incidence, and can be as small as 0 degrees or as large as that given by the Brewster angle of the topmost layer, but preferably the angle $\alpha$ is approximately 2 degrees. A range of angles from 0 to Brewster angle allows one or more measurements at angle $\alpha$, which provides greater information. The angle $\alpha$ lies in a measurement plane that, if aligned with an array of conductive metal lines, results in improved measurements. Measurements obtained at such an angle are uniquely capable of determining the thickness of films in finely patterned areas with feature dimensions on the order of the wavelength of the light being used. This capability results from reduced interaction with the feature sidewalls than with angled (and thus high NA) reflectance measurements such as those provided by microscope optics or the apparatus described in U.S. Pat. No. 5,436,725. The small NA (0.01 to 0.05 is typical) and near normal incidence measurements provided by the apparatus of an embodiment are not as sensitive to (and therefore not thrown off by), for example, variations in metal line widths and sidewall angles when measuring oxide erosion caused by chemical-mechanical polishing. The small NA and near normal incidence measurements provided by the apparatus of an embodiment also result in a much greater depth-of-field than conventional patterned-wafer measurement systems have, which allows for measurements to be made without precision z-motion (height) mechanisms or point-to-point or wafer-to-wafer focus adjustments, as are necessary with other methods.

System 100 further includes a translation mechanism 53 that is mechanically connected to platform 2 and serves to move platform 2 holding wafer 1d. In accordance with commands from computer 10, translation mechanism 53 causes platform 2 to move.

Computer 10 is also electrically connected to a synchronization circuit 59 via an electrical connector 57. Synchronization circuit 59 in turn is electrically connected to light source 3. Upon command from computer 10 and propagated via electrical connection 57, synchronization circuit 59 sends one or more synchronization signals to light source 3 that cause light source 3 to emit one or more pulses of light. By coordinating motion of wafer 1d and the synchronization signals sent to synchronization circuit 59, minimally sized illumination spots are formed on wafer 1d.

In the absence of relative motion of wafer 1d, each of the one or more pulses of light forms a small spot on wafer 1d, where the size of each spot is determined largely by the specific design configuration of line imaging spectrometer 11 and the pixel dimensions of two-dimensional imager 8. The nominal size of each measurement spot is approximately 50 um. However, when wafer 1d is in motion and light from light source 3 is emitted continuously, each spot is elongated and the area from which light is detected increases.

A scan time is defined as the time necessary for system 100 to acquire data from the regions of interest of wafer 1d, i.e. by sequentially imaging areas across wafer 1d. A scan speed is the scan time divided by the length of the area being measured. For example, if entire wafer 1d is the scan area, and 5 seconds is the scan time, then the scan speed is 40 mm/s, assuming a 200 mm diameter wafer. Note that scan speed refers to the speed with which an area on wafer 1d is being imaged moves across wafer 1d; whether wafer 1d or light source 3 or line imaging spectrometer 11 moves does not matter.

With two-dimensional imager 8 having a 1 ms integration time in the example above, the measurement spot for each measurement sweeps across an additional portion of wafer 1d that extends for 40 um. This additional distance causes the detected reflectance spectrum to be a mixture of whatever film stacks the spot passed over during the integration time. However, by using short pulses of light, the additional distance is reduced. For example, a 10 us pulse width means that the additional distance less than 1 um, which is significantly less than the nominal spot size of 50 um.

Imaging system 100 operates as follows. Light from source 3 passes through fiber bundle 9, and impinges on a film contained on or in wafer 1d. The light reflects off the wafer and is received by lens assembly 4. Lens assembly 4 focuses the light on slit 5. Slit 5 receives the light and produces a line image of a corresponding line on the wafer 1d. The line image is arranged along a spatial dimension. The line image is received by second lens assembly 6 and passed through diffraction grating 7. Diffraction grating 7 receives the line image and dissects each subportion thereof into its constituent wavelength components, which are arranged along a spectral dimension. In one implementation, the spectral dimension is perpendicular to the spatial dimension. The result is a two-dimensional spectral line image that is captured by two-dimensional imager 8 during the integration time. In one implementation, the imager is a CCD, the spatial dimension is the horizontal dimension, and the spectral dimension is the vertical dimension. In this implementation, the spectral components at each horizontal CCD pixel location along the slit image are projected along the vertical dimension of the CCD array.

Figure 2:
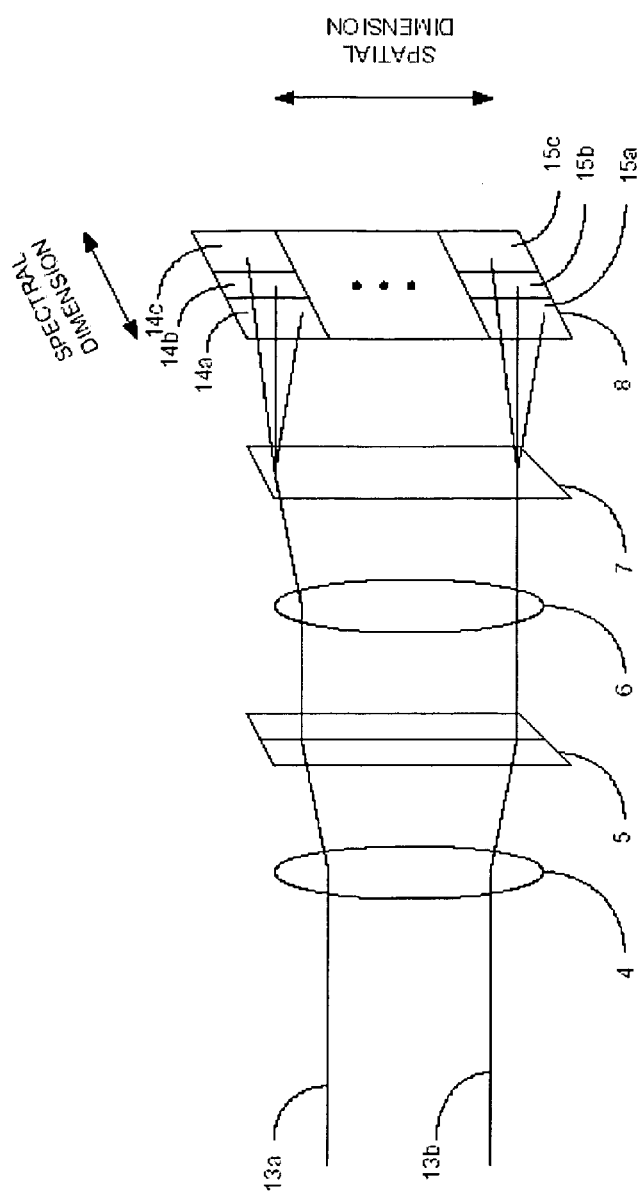
FIG. 2 illustrates in detail the optical subsystem of the embodiment shown in FIG. 1.

Additional detail regarding the spectrometer 11 is illustrated in FIG. 2 in which, compared to FIG. 1, like elements are referenced with like identifying numerals. As illustrated, reflected light (for purposes of illustration, two rays of reflected light, identified with numerals 13a and 13b are shown separately) from wafer 1d is received by lens assembly 4 and focused onto slit 5. Slit 5 forms a line image of the light in which the subportions of the line image are arranged along a spatial dimension. The line image is directed to lens assembly 6. Lens assembly 6 in turn directs the line image to diffraction grating 7. Diffraction grating 7 dissects each subportion of the line image into its constituent wavelength components. The wavelength components for a subportion of the line image are each arranged along a spectral dimension. Two-dimensional imager 8 individually captures the wavelength components for the subportions of the line image during the integration time. Thus, the wavelength components for ray 13*a* are individually captured by pixels 14*a*, 14*b*, and 14*c*, respectively. Similarly, the wavelength components for ray 13*b* are individually captured by pixels 15*a*, 15*b*, and 15*c*, respectively. Imager 8 is preferably designed so that the vast majority of photons landing upon individual pixels wind up storing electrical charge only within the pixels that they land on. For example, common CCD design allows photons with large penetration depths (i.e., photons with long wavelength) to generate electrons far beneath the pixels that they land on, and then allows these electrons to wander up and to be collected by pixels neighboring the pixel that the photons originally entered the CCD through. This causes a reduction in image resolution and an increase in the apparent measurement spot size, but can be substantially reduced by proper CCD design (by reducing the migration length of electrons below the pixels, for example.)

With reference to FIG. 1, the light source 3 and the platform 2 are moveable relative to one another. In addition, platform 2 and spectrometer 11 are moveable in relation to one another. In one implementation, the light source 3 and spectrometer 11 are stationary, and the platform is moveable in an X direction 12.

Since the apparatus of embodiments described herein is capable of obtaining a large number of measurements, prodigious quantities of data must be dealt with. One way to limit the extent of such large quantities of data is to move platform 2 in a non-linear fashion. For example, platform 2 can be instructed to execute a large translational step to one particular location, then move in small translational steps over a region of wafer 1*d* where measurements are desired, then make another large translational step to another region of wafer 1*d* where more measurements are desired, and so on.

In operation, computer 10 sends commands to translation stage 53 that cause wafer 1*d* on platform 2 on wafer station 1 to move. When wafer 1*d* is positioned in a desired location, computer 10 sends synchronization commands to synchronization circuit 59, which cause light source 3 to emit pulses of light that propagate fiber bundle 9 to wafer 1*d*. Computer 10 also sends configuration commands to two-dimensional imager 8 that include the integration time and a command to initiate data collection. The pulses of light emitted by light source 3 are short enough compared to the speed of wafer 1*d* that the light collected by one-spatial-dimension imaging spectrometer 11 comes from a minimally sized spot on wafer 1*d*. Furthermore, the pulses of light from light source 3 are synchronized with the integration time and the data acquisition command so that each pulse is emitted only during the integration time. One-spatial-dimension imaging spectrometer 11 in turn communicates the spectral and spatial information to the computer 10 over one or more signal lines or through a wireless interface. Spectral reflectance data is continually taken in this way while the wafer 1*d* is moved under the one-spatial-dimension imaging spectrometer by the platform 2 under the action of translation stage 53 and upon command from computer 10.

Once the entire area of interest has been scanned in this manner, the computer 10 uses the successively obtained one-dimensional spatial data to generate a two-spatial-dimension image. The plurality of spectral reflectance images comprises a "spectral image". This two-dimensional map or spectral image can be generated by assembling the measured signal intensity at a single wavelength at each location on the wafer into an image, while retaining the spatial relationship between image locations within each scan and from contiguous scan line to the next. This two-dimensional image can then be analyzed to find pixels that correspond to specific locations on the wafer, and then the spectral reflectance data that is associated with these pixels can be analyzed using suitable techniques to arrive at an accurate estimate of the thickness of the film. Typically, film thickness is determined by matching the measured spectrum to a theoretically or experimentally determined set of spectra for layers of different thicknesses.

In the foregoing embodiment, although a CCD-based one-spatial-dimension imaging spectrometer is illustrated and described as the means for determining the intensity of the reflected light as a function of wavelength, it should be appreciated that other means are possible for performing this function, and other types of one-spatial-dimension imaging spectrometers are possible than the type illustrated in the figure.

The foregoing embodiment is described with a preferred way of forming minimally sized spots on each wafer by synchronizing the emission of pulses of light with the integration time of two-dimensional imager 8 and with wafer motion. However, alternate approaches that compensate for the relative wafer-to-imager motion also achieve the same ends. One such alternative approach is to use an electrically actuated "wafer tracking" mirror disposed within system 100 between imaging system 11 and the wafer 1*d*. In this alternative approach, the electrically actuated mirror includes a piezoelectric element mechanically connected to one edge of the mirror while the center of the mirror is secured to form a hinge that allows rotational motion about the center axis of the mirror so that the focal distance between the imaging system 11 and the wafer 1*d* remains substantially the same. Upon applying an electrical signal to the piezoelectric element, the electrically actuated mirror then deflects the light between wafer 1*d* and the imaging system 11 such that the imaging system tracks the wafer motion during each integration period. Between integration periods, the mirror position is reset to begin tracking the proper wafer location for the following integration time. Similar "wafer tracking" capabilities may be realized by displacing other optical elements, such as the slit 5.

Although the foregoing embodiment is described in the context of semiconductor wafers, and is illustrated in combination with a wafer transfer station for performing this function, it should be appreciated that it is possible to employ this embodiment in other contexts and in combination with other processing apparatus. Other possible applications include providing thin film scratch resistant and/or antireflective optical coatings to automotive plastics, eyeglass lenses, and the like plastics packaging applications, and applications involving providing appropriate polyimide and resist thicknesses for flat panel display manufacturing. In fact, any application or industrial process in which film measurement is desired is possible for use with the subject embodiment.

Among the primary advantages of the foregoing embodiment is that it is particularly well suited for real-time applications. The reason is that data collection steps employing time-consuming angular or mechanical sweeps of optical components as found in the prior art are eliminated. For example, in the subject embodiment, the one-spatial-dimension imaging spectrometer directly provides digitized values of intensity of the incoming light as a function of wavelength without requiring mechanical sweeping steps or the like. Also, digital CCD-based line-scan cameras are available with sufficient numbers of pixels so that resolution of measurement pads is possible. In addition, the number of analytical and pattern recognition steps performed by the computer are limited to only a very few. This is because an image of the entire wafer is made, which eliminates complicated pattern recognition routines that are needed when only small areas of the wafers are viewed at any one time, as is the case with microscope-based instruments.

Measuring Transparent/Semi-Transparent Films

Figure 3:
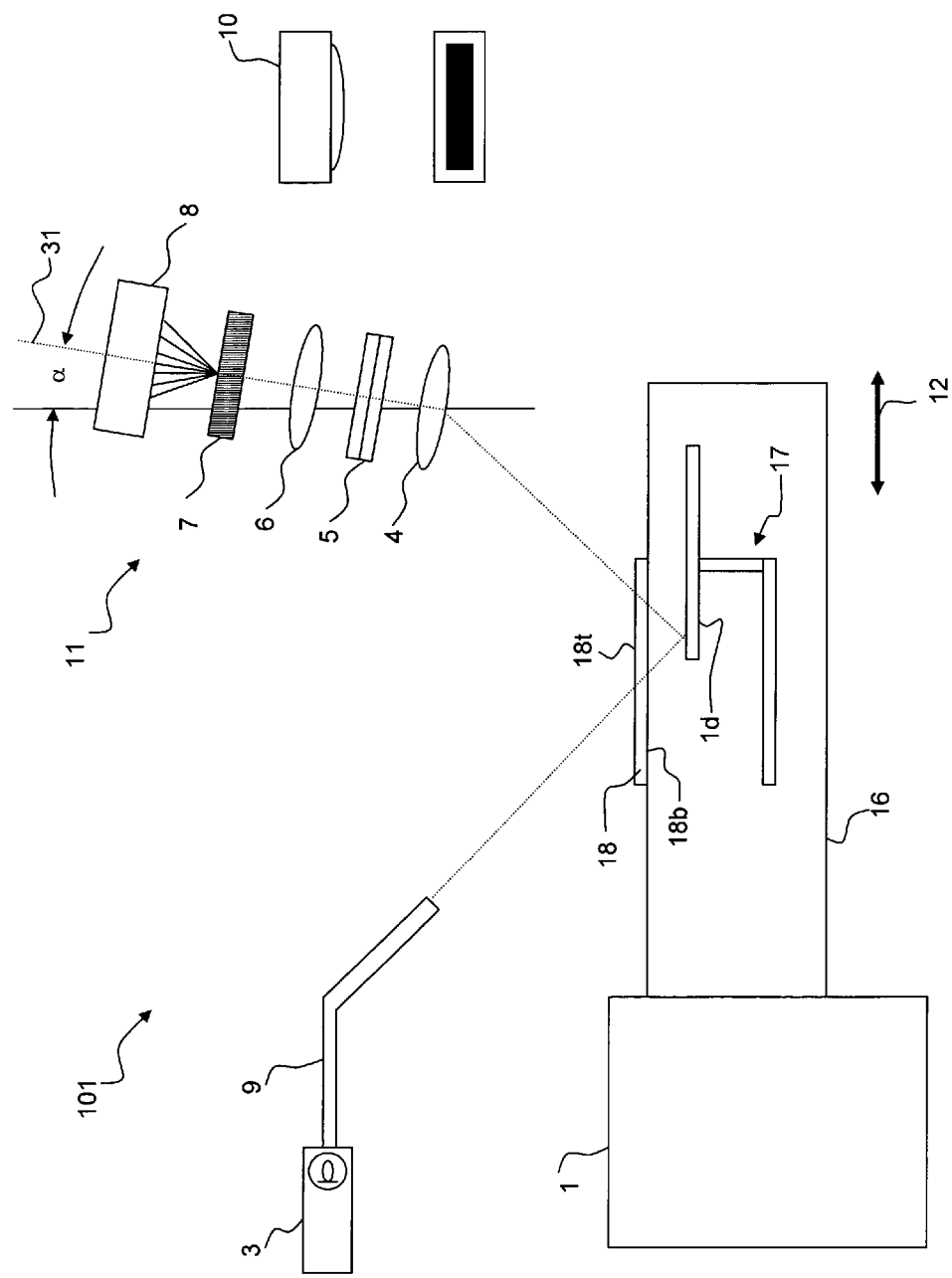
FIG. 3 illustrates a second embodiment of a system in accordance with the subject invention.

An embodiment for measuring transparent or semi-transparent films, such as dielectrics deposited upon patterned semiconductor wafers, is illustrated in FIG. 3 and designated as an imaging system 101 in which, compared to FIG. 1 and FIG. 2, like elements are referenced with like identifying numerals. This embodiment is similar to the previous embodiment, with the exception that the wafer 1d is in a vacuum process or transfer chamber 16, and the wafer motion required for scanning is provided by a transfer robotics assembly 17 that are used to move the wafer inside a vacuum chamber 16. Vacuum chamber 16 may be used for processing wafers, or for transferring wafers. Transfer robotics assembly 17 allows the wafer 1d to move in the X direction relative to light source 3 and spectrometer 11. Visual access to the wafer 1d is provided by a viewport 18. More specifically, light from light source 3 is directed to impinge upon wafer 1d via fiber bundle 9 through viewport 18. In addition, light reflected from wafer 1d is received by spectrometer 11 after passage through viewport 18. As transfer robotics assembly 17 moves the wafer 1d through the vacuum chamber 16 as part of the CVD process, spectral measurements are successively taken from successive portions of wafer 1d and provided to computer 10. Transfer robotics assembly 17 further serves to orient wafer 1d so that patterned features such as arrays of conductive lines are oriented to be co-planar with a plane defined by the wafer normal and the optical axis of spectrometer 11, which consequently enhances the precision with which film thickness measurements can be made. The plurality of spectral reflectance images of the patterned semiconductor wafer or portions of the wafer comprises a "spectral image". Computer 10 may successively perform calculations on the data as it is received or may do so after all or a substantial portion of the wafer 1d has been scanned. As with the previous embodiment, computer 10 may use this data to estimate film thickness.

In addition to the advantages listed for the first embodiment, this embodiment has the additional advantage of providing rapid in-line film thickness measurements taken during the normal transfer motion of the wafers between processes. This means that measurements can be made without slowing down the process and thus will not negatively affect throughput. Also, because the unit is compact and can be integrated into existing equipment, very little additional cleanroom space is required. Additionally, because there are no added moving parts, the system is very reliable. Moreover, because this embodiment is disposed entirely outside of vacuum chamber 16, it introduces no particles or contamination to the fabrication process.

Although the foregoing embodiment is described in the context of CVD processing of semiconductor wafers, and is illustrated in combination with a CVD station for performing this function, it should be appreciated that it is possible to employ this embodiment in other contexts and in combination with other processing apparatus. In fact, any application or industrial process in which in-line film measurement is desired, i.e., film measurement during an ongoing industrial process, is possible for use with the subject embodiment.

Forming a Line Image

Figure 4:
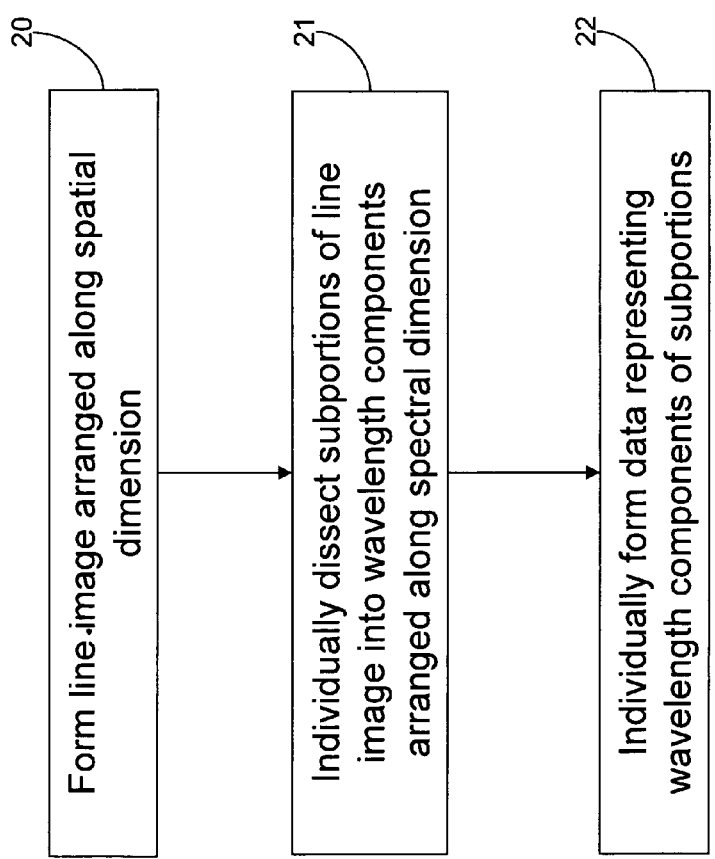
FIG. 4 illustrates an embodiment of a method in accordance with the subject invention.

An embodiment of a method is illustrated in FIG. 4. As illustrated, in step 20, a line image of a corresponding line of a film is formed. The line image has subportions arranged along a spatial dimension. Step 20 is followed by step 21, in which subportions of the line image are individually dissected to their relevant constituent wavelength components. The wavelength components for a subportion are arranged along a spectral dimension. Step 21 is followed by step 22, in which data representative of the wavelength components of the subportions is individually formed. The process may then be repeated for successive lines of the film until all or a selected portion of the film has been scanned. Throughout or at the conclusion of this process, estimates of film thickness or other film properties may be formed from the assembled data.

EXAMPLES

In an example embodiment, suitable for use in a CVD environment, the light source 3 is a tungsten/halogen regulated light source, manufactured by Stocker & Yale, Inc. (Salem, N.H.).

Fiber/fiber bundle 9 in this embodiment is a bundle configured into a line of fibers to provide uniform illumination along the measured surface. Several companies, Stocker & Yale being a prime example, manufacture such a fiber optic "line light".

This example is configured for use with CVD processing system Model P5000 manufactured by Applied Materials Inc., Santa Clara, Calif. An optically clear viewport 18 is provided in the standard P5000 configuration.

The line imaging spectrometer 11 in this example is manufactured by Filmetrics, Inc., San Diego, Calif., the assignee of the subject application. In this spectrometer, the imager 8 is a CCD imager incorporating a time delay and integration line scan camera manufactured by Dalsa Inc., Part No. CT-E4-2048 that has a CCD imager with 2048 pixels in the system spatial direction and 96 pixels in the system spectral direction. Optometrics (Ayer, Mass.) manufactures transmission diffraction grating 7 as Part No. 34-1211. The lenses 4 and 6 are standard lenses designed for use with 35 mm-format cameras. The line scan camera is custom-configured to operate in area-scan mode, with only the first 32 rows of pixels read out. This results in a data read rate greater than 1000 frames per second. Thirty-two rows of spectral data are sufficient for measurement of thicknesses in the range required for CVD deposited layers.

It has been found that this example embodiment yields a thickness accuracy of ±1 nm at a 1000 nm film thickness, at a rate of five seconds per wafer scan.

Commercial System

A commercial system is described below. The manufacturers of representative components of this system are as identified above, with the exception of the lens assembly used in the spectrometer. In lieu of standard lenses designed for use with 35 mm cameras, high quality lenses and mirrors manufactured by Optics 1 (Thousand Oaks, Calif.) are used. These lenses and mirrors are such that the modulation transfer function (MTF) for a plurality of alternating black and white line pair having a density of about 40 line pairs/mm. is greater than 70% over the entire wavelength range of interest.

This system is configured to measure the thicknesses of individual layers of a sample, e.g., patterned semiconductor wafer, at desired measurement locations. The coordinates of these desired measurement locations are provided to the system. Rather than rely on complicated and unreliable traditional pattern recognition techniques to find the exact measurement locations, the thickness of the wafer at each of these desired locations is determined by comparing the actual reflectance spectra for locations in a larger area containing the desired measurement location with a modeled reflectance spectra for the area assuming a particular layer thickness. If the comparison is within a desired tolerance, the assumed thickness is taken to be the actual thickness. If the comparison is not within the desired tolerance, the assumed thickness is varied, and the modeled reflectance spectra re-determined consistent with the newly assumed thickness. This process is continued until a comparison is performed which is within the desired tolerance. This process is repeated for a predetermined number, e.g. 5, of desired measurement locations on a layer of the wafer.

Figure 5:
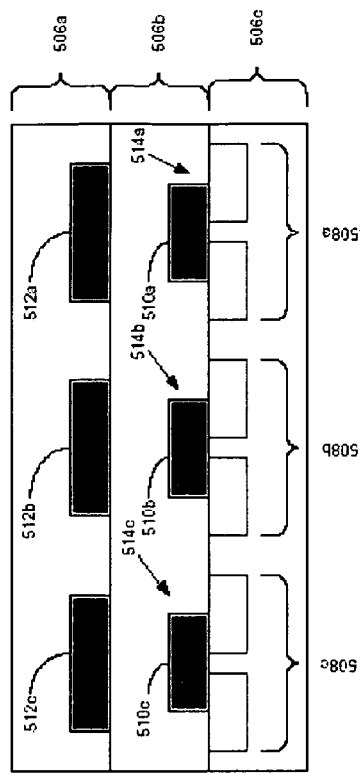
FIG. 5A is a top view of an example semiconductor wafer showing desired measurement locations.
FIG. 5B is a side view of an example semiconductor wafer showing stacked layers each configured with one or more precise features.
Figure 5:
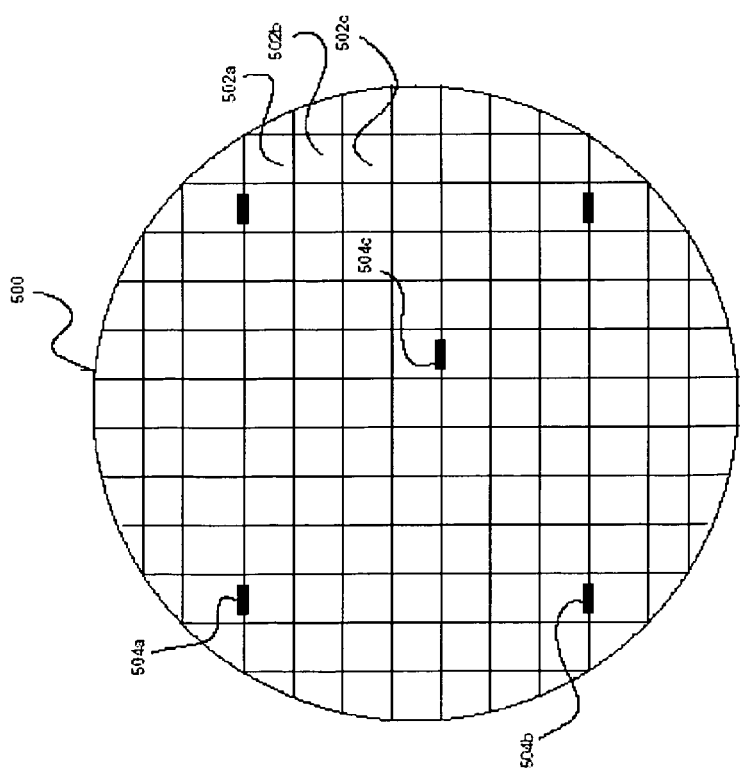

The situation can be further explained with reference to FIGS. 5A and 5B, which illustrate different views of an example 500 of a patterned semiconductor wafer. FIG. 5A illustrates a top view of the wafer 500. As shown, the wafer 500 may be divided up into individual dies 502a, 502b, and 502c. A plurality of predetermined measurement locations 504a, 504b, and 504c may also be provided. These measurement locations are typically situated in areas on the surface of wafer 500 that are between adjacent dies. The reason is these areas tend to have areas designed for use as measurement locations. This can be seen from an examination of FIG. 5B, which illustrates an example of a cross-section of one of the dies of FIG. 5A. As illustrated, in this example, the cross-section has three layers, identified from top to bottom respectively with identifying numerals 506a, 506b, and 506c. A combination of features provided in layers 506b and 506c form field-effect transistors 514a, 514b, and 514c. Layer 506c in this example provides doped regions 506a, 506b, 506c within a silicon substrate, where the doped regions 506a, 506b, 506c serve as the source/drain regions, respectively, of transistors 514a, 514b, and 514c. Layer 506b in this example comprises regions 510a, 510b, 510c which serve at the gates, respectively, of transistors 514a, 514b, and 514c. The topmost layer 506a provides metal contact regions 512a, 512b, 512c, which may be selectively connected to individual ones of gate regions 510a, 510b, 510c during the processing of the die.

This cross-section is built up layer by layer in the following order: 506c, 506b, and 506a. During or after the process of adding each of the layers, 506a, 506b, 506c, it may be desirable to measure the thickness of the layer at one or more points. However, it will be seen that each of the layers includes features that make it difficult to precisely model the reflectance spectra at those locations. For example, layer 506c has source/drain regions 508a, 508b, and 508c; layer 506b has gate regions 510a, 510b, 510c; and layer 506a has contact regions 512a, 512b, and 512c. These features compound the problem of modeling the reflectance spectra at these areas within the die. To simplify the modeling process, then, predetermined measurement locations are determined in areas where there are typically fewer features present, thereby simplifying the modeling process. In FIG. 5A, examples of these locations are the locations identified with numerals 504a, 504b, and 504c. Most often, open areas approximately 100 μm×100 μm are included in the wafer pattern design to serve as locations for film property measurements.

Figure 6:
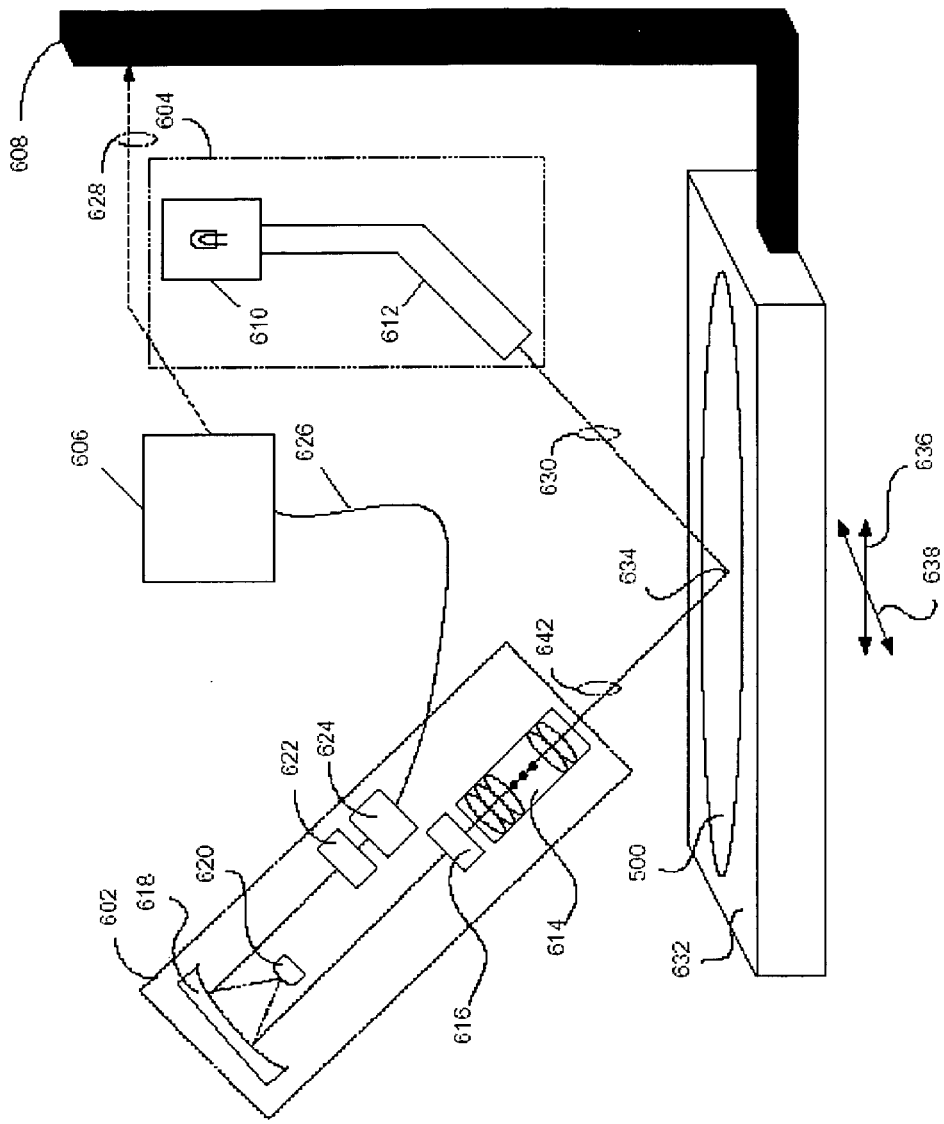
FIG. 6A illustrates a commercial embodiment of a system according to the invention.
FIG. 6B illustrates aspects of the optical path of the system of FIG. 6A.
Figure 6:
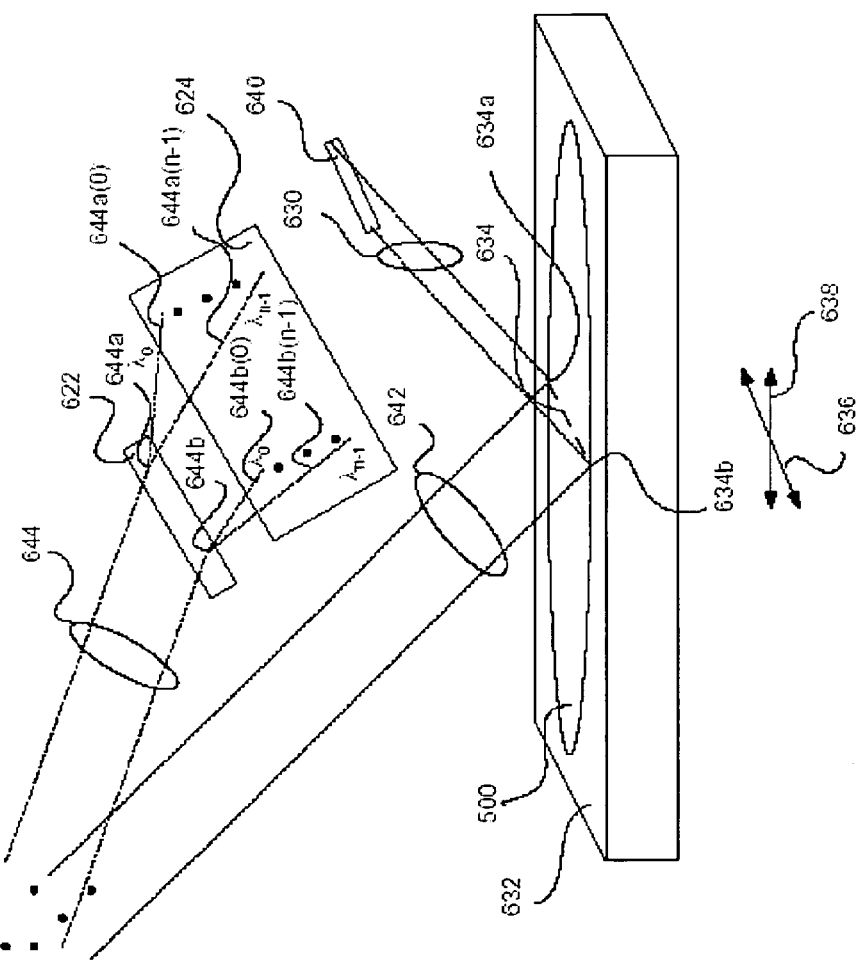

FIG. 6A illustrates an overall view of the commercial embodiment 600 of the system. A wafer 500 is supported on platform 632. A light source 604 directs light 630 to a plurality of locations 634 on the surface of the wafer 500, which, in the current commercial embodiment, is in the form of a line that spans the entire diameter of the wafer 500. It should be appreciated, however, that embodiments are possible where the plurality of locations 634 form an irregular or curved shape other than a line, or form a line which spans less than the full diameter of wafer 500.

Figure 7:
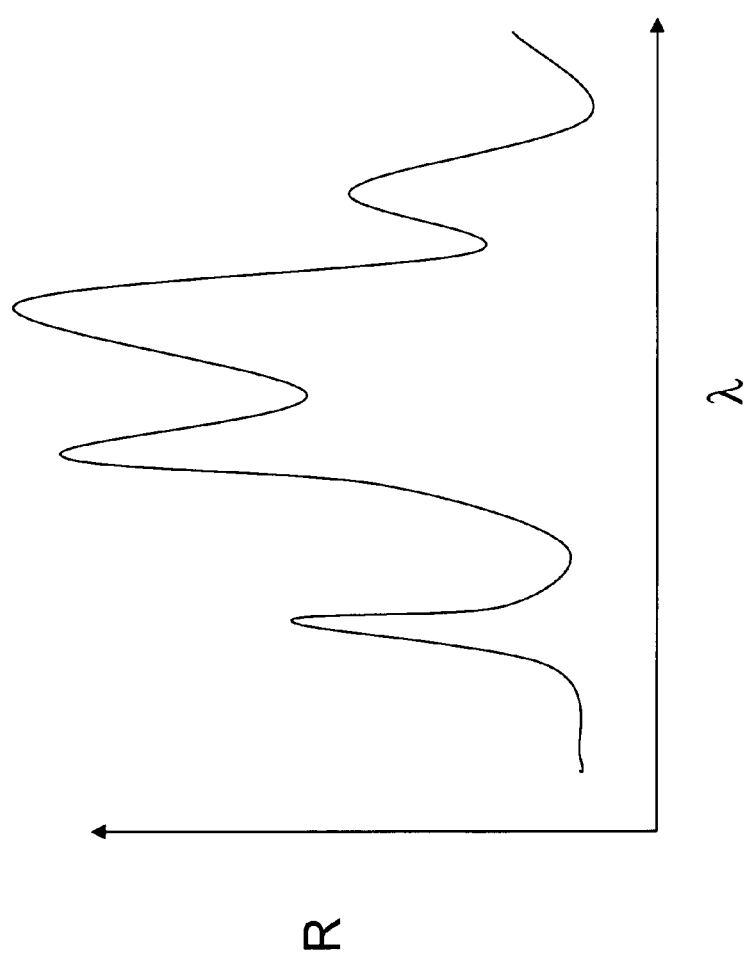
FIG. 7 illustrates an example of a reflectance spectrum for a location on the surface of a semiconductor wafer.

A sensor 602 receives the reflected light from the one or more locations 634, and determines therefrom the reflectance spectra representative of each of the one or more locations. The reflectance spectrum for a location is the spectrum of the intensity of the reflected light from the location as a function of wavelength, or some other wavelength-related parameter such as $1/\lambda$, $n/\lambda$, $nd/\lambda$, or nd (cos $\alpha)/\lambda$ where n is the index of refraction for the material making up the layer, $\lambda$ is wavelength, d is the thickness of the layer and $\alpha$ is the angle that the optical axis of spectrometer 11 makes with respect to the wafer normal. An example of the reflectance spectrum for a location on the surface of wafer 500 may be as illustrated in FIG. 7.

Once determined, the reflectance spectra for the plurality of locations 634 is provided to processor 606 over one or more signal lines 626, which may be implemented as a cable or other wired connection, or as a wireless connection or interface. This data may be provided to the processor concurrently with the capture of data from other locations on the surface of wafer 500. Alternatively, this transfer may be deferred until data for all or a substantial portion of the surface of wafer 500 has been captured.

Referring once again to FIG. 6A, a translation mechanism 608 is configured to relatively translate wafer 500 so that the incident light 630 can be scanned across the entirety of the surface of wafer 500. The translation mechanism 608 may be under the control of processor 606 or some other control means. Translation mechanism 608 has the further capability of orienting, under command of processor 606, wafer 500 so that the measurement plane is parallel with features such as parallel conductive lines in wafer 500 that may be present. In the current commercial embodiment, processor 606, as indicated by the phantom line 628, provides control of translation mechanism 608. Also, in the current commercial embodiment, where the incident light 630 impinges on the surface of wafer 500 in the form of a line that spans the full diameter of the wafer, the wafer 500 need only be moved in the X direction, identified with numeral 636, but it should be appreciated that embodiments are possible in which other directions of scanning, or combinations of directions, are possible. For example, in the case where the incident light impinges on the surface of wafer 500 in the form of a line which spans half of the full diameter of the wafer, the wafer 500 may be scanned in its entirety by scanning one half of the wafer in the X direction, then translating the wafer in the Y direction (identified with numeral 638) so that the remaining un-scanned portion of the wafer 500 resides under the incident light, and then scanning the second half of the wafer 500 by translating the wafer 500 in the X direction.

Figure 8:
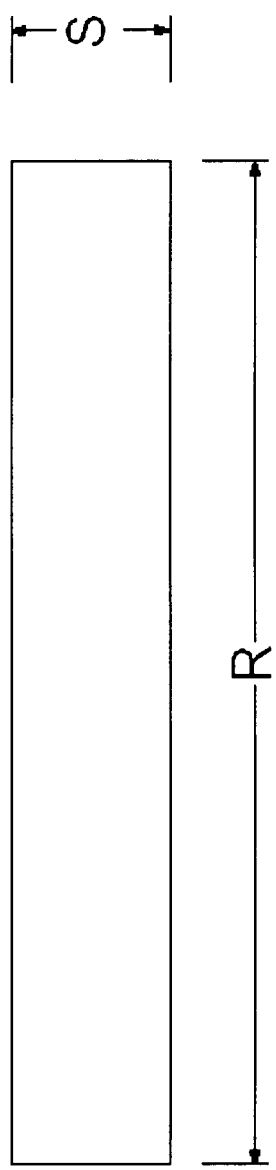
FIG. 8 illustrates a cross section of the fiber bundle of the system of FIG. 6A.

In the current commercial embodiment, where the plurality of locations 634 is in the form of a line which spans the full diameter of wafer 500, the light source 604 and sensor 602 are in a fixed relationship relative to one another, and the translation mechanism 608 is configured to achieve relative translation between the sensor 602 and the wafer 500 by successively moving the platform 632 supporting the wafer 500 relative to the light source 604 and sensor 602 in the X direction, identified with numeral 636. However, it should be appreciated that embodiments are possible in which light source 604 and sensor 602 are moveable relative to the wafer 500 by moving the light source 604 and sensor 602 relative to the platform 632. In the current commercial embodiment, the light source 604 comprises a white light source 610, or at least a light source having wavelength components over a desired wavelength range. In this commercial embodiment, light source 604 also includes a light shaper 612, which may be in the form of a fiber cable bundle where the individual fibers at the outer face 640 of the cable in aggregate form a rectangular shape as shown in FIG. 8. The rectangular shape of outer face 640 serves to project light from source 610 onto the surface of wafer 500 in the form of a line in the Y direction that spans the full diameter of the wafer, which in the case of this example is 100 mm. With reference to FIG. 8, the number of fibers currently employed in the long dimension, identified in the figure as R, is currently about 10,000 fibers, and S, the number of fibers in the short dimension, is currently about 10, but it should be appreciated that other dimensions and shapes are possible depending on the application. It should also be appreciated that embodiments are possible in which light shapers other than fiber cables are employed.

The sensor 602 in the current commercial embodiment includes a lens assembly 614 situated along the optical path traced by the reflected light 642 from the surface of wafer 500. This lens assembly 614 functions to reduce the size of the reflected light from about a 100 mm line to about a 26 mm line.

A slit 616, concave mirror 618, and convex mirror 620 are also included within sensor 602, and are also placed along the optical path traced by the reflected light 642. In the current commercial embodiment, these optical elements are placed after lens assembly 614 in the order shown in FIG. 6A. The slit 616 functions to aperture the light emerging from lens assembly 614 so that it is in the form of a line, and mirrors 618 and 620 function to direct the light so that it impinges upon transmission diffraction grating 622 which next appears along the optical path. As previously discussed, the entire lens/slit/mirror assembly is of sufficient quality that the MTF for an alternating black and white line pattern having a density of 40 line pairs/mm is not less than 70%.

It should be appreciated that lens assembly 614, slit 616, and mirrors 618 and 620 are not essential to the embodiments, and that embodiments are possible where these components are avoided entirely, or where other optical components are included to perform the same or similar functions.

In the current commercial embodiment, the light that impinges on diffraction grating 622 is located close to the CCD imager and is thus close to being focused back into the form of a line. The situation is as depicted in FIG. 6B in which, relative to FIG. 6A, like elements are identified with like reference numerals. As illustrated, incident light 630 from the outer face 640 of light shaper 612 is in the form of a line, and impinges upon wafer 500 in the form of a line 634 that spans the full diameter of the wafer 500 in the Y direction 638. The reflected light 642 is also in the shape of a line, and after various resizing and shaping steps, impinges upon diffraction grating 622. The line 644 is divisible into portions, each of which is representative of corresponding portions of wafer 500 along line 634. For example, portion 644a of the light impinging on diffraction grating 622 is representative of portion 634a of wafer 500, and portion 644b of the impinging light on diffraction grating 500 is representative of portion 634b of wafer 500.

Diffraction grating 622 breaks each of the individual portions of line 644 into their constituent wavelengths. Thus, with reference to FIG. 6B, grating 622 breaks portion 644a into n wavelength components, $\lambda_0, \ldots, \lambda_{n-1}$, identified respectively with numerals 644a(0), . . . , 644a(n-1), and also breaks portions 644b into n wavelength components $\lambda_0, \ldots, \lambda_{n-1}$, identified respectively with numerals 644b(0), . . . , 644b(n-1).

The wavelength components from each of the portions of line 644 impinge on imager 624, which measures the intensity of each of these wavelength components. Imager 624 then provides data representative of each of these intensities to processor 606.

In the current commercial embodiment, imager 624 has a resolution of 2048 pixels by 96 pixels, although in the current commercial embodiment, only 32 pixels in the vertical (spectral) dimension are used. In the spatial dimension, the sensor 602 is imaging about 100 mm of the wafer onto the 2048 pixels of the imager 624, which corresponds to approximately 50 µm of the wafer surface being imaged onto each pixel. The width of the slit 616 in the spectral dimension determines the measurement spot size in the direction perpendicular to the line image, and it was chosen so that the spot size is 50 µm in this dimension as well, so the resulting measurement spot size is approximately 50 µm×50 µm square over the entire 100 mm line being measured on the wafer. Additional commercial embodiments, such as the Filmetrics STMapper, measure larger wafers with the same sensors by simply mounting multiple sensors side-by-side to measure contiguous 100-mm-wide swathes of the wafers simultaneously. For example, the very common 200 mm diameter wafers are measured by mounting two sensors side-by-side, and the larger 300 mm diameter wafers are measured by mounting three sensors side-by-side.

Once the scanning of a layer has been completed, the processor 606 has access to the reflectance spectra for all or a substantial portion of the entire surface of wafer 500. This data can be depicted as shown in FIG. 9A. Numeral 900a identifies the reflectance data for points on wafer 500 for the first wavelength component, $\lambda_0$; numeral 900b identifies the reflectance data for the second wavelength component, $\lambda_1$, and numeral 900c identifies the reflectance data for the $(n-1)^{th}$ wavelength component, $\lambda_{n-1}$. Referring to FIG. 9B, reflectance data 900a in combination with off-wafer data points for the first wavelength component $\lambda_0$ comprises reflection data 910a. Reflectance data 900b in combination with off-wafer data points for the second wavelength component $\lambda_2$ comprises reflection data 910b. Likewise, reflectance data 900c in combination with off-wafer data points for the first wavelength component $\lambda_{n-1}$ comprises reflection data 910c. The ensemble of reflectance data 910 comprises a spectral image 920, shown in FIG. 9B.

In the current commercial embodiment, there are 32 wavelength components provided for each pixel location. The collection of these wavelength components constitutes the reflectance spectrum for the pixel location. Thus, with reference to FIG. 9A, the wavelength components identified with numerals 902a, 902b, and 902c collectively constitute the reflectance spectrum for a site on the surface of the wafer 500. Currently, about 1 Gbyte of data is generated for each layer, so the processor must include a storage device that is capable of storing this quantity of data.

Once the data for a layer has been captured, processor 606 is configured to analyze the data and determine therefrom the thickness of the layer at one or more desired measurement locations. In the current commercial embodiment, the coordinates of these measurement locations are known, and accessible to the processor 606. The processor 606 also has access to information that describes the structure of the wafer at the desired measurement locations sufficiently to allow the reflectance spectra at the desired locations, or the immediately surrounding areas, to be accurately modeled. Such information might include the composition of the layer in question and that of any layers below the layer in question, a description of any features, such as metal leads and the like, present in the layer in question and in any layers below the layer in question, and the thicknesses of any layers below the layer in question. For each of the desired measurement locations, the processor 606 is configured to use this information to model the reflectance spectrum of that location, or surrounding areas, assuming a thickness for the layer in question.

The processor 606 is further configured to compare the modeled spectrum for a desired measurement location, or surrounding locations, with the actual reflectance spectra for these locations, and if the modeled spectra is within a defined tolerance of the actual spectra, determine that the assumed layer thickness is the actual layer thickness. If the comparison is not within the defined tolerance for the measurement location in question, the processor 606 is configured to vary the assumed layer thickness, remodel the reflectance spectra using the assumed layer thickness, and then re-perform the comparison until the modeled data is within the prescribed tolerance. The processor 606 is configured to repeat this process for each of the desired measurement locations on a layer.

Figure 10:
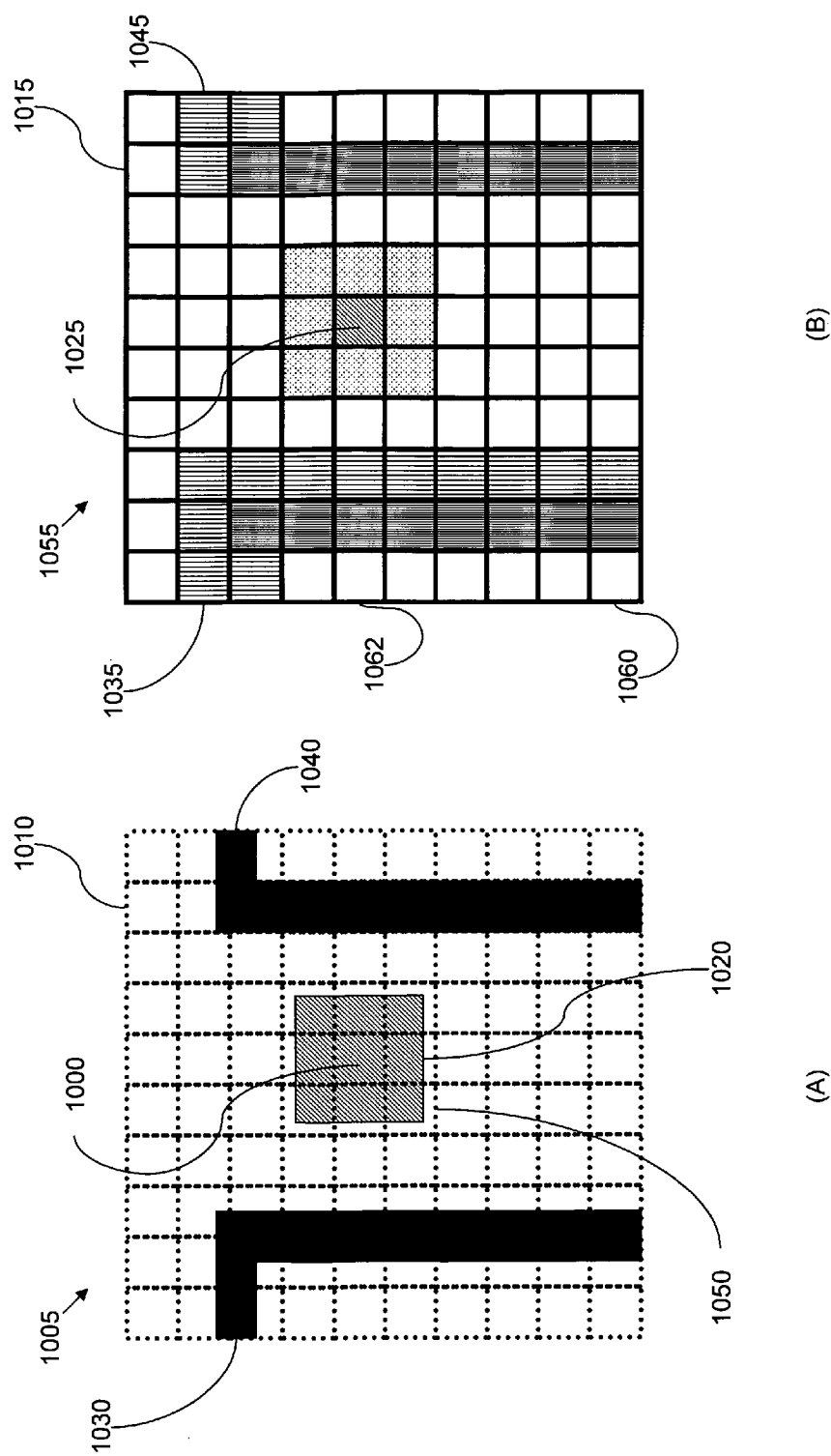
FIG. 10A illustrates the area surrounding a desired measurement location in which matching is performed in the system of FIG. 6A.
FIG. 10B illustrates the corresponding image of the desired measurement location in FIG. 10A.

In the current commercial embodiment, the processor 606 performs the comparison over a 10×10 pixel area centered on the nominal position of the desired measurement location. Analysis of more than one pixel is generally required because there is some uncertainty in the exact location of the desired measurement spot relative to the acquired wafer image, due to image imperfections caused by wafer vibration or other non-idealities. The situation is illustrated in FIG. 10, which illustrates the 10×10 pixel area surrounding the nominal desired measurement location 1000.

Figure 9:
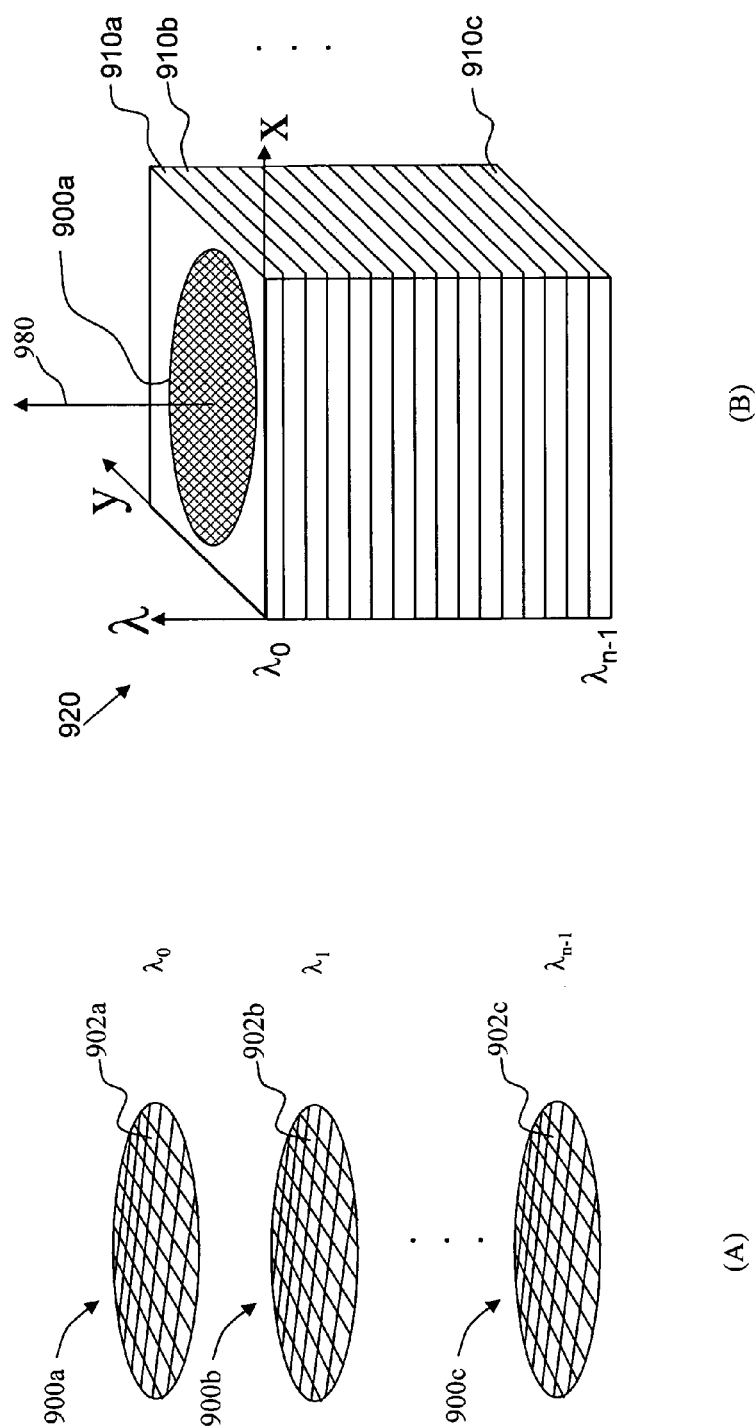
FIG. 9A depicts the one-spectral, two-spatial dimensional data that is captured for an individual layer in the system of FIG. 6A.
FIG. 9B shows the ensemble of one-spectral, two-spatial dimensional data that together forms a spectral image.

As an example, FIG. 10(A) shows a portion 1005 of wafer 500 with the outline of pixels superimposed on portion 1005. In particular and as an example, FIG. 10(A) shows bond pad 1020 between die edge 1030 and die edge 1040. In the center of bond pad 1020 is a desired measurement site 1000. Each pixel corresponds to a portion of wafer 500 from which the reflectance data 900 depicted in FIG. 9 are shown. Some pixels, such as pixel 1010, align with a uniform film stack, whereas other pixels, such as pixel 1050, cover more than one film stack (a portion of bond pad 1020 and the street between die edge 1030 and die edge 1040 in this case).

FIG. 10(B) shows an image of portion 1055 with the outline of pixels visible. The fill of each pixel represents the spectrum associated with each pixel; like fill indicates like spectra. Because of the small scale, there is some blurring in image of portion 1055. However, features are clearly delineated, and more importantly, there is at least one pixel corresponding exclusively to a bond pod 1020, namely pixel 1025.

The processor 606 is configured to compare the modeled spectrum with the measurement spectrum for each of these pixels, and to compute a running sum of the absolute value of the difference for each wavelength component for each of the spectra. Mathematically, this process can be represented as follows:

$$RSum = \sum_i ABS(\Delta_i) \qquad (1)$$

where the index i ranges over all possible wavelength components for a given pixel (currently 32), $\Delta_i$ is the difference between the modeled and actual intensities of the $i^{th}$ wavelength component for the pixel being analyzed, and ABS is the absolute value function. The comparison process for spectra of uniform film stacks such as pixel 1010 rapidly diverges, indicating a poor fit to the desired spectra. The comparison process for spectra of non-uniform film stacks such as pixel 1050 also rapidly diverges, indicating a poor fit to the desired spectra. For pixels over non-uniform film stacks such as pixel 1050, convergence to any spectra is difficult, but for pixels over uniform film stacks such as pixel 1010, convergence can be very rapid provided the comparison is done to the appropriate model spectra. In the case of pixel 1020, which is well aligned with bond pad 1020 and includes the nominal desired measurement location 1000, convergence to the model spectra is very rapid.

However, it should be appreciated that other methods of performing the comparison are possible and within the scope of the embodiments, such as methods in which less or more than a 10×10 area is involved, in which the comparison is performed over an area that is not necessarily centered on a desired measurement location, and in which functions other than the ABS function are employed. For example, in one alternative, the following statistic may be employed:

$$RSum = \sqrt{\sum_i \Delta_i^2} \qquad (2)$$

It is very useful to be able to automatically identify the locations of specific features such as bond pad images. With continuing reference to FIG. 10(B), pixels corresponding to like spectra can be used to identify high contrast regions such as those found at the edge of die. By looking for spectral signatures, one can identify key features such as bond pads. For example, an examination of a row 1060 leads to the signature of two high contrast regions with five pixels having the signature of streets in between. Likewise, an examination of a row 1062 leads to the signature of two high contrast regions with the signature of two pixels corresponding to streets sandwiched around three pixels corresponding to either bond pad material or a mixture of bond pad material and street material. In a similar fashion other structures can be identified.

Commercial Method

Figure 11:
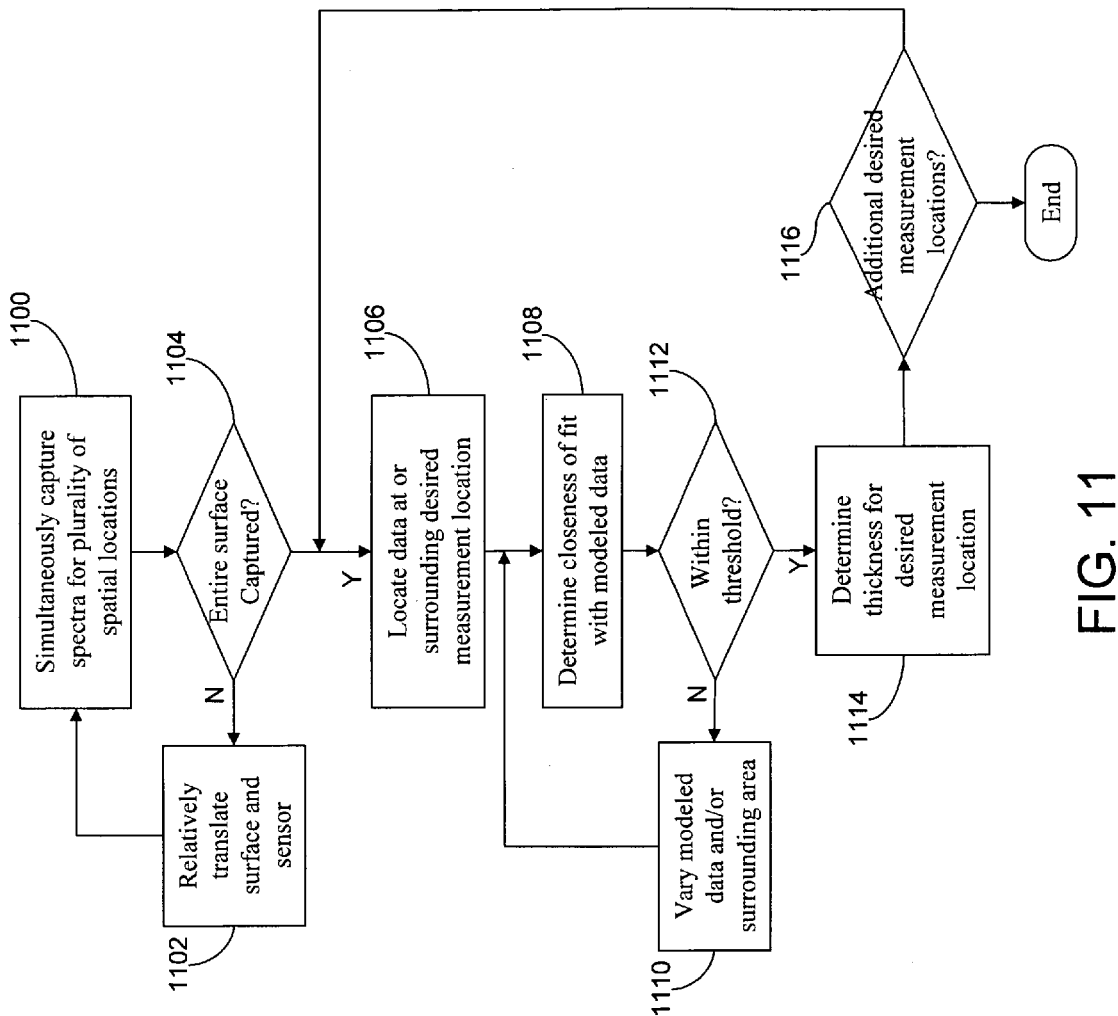
FIG. 11 is a flowchart of an embodiment of a method of operation in the system of FIG. 6A.

FIG. 11 is a flow diagram for a method of operation followed by a representative commercial embodiment for each layer in the sample being evaluated. The sample may be a semiconductor wafer or some other sample. In step 1100, the reflectance spectra for a plurality of spatial locations on the surface of a sample are simultaneously captured. The spatial locations may be in the form of a line, or some other shape, such as a curved shape, although in the current commercial embodiment, the locations are in the form of a line.

In step 1004, an evaluation is made whether all or a substantial portion of the entire surface has been scanned. If not, step 1102 is performed. In step 1102, a relative translation is performed between the surface of the sample and the light source and sensor used to perform the capture process. Again, this step can occur by moving the surface relative to one or the other of the light source and sensor, or vice-versa. Step 1100 is then re-performed, and this process repeated until all or a substantial portion of the entire surface of the layer has been scanned.

When all or a substantial portion of the entire surface of the layer has been scanned, step 1106 is performed. In step 1106, the coordinates of a desired measurement location are used to locate the reflectance data for that location or a location within a surrounding area. Step 1108 is then performed. In step 1108, the reflectance data for the location or a location within the surrounding area is compared with modeled reflectance data for that location to determine if the modeled data and actual data are within a prescribed tolerance. This modeled data is determined assuming a thickness for that layer at or near the desired measurement location.

The closeness of the fit is evaluated in step 1112. If the fit is outside a prescribed tolerance, step 1110 is performed. In step 1110, the reflectance data for the location is re-modeled assuming a different layer thickness and/or the location from which the actual data is taken is varied. Steps 1108 and 1112 are then re-performed. This process then continues until the modeled data is within the prescribed tolerance of the actual data. Step 1114 is then performed. In step 1114, the assumed layer thickness for the modeled data that satisfied the tolerance criteria in step 1112 is taken to be the actual layer thickness at the desired location.

Step 1116 is then performed. In step 1116, it is determined whether there are additional desired measurement locations for the layer in question. If so, a jump is made back to step 1106, and the process then repeats from that point on for the next location. If not, the process ends.

A variation on the method shown in the flowchart in FIG. 11 is insert a step prior to step 1100 that includes a rapid scan of all or part of the sample, and an analysis to assess whether the sensitivity of the detector has been set properly. This analysis involves comparing the intensity recorded by each pixel to the maximum possible, and if the maximum such intensity is within a pre-determined range that optimizes the measurements, then the logic of the method proceeds to step 1100; otherwise the sensitivity is adjusted to ensure that maximum intensity measurements obtained in step 1100 do fall within the pre-determined range at which point the logic of the method proceeds to step 1100.

Ellipsometric Measurements

With relatively minor modifications, the apparatus of an embodiment can be used to form wide-area high-speed, high-resolution ellipsometric images.

Figure 12:
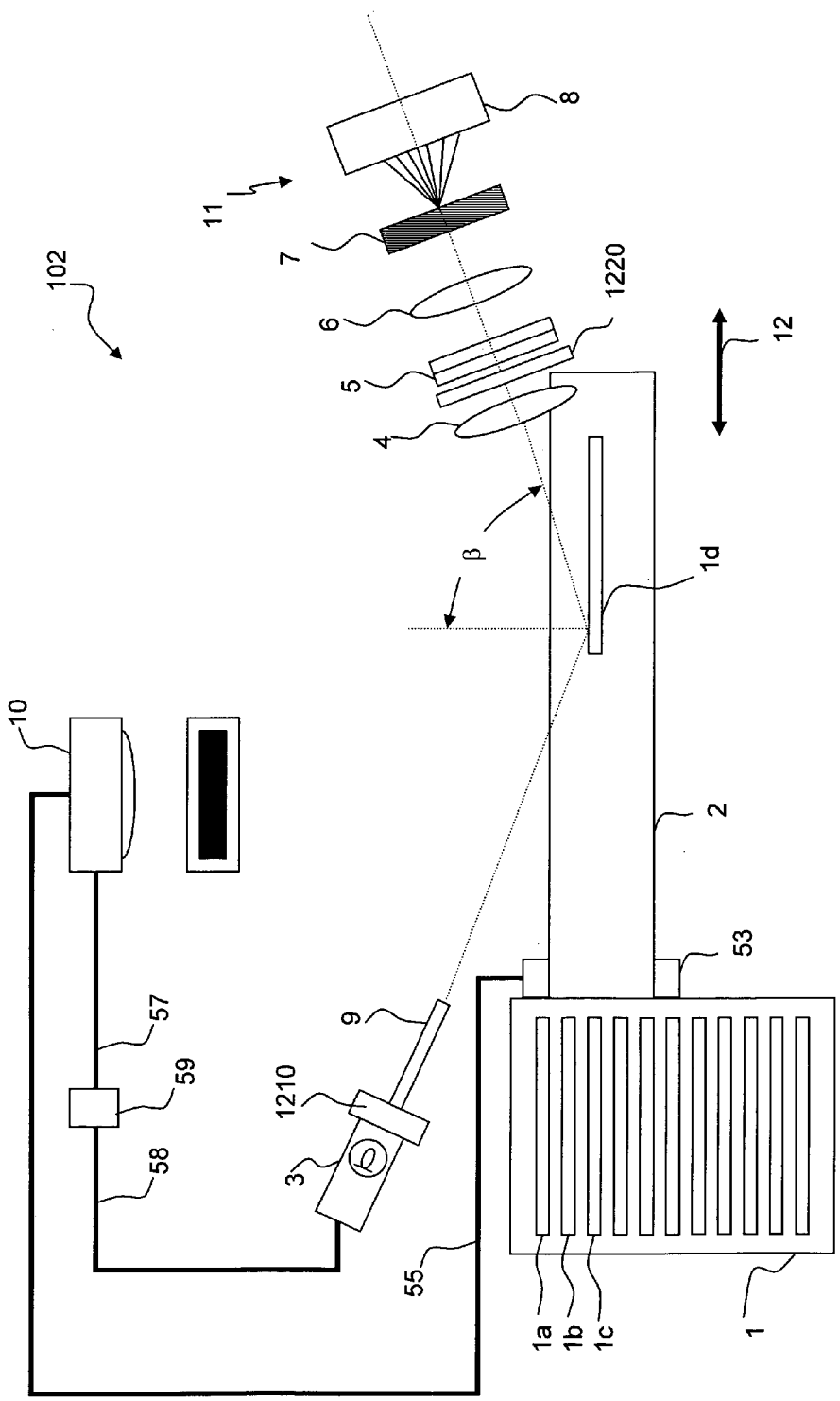
FIG. 12 illustrates an embodiment of a spectral ellipsometric system in accordance with the subject invention.

FIG. 12 shows system 102, which is identical to system 100 except for the addition of a polarizer 1210 and a rotating analyzer 1220 and software in computer 10 to control rotating polarizer 1220 and to analyze the data obtained with system 102. Polarizer 1210 is a linear polarizer having a polarization axis that defines the polarization angle of maximum transmission. Polarizer 1210 is disposed between light source 3 and optical fiber 9 and serves to ensure that light emitted from light source 3 impinges upon wafer 1d linearly polarized. Likewise, rotating analyzer 1220 has a polarization axis that defines the polarization angle of maximum transmission. Rotating analyzer 1220 further includes a rotation mechanism controllable by computer 10 such that the polarization angle of rotating analyzer 1220 is known.

System 102 operates to collect light reflected from wafer 1d identically to system 100 except for the effects of using polarized light and the algorithms used to infer film characteristics such as film thickness. Light impinging upon wafer 1d is polarized due to polarizer 1210 and the light reflecting from wafer 1d undergoes polarization shifts according the film properties on wafer 1d. Rotating analyzer 1220 transmits light reflected from wafer 1d in accordance with the polarization axis of rotating analyzer 1220. The light continues to propagate through line imaging spectrometer 11 to two-dimensional imager 8 where it forms a polarized line image. Since analyzer 1220 rotates, it alternately passes s-polarized and p-polarized light. By sequentially capturing s-polarized and p-polarized light, spatial maps of $\Psi$ and $\Delta$ can be generated from which, using well known methods, film properties such as thickness can be determined for each point and thus for all or portions of wafer 1d.

It is also important that data acquisition from two-dimensional imager 8 be synchronized with the velocity of wafer 1d so that alternating frames of data corresponding to s- and p-polarized light, can be aligned so that rows of s- and p-polarized data overlap. Previously discussed light strobing and/or wafer tracking methods can be used. Ellipsometric measurements can also be made using alternate configurations. If polarizer 1210 and analyzer 1220 are replaced with a rotating polarizer and a fixed analyzer respectively, then a rotating polarizer configuration is obtained. The operation of such a configuration is basically the same except that the polarization of the incident light is modulated before reflecting from the surface of wafer 1d and being analyzed by the fixed analyzer and recorded by two-dimensional imager 8.

Figure 21:
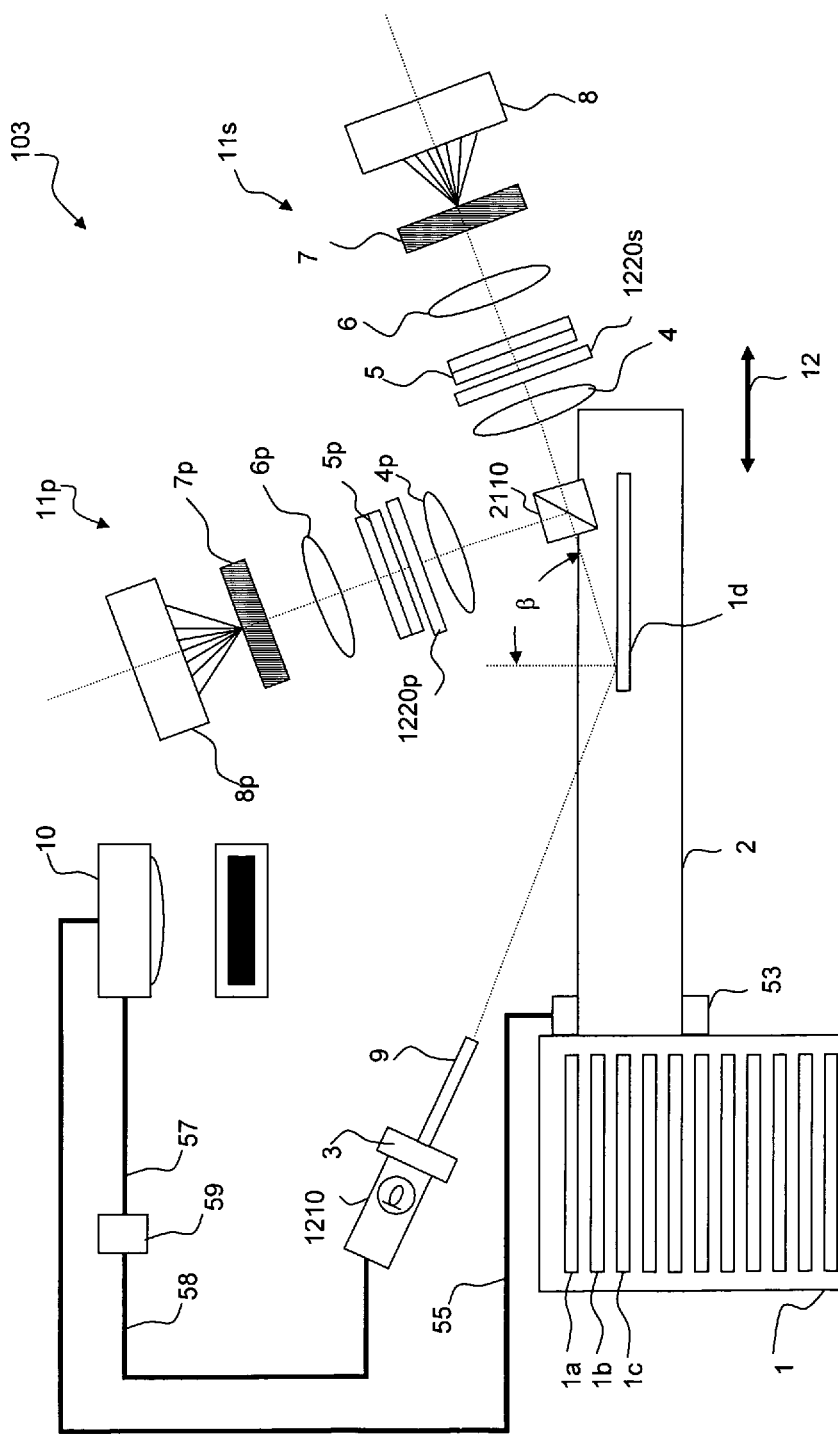
FIG. 21 illustrates a second embodiment of a spectral ellipsometric system in accordance with the subject invention.

The foregoing embodiment is described such that s- and p-polarized light is sensed in sequentially alternating frames. To avoid the need to carefully synchronize the timing of frame grabbing to ensure that sequential images of s- and p-polarized images overlap, a dual sensor arrangement can be used, as shown in FIG. 21 as imaging system 104. In this embodiment, light reflected from wafer 1d passes through a non-polarizing beamsplitter 2110 before being analyzed and detected.

Beamsplitter 2110 is disposed within system 102 so that light reflected by the beamsplitter remains in the plane defined by angle $\beta$. Light passing through the beamsplitter is analyzed by a line imaging spectrometer 11s for s-polarized light, where line imaging spectrometer 11s is identical to line imaging spectrometer 11 except that rotating analyzer 1220 is replaced by a fixed analyzer 1220s that is oriented to pass s-polarized light. Light reflected by beamsplitter 2110 is analyzed by a second line imaging spectrometer 11p for p-polarized light, where second line imaging spectrometer 11p is identical to line imaging spectrometer 11s except that it includes a fixed analyzer 1220p that is oriented to pass p-polarized light.

The other elements of second line imaging spectrometer 11p (enumerated in FIG. 21 with a suffix 'p') are duplicates of like identified elements of line imaging spectrometer 11s. With careful alignment, pulse synchronization, wafer tracking, and using software image reversal on images captured with second line imaging spectrometer 11p, images captured with the two line imaging spectrometers can be disposed within system 104 so that s-polarized and p-polarized measurements of the same locations on wafer 1d are substantially aligned.

Yet other ellipsometric measurement arrangements can also be accomplished using the basic structure of system 100 with suitable modifications. Such ellipsometric measurement arrangements are well known in the art and include a rotating compensator ellipsometer (which require a narrow spectrum light source for effective operation), a polarization modulation ellipsometer, and a null ellipsometer.

Figure 13:
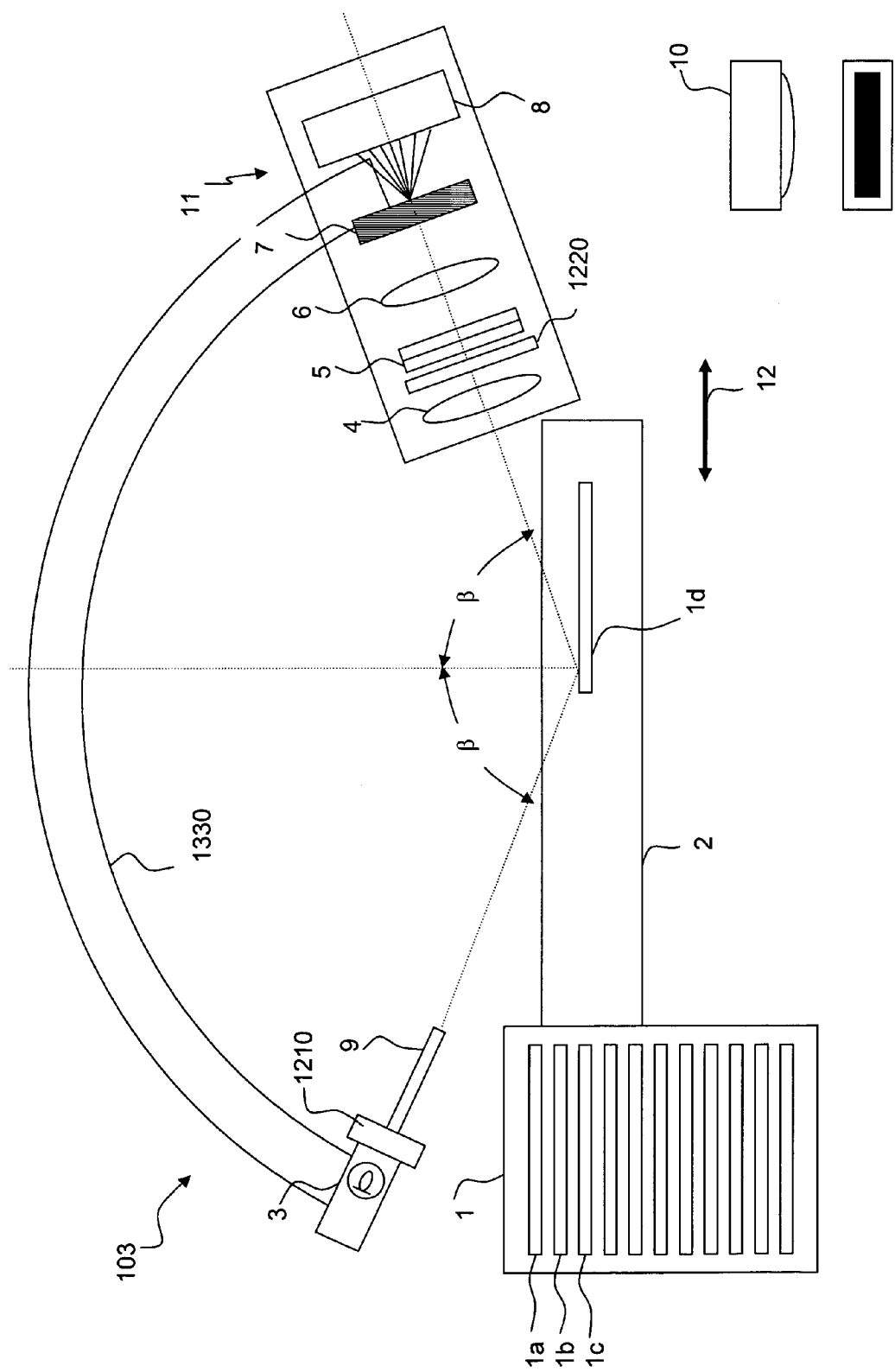
FIG. 13 illustrates an embodiment of a variable angle spectral ellipsometric system in accordance with the subject invention.

FIG. 13 shows a variable angle spectroscopic ellipsometer 103, which is yet another type of wide-area high-speed, high-resolution imaging ellipsometric imager that can be made. Ellipsometer 103 is identical to ellipsometer 102 except for the addition of angle track 1330. Ellipsometer 103 functions in the same way as ellipsometer 102 except that it allows $\Psi$ and $\Delta$ to be measured over a range of angles $\beta$. Preferably, ellipsometric images are obtained at a fixed angle $\beta$, then $\beta$ is adjusted to a different angle and another set of ellipsometric images are collected. This process continues over a range of angles that depends on the materials being measured. Since ellipsometric measurements are most sensitive when the incident light is incident at the Brewster angle, the ability to vary the angle $\beta$ adds additional capability, especially when measuring complicated film structures where each layer may have a different Brewster angle (that is a function of the index of refraction), and a given multi-layer film stack may have a pseudo-Brewster angle. Since this apparatus allows measurements to be made over a wide range of angles, and since such measurements are made across the entire wafer 1$d$, wide-area high-speed, high-resolution images are obtained over a very wide area, with higher speed and with improved resolution than is possible with the prior art.

Erosion Measurements

The apparatus of an embodiment can also be used to rapidly perform measurements to determine erosion, which occurs during CMP. Erosion is the excess removal of material in an array of metal lines or vias, and involves the removal of both metal and dielectric material though in unequal proportions. If too much metal is removed, then the integrated circuit so formed is subject to numerous performance issues ranging from degraded performance due to increased capacitance affecting RC-time constants to joule-heating failures arising from excessive reduction of the cross sectional area of metal lines (Bret W. Adams, et al., "Full-Wafer Endpoint Detection Improves Process Control in Copper CMP", Semiconductor Fabtech Vol. 12, p. 283, 2000). Other process defects such as shorting can also occur in subsequent process steps. Direct measurements of metal thickness values are not possible using spectral reflectance data (unless the metal layer is less than a few hundred nanometers, which is normally not the case if fabrication processes are in or near specifications). However, by exploiting the high-spatial resolution spectral data of an embodiment, erosion measurements can be obtained.

To obtain erosion measurements, the reflectance apparatus of an embodiment is used to shine light onto an array of metal lines following a CMP step, where the incident light is in a plane parallel to the lines and perpendicular to the array of metal lines. Once such light is incident upon an array of metal lines, film thickness measurements of the top-most layer can be made at multiple locations on the image of wafer 1$d$ adjacent to and including a desired measurement site. These thickness measurements are obtained from between metal lines or vias. These measurements also include a measurement of a substantially un-eroded region. From these film thickness measurements an erosion value is calculated. One way of calculating the erosion value is to calculate the difference between the thickness top-most layer and the thickness of the thinnest top-most layer. The thickest top-most layer corresponds to the thickness of an un-eroded region, thus the difference corresponds to the amount of the top-most layer that has been eroded.

Figure 14:
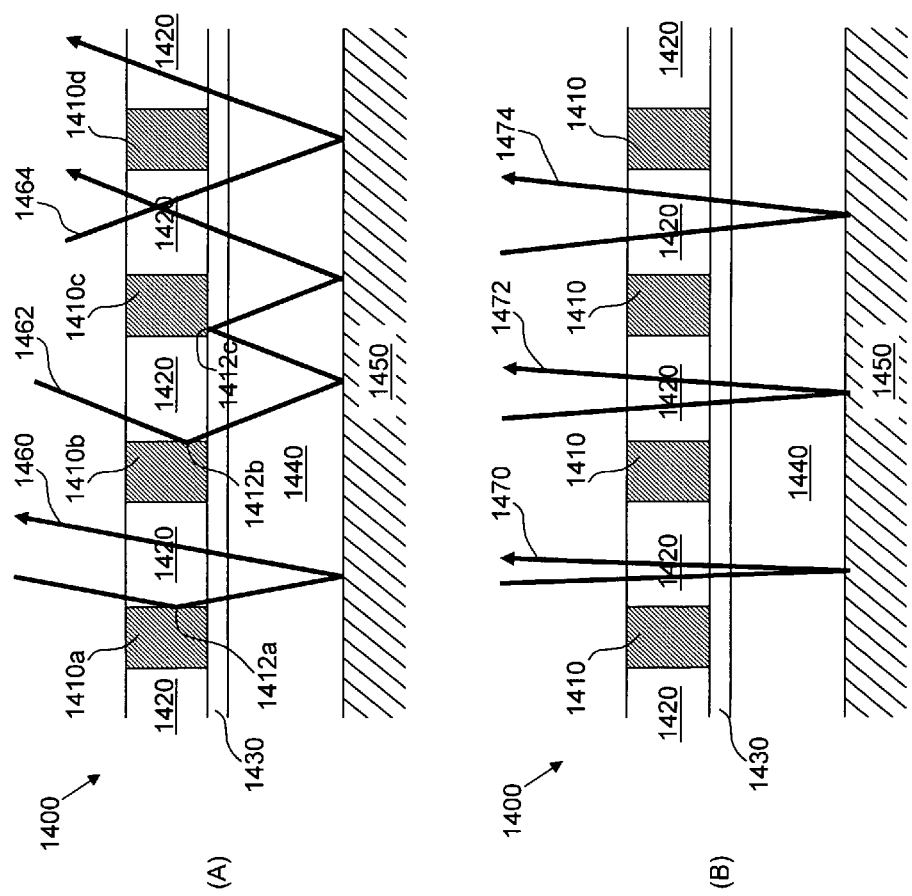
FIG. 14A illustrates the illumination of patterned features with broad angle, large numerical aperture light according to the system in accordance with the prior art.
FIG. 14B illustrates the illumination of patterned features with shallow angle, small numerical aperture light according to the system in accordance with the subject invention.

FIG. 14 shows an example patterned film structure 1400 that includes an array of copper lines 1410$a$–1410$d$ surrounded by silicon dioxide 1420 over a thin layer of silicon nitride 1430 and a second layer of silicon dioxide 1440 and a silicon substrate 1450. FIG. 14(A) shows incident light rays 1460, 1462, and 1464 striking patterned structure 1400 at a range of relatively large incident angles. Incident light rays 1460, 1462, and 1464 strike copper lines 1410$a$–1410$c$ at sidewalls 1412$a$ and 1412$b$ and at underside 1412$c$ respectively. For simplicity no refractive or diffractive effects are included though they would be present. In particular, light ray 1460 strikes copper line 1410$a$ at sidewall 1412$a$, and reflects off substrate 1450 before passing between copper line 1410$a$ and 1410$b$ before leaving patterned structure 1400. Light ray 1462 demonstrates different behavior in that after reflecting off sidewall 1412$b$ of copper line 1410$b$ and substrate 1450 it reflects off underside 1412$c$ of copper line 1410$c$, which leads to a second reflection off substrate 1450 before exiting patterned structure 1400. In general, a multiplicity of reflections between copper lines 1410 and substrate 1450 is possible, each reflection of which introduces increased dependence of the reflectance spectrum upon the copper lines. Light ray 1464, which has a relatively large incident angle, undergoes a single reflection off substrate 1450 before exiting patterned structure 1400. Light rays 1460 and 1462 have optical path lengths that depend significantly upon parameters of the copper lines such as width, thickness, and sidewall angle. Consequently, the overall reflectance signal depends significantly upon these physical parameters. In general, the greater the angle of the incident light, the more the light interacts with and is sensitive to the copper line dimensions and shape.

In contrast, FIG. 14(B) shows that light with a small NA incident at small angles leads to a high percentage of light passing by copper lines 1410 with reduced deflections off sidewalls 1412, reflecting off substrate 1450, and passing again between copper lines 1410 with substantially reduced reflections off of sidewalls 1412. Thus, by using small NA light rays incident at a small angle the extent of the variation of reflections due to variation of patterned features such as copper lines 1410 is minimized, which leads to significantly reduced sensitivity of the reflectance spectrum to variations in the copper line dimensions. This means that erosion can be measured with this simple system without undue sensitivity or interference from variations in metal line dimensions. The metal lines still have to be accounted for when modeling the wafer structure to determine the thickness of the top oxide layer using well-known methods such as Rigorous Coupled Wave Analysis (RCWA). Normally encountered variations in the metal dimensions are typically not enough to cause inaccuracies in oxide thickness determination. In contrast, high-NA measurement systems, such as those previously mentioned that use microscope objectives to acquire spectral reflectance from a single point, are much more sensitive to variations in metal line dimensions because of the effect such variations have on the overall reflectance.

The reflectance of light incident upon an array of lines such as copper lines 1410 depends in part upon the polarization of the incident light and the orientation of copper lines 1410. Copper lines 1410 thus behave like a wire grid polarizer, as described in U.S. Pat. No. 6,532,111. Thus the polarization of the light in apparatus 100 may be restricted to one polarization and this effect may be used advantageously in combination with the advantages of the low NA, low incident angle light in analyzing three-dimensional structures. If the incident light in system 102 is linearly polarized as a result of polarizer 1020 so that the light has an electric field nominally perpendicular to copper lines 1410, then the light passes easily into the patterned structure 1400 where it reflects and again passes easily out of patterned structure 1400. If the incident light has an electric field nominally parallel to copper lines 1410, then a greater portion of the light reflects from the patterned structure 1410 compared to the case of light with an electric field perpendicular to copper lines 1410. Arrays of conductive lines on a patterned semiconductor wafer are almost always parallel or perpendicular to a notch line extending from the wafer center to the notch.

In addition, each metallization layer generally has almost all lines oriented in the same direction. Thus, one can rotate wafer 1d using platform 2 so that the lines are perpendicular to the electric field of the polarized light so that most of the light passes through the metal features and ensuing measurements are therefore particularly sensitive to layers between and beneath the metal features. Likewise, platform 2 can be used to rotate wafer 1d so that the metal lines are parallel to the electric field of the polarized light so the ensuing measurements are more sensitive to light reflecting off of the top of the metal features. Such measurements are more sensitive to the layer above the metal features than to layers below the lines. In other cases where it is not possible to rotate the wafer or where horizontal and vertical lines are approximately equally abundant, it may be preferable to use randomly polarized light or circularly polarized light so that the reflectivity is substantially insensitive to the orientation of the wafer.

Figure 15:
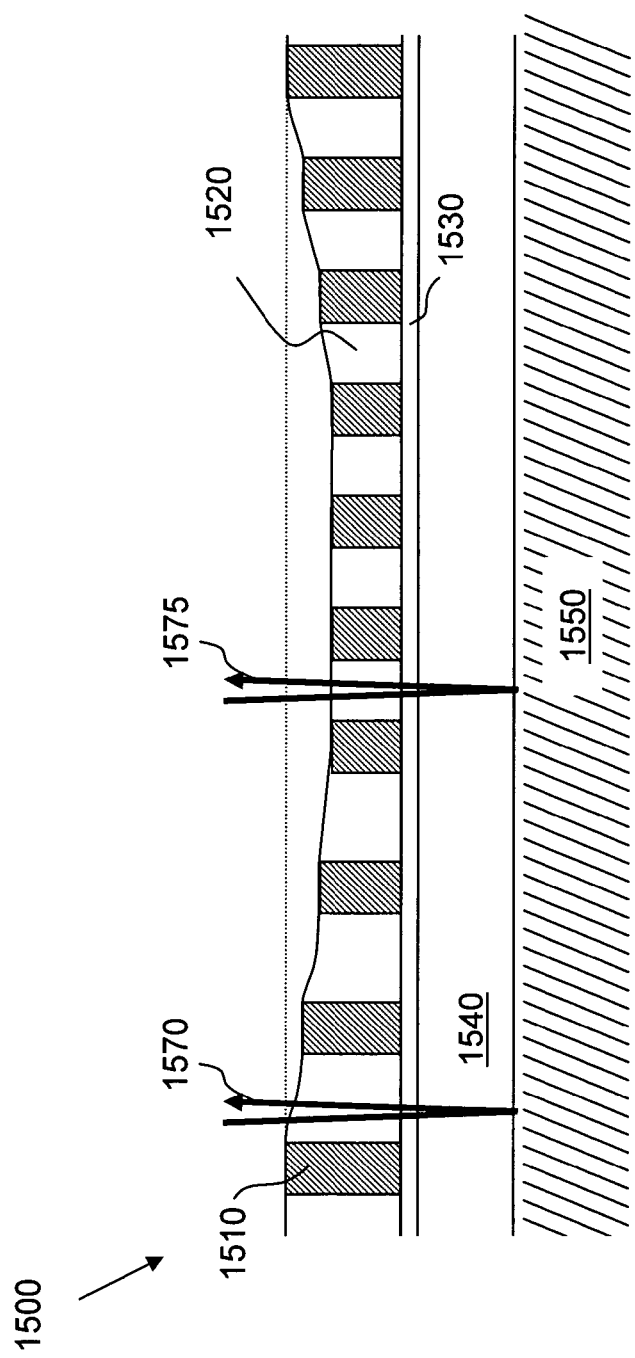
FIG. 15 shows measurements of erosion using the system in accordance with the subject invention.

FIG. 15 shows an example of how the apparatus of an embodiment is used to determine erosion. In particular, FIG. 15 shows a patterned structure 1500 that has erosion. This structure includes an array of copper lines 1510 between which is silicon dioxide 1520. The copper lines 1510 are on a layer of silicon nitride 1530 and a second layer of silicon dioxide 1540 on a substrate 1550. A spectral image of patterned structure 1500 includes reflectance due to light ray 1570 and 1575, where light ray 1570 passes between copper lines 1510 where there has been minimal erosion. Light ray 1575 passes between copper lines 1510 where there has been substantial erosion. Thus, step 1955 involves determining a first thickness of silicon dioxide 1520 from light ray 1570 and a second thickness value of silicon dioxide 1520 from light ray 1575, and calculating a net difference value between the first thickness value and the second thickness value. The net difference value is the erosion.

Correcting Second Order Diffraction Effects

The apparatus of an embodiment can be used to correct for spectral overlap errors that distort the signal detected and cause errors. Light incident upon a grating at a given angle of incidence α satisfies the grating equation, mλ=d (sin α+sin β), where m is an integer, β is the diffraction angle and d is the grating period. For a given grating, there exist values of m and λ that satisfy the grating equation and result in light diffracting into the same angle, e.g. m=1 and λ, m=2 and λ/2, m=3 and λ/3, etc. Thus, a detector positioned to receive first order light corresponding to m=1 and λ also receives second order light corresponding to m=2 and λ/2, as well as third order light (m=3 and λ/3), etc. The number of orders that must be accounted for depends on the diffraction efficiency of diffraction grating 7 for each order, the range of wavelengths of light emitted by light source 3, and the range of wavelengths over which two-dimensional imager 8 is sensitive.

By way of example, if using a light source with a range of wavelengths extending from 400 nm to 1000 nm, diffraction grating 7 scatters second order light from light having a wavelength of 400 nm into the same angle as first order light having a wavelength of 800 nm. A pixel in two-dimensional imager 8 aligned to receive the 400 nm light also receives the 800 nm light. In a similar manner, light from wavelengths ranging from 400 nm to 500 nm is scattered onto pixels that receive light ranging from 800 nm to 1000 nm. For this particular configuration, no third order spectral overlap correction is needed, and the response of two-dimensional imager 8 is given by $$I(\lambda)=I_1(\lambda)+I_2(\lambda/2)\cdot C(\lambda) \qquad (3)$$

where $I(\lambda)$ is the measured response at a given wavelength, $I_1(\lambda)$ is the contribution due to first order diffracted light, and $I_2(\lambda/2)$ is the contribution due to second order diffracted light from $\lambda/2$, and $C(\lambda)$ is a correction factor.

Method for Compensating for Second Order Overlap

Figure 16:
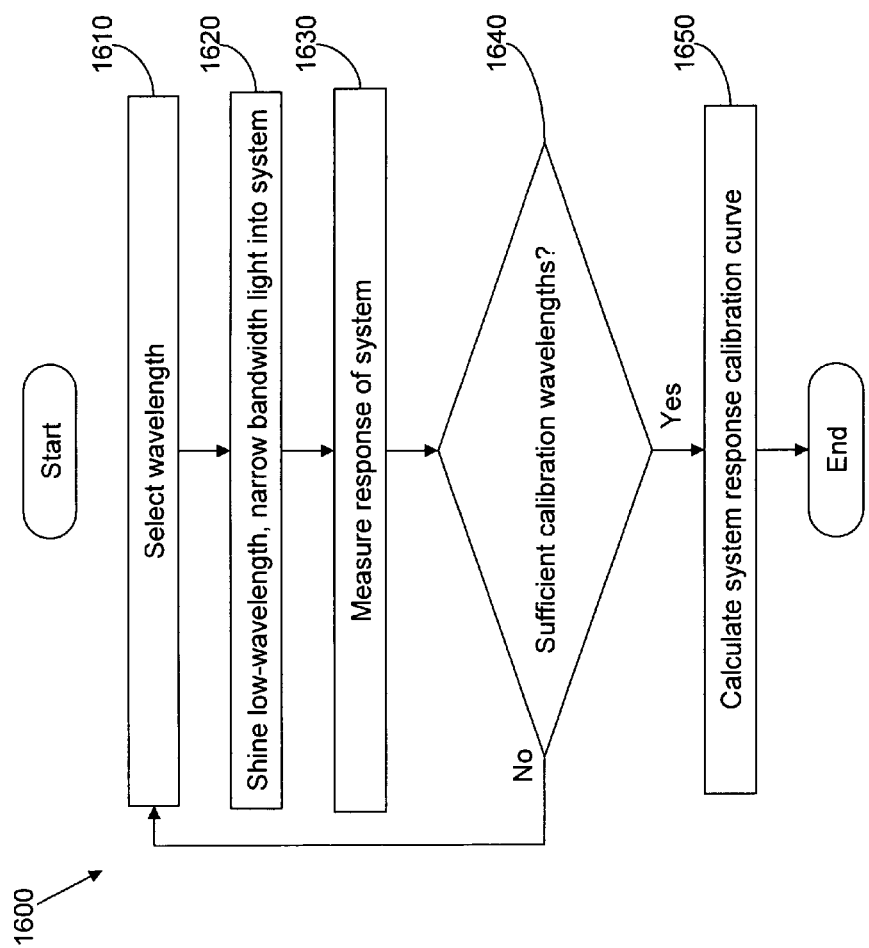
FIG. 16 is a flowchart showing a method of compensating for second order spectral overlap using the apparatus of the subject invention.

To account for spectral overlap of first and second order diffracted light in a system where orders higher than second are not present, Method 1600 shown in FIG. 16 can be used. This method involves calibrating the response of two-dimensional imager 8 to second order diffracted light at several calibration wavelengths between the smallest wavelength of light that can be second order light and the upper limit of sensitivity of the detector. For example, if light source 3 has a minimum wavelength of 400 nm, and two-dimensional imager 8 has an upper limit of sensitivity of 1000 nm, then wavelengths in the range of 400 nm to 500 nm are selected.

Any of a variety of light sources can be used to provide narrow band calibration light including lasers and light emitting diodes. Furthermore, a relatively broadband source in combination with a narrow-band filter can also be used. However, light emitting diodes (LEDs) are preferred sources of light for this calibration procedure. Though lasers can also be used, they suffer the disadvantage of being of such narrow bandwidth that the exact location of light incident upon two-dimensional imager 8 is not known other than that it falls within the pixel the light strikes. In contrast, LEDs normally have a bandwidth of 10 to 20 nm, which means that when such light strikes two-dimensional imager 8 it covers more than one pixel. By using well-known curve-fitting algorithms, the exact location of the peak can be found.

Figure 17:
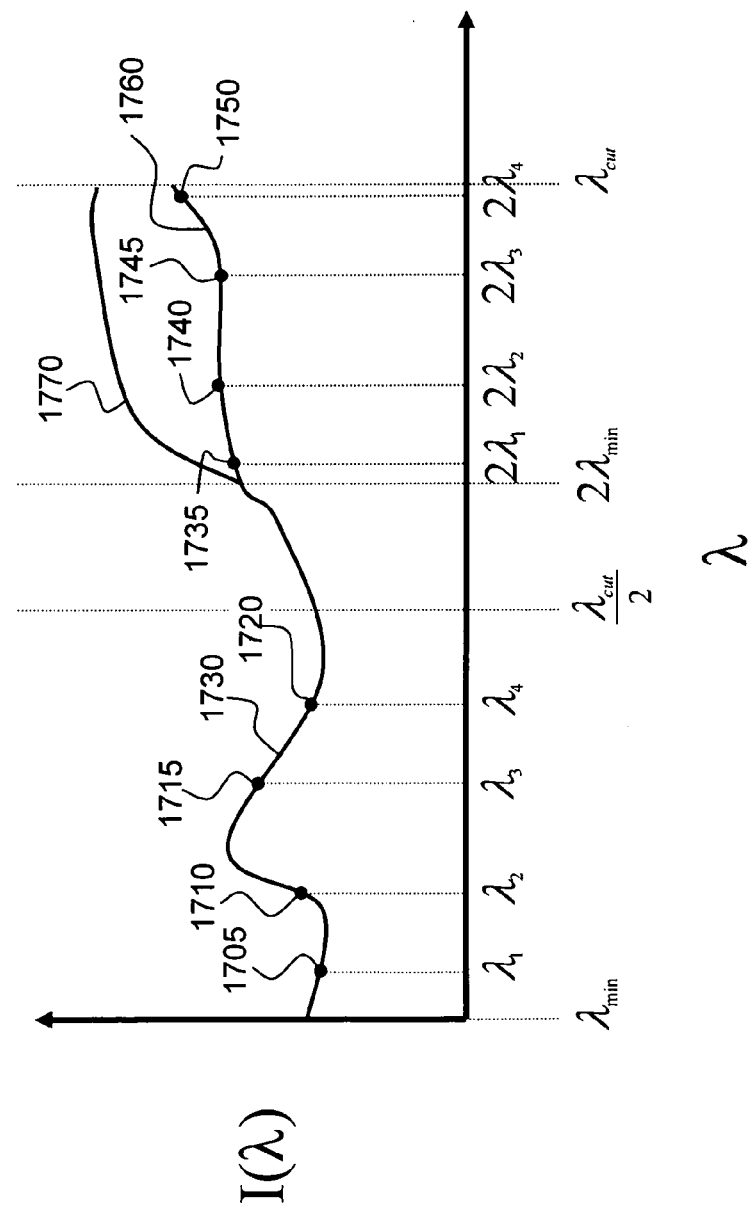
FIG. 17 shows the spectral response with and without compensation for second order spectral overlap.

FIG. 17 shows the effect of an un-corrected spectral response curve and a corrected spectral response curve. Between $2\lambda_{min}$ and $\lambda_{cut}$ spectral overlap occurs that must be corrected for. A spectral response curve 1730 extends from $\lambda_{min}$ to $2\lambda_{min}$. In this wavelength range there is no spectral overlap. Above $2\lambda_{min}$ is a spectral response curve 1770, which extends from $2\lambda_{min}$ to $\lambda_{cut}$ and includes both first and second order diffracted light. From equation (3) and from the figure, a portion of the light in this wavelength range must be subtracted from the total light detected to arrive at a corrected spectral curve. Equivalently, spectral response curve 1760 results from first order spectral light whereas spectral response curve 1770 results from first order spectral light augmented or distorted by second order light. Spectral response curve 1730, extending from $\lambda_{min}$ to $2\lambda_{min}$ and a spectral response curve 1760 extending from $2\lambda_{min}$ to $\lambda_{cut}$ constitutes the corrected spectral response curve.

Step 1610 of method 1600 involves selecting a calibration wavelength to use. Since the contributions due to second order effects tend to vary relatively smoothly over the affected range, it suffices to use approximately four calibration wavelengths in the range between the smallest wavelength and half the maximum wavelength at which the detector is sensitive. These wavelengths, designated as $\lambda_1$, $\lambda_2$, $\lambda_3$, and $\lambda_4$, are shown in FIG. 17. Using fewer than three wavelengths means that the correction is purely linear; using three wavelengths plus interpolation provides adequate correction. Using more than six wavelengths increases the accuracy of corrections, but at the expense of increased time.

Step 1620 of method 1600 involves directing the light into system 100 with light source 3 replaced by an LED emitting at a desired calibration wavelength. It should be noted that these calibration measurements can be performed with the angle $\alpha$ as small as zero degrees. Light at calibration wavelength $\lambda_1$ leads to first order intensity 1705 and second order intensity 1735 at $2\lambda_1$. Likewise, light at calibration wavelength $\lambda_2$ leads to first order intensity 1710 and second order intensity 1740 at $2\lambda_2$, light at calibration wavelength $\lambda_3$ leads to first order intensity 1715 and second order intensity 1745 at $2\lambda_3$, and light at calibration wavelength $\lambda_4$ leads to first order intensity 1715 and second order intensity 1740 at $2\lambda_4$.

Step 1630 of method 1600 involves sensing the light, including both first and second order wavelengths, and recording these measurements. By hypothesis, diffraction grating 7 is generates first and second order diffracted light that strikes two-dimensional imager 8 at two locations on two-dimensional imager 8. This measurement results in a curve with two sharp peaks, a first peak corresponding first order diffracted light and a second peak corresponding to second order diffracted light. This curve is saved in memory.

Step 1640 of method 1600 assesses whether sufficient different wavelengths of light have been used. If measurements at sufficient wavelengths have been made, then the logic of method 1600 moves to Step 1650; if not, then the logic of method 1600 moves to Step 1610 and another wavelength is chosen.

Step 1650 of method 1600 calculates a system response based on measurements obtained in Step 1630. For each intensity curve, i.e., for each calibration wavelength, the intensity values adjacent to a nominal peak that exceed a threshold value are selected. A peak-finding algorithm is used to determine precisely each peak amplitude and wavelength, one for first order diffracted light and one for second order diffracted light. Such peak-finding algorithms are well known; examples of such algorithms include parabolic fitting and Gaussian fitting. This peak-finding process is repeated for each calibration wavelength.

Having obtained precise peak amplitudes and wavelengths for each first and second order calibration wavelengths of light, a ratio of the peak amplitude corresponding to first order diffracted light to the peak amplitude corresponding to second order light is calculated, viz., $$R_i(\lambda_i) = \frac{I_2\left(\frac{\lambda_i}{2}\right)}{I_1(\lambda_i)}. \quad (4)$$

where i ranges from 1 to the number of calibration wavelengths used, e.g. N (where N is typically 4).

Figure 18:
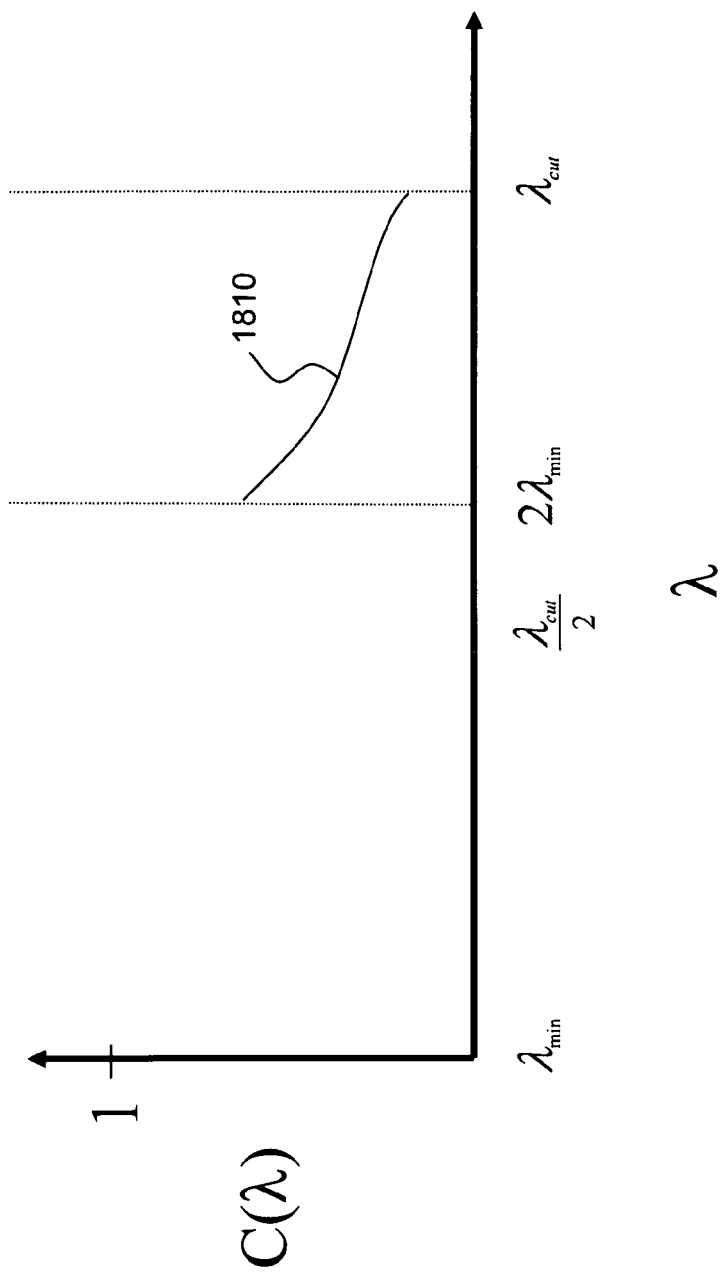
FIG. 18 shows the correction factor for compensation for second order spectral overlap.

Step 1650 concludes by calculating the correction factor $C(\lambda)$ by interpolating $R_i(\lambda_i)$ for wavelength values between $\lambda_1$ and $\lambda_N$ and extrapolating for wavelength values between $2\lambda_{min}$ and $\lambda_{cut}$ that lie outside the range $\lambda_1$ and $\lambda_N$. The result is a piece-wise continuous correction factor 1810 shown in FIG. 18. Step 1650 concludes by storing the correction factor $C(\lambda)$ in memory.

Compensating for Non-Constant Wafer Velocity

Depending on the motion of wafer 500 during measurements, irregularities in the ensuing image may occur that cause image distortion. These irregularities result from non-constant wafer velocity during the measurement process. Consider first the case of uniform linear motion in a direction perpendicular to the plurality of locations 634. Depending on the sampling rate, and assuming a full-wafer image, the resulting image is either a circle (which is good), or an ellipse. Whether the semi-major axis of the ellipse is disposed along the direction of motion or transverse to it depends on the linear velocity. In either case, the streets are straight lines, but they do not intersect at right angles. This distortion can be corrected for by a linear remapping of the image using correction factors obtained by determining the length of the semi-major and semi-minor axes of the ellipse. However, there exists a faster method.

Along any chord or diameter extending across the wafer image in the direction transverse to the direction of motion, the distinctive character of the streets allows them to be identified. Using similarly identified streets in adjacent chords, tangents at the intersection of the chord and the streets can be formed. Alternate tangents point in the same direction because of the linear velocity, and they correspond to either horizontal or to vertical rows. These tangents depend only on the linear velocity of the wafer during the measurements, and on the sampling rate. Thus, they can be used to infer the actual wafer motion at the moment of the measurement.

This algorithm is based on extracting information from a single chord. For a wafer moving at a constant velocity, this single measurement applies to the entire wafer. Any chord spanning the wafer thus contains sufficient information to extract the wafer velocity, and therefore to infer how to correct for it.

Since this algorithm applies to a single chord, which is obtained in a short measurement time, it can be applied to small areas of the wafer and to situations where the motion is non-uniform. Examples of such motion include the motion that a wafer undergoes if being manipulated by a robot arm on an R-θ stage, or on a CMP tool undergoing orbital, or rotational, or linear motion. Examples of such CMP motion are described in U.S. Pat. No. 4,313,284, U.S. Pat. No. 5,554,064, and in U.S. Pat. No. 5,692,947.

Figure 19:
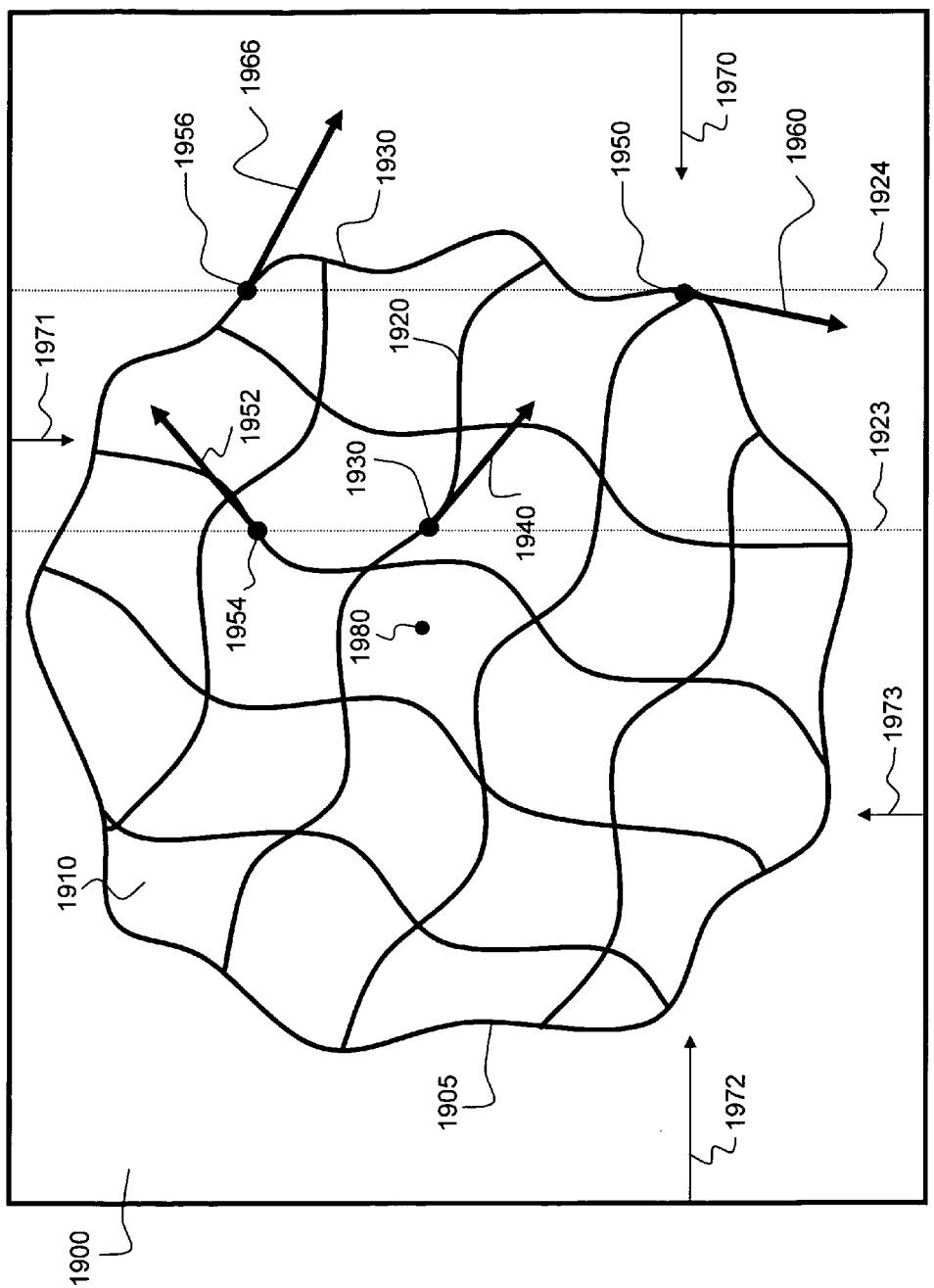
FIG. 19 shows an image of a round wafer undergoing non-uniform motion during the measurement.

To explain the application of this algorithm to non-uniform motion, consider FIG. 19. Neglecting the effect on intra-die structure (the viable die region), the image may appear as shown in FIG. 19, which shows reflectance data 1900 at an arbitrary wavelength that includes wafer image 1910 having a plurality of street images 1920, and a wafer edge image 1905. Street images 1920 appear as wavy lines due to non-uniform velocity. Since it is known a priori that the streets are actually straight and that there are horizontal and orthogonally oriented vertical streets (albeit rotated at a rotational angle θ), the waviness provides a way to infer the precise amount of velocity non-uniformity. More importantly, the waviness in combination with the fact that the streets are actually straight can be used to correct for the non-uniform velocity. To correct for the distortion in wafer images, find selected features in key locations and examine tangent lines to the features at these points. There are two cases to consider: one, where the streets are actually oriented horizontally and vertically (corresponding to rotational angle θ equal to 0°, 90°, 180°, or 270°); and two, where the streets are not so oriented.

For the first case where the streets are oriented horizontally and vertically, note that when the plurality of locations 634 spanning the entire diameter of wafer 500 sweeps across wafer 500, data is recorded from points not on wafer 500 in addition to points on wafer 500. The first step is to find wafer edge image 1905 by sequentially examining points from the edge of reflectance data 1910, for example by examining the points along the dotted line 1924 in the direction of the line designated by the numeral 1973. Reflectance values corresponding to points off the wafer are less than a threshold value, which facilitates finding an edge point 1950 on wafer edge image 1905. Suitable threshold values range from 0.002 to 0.30, but a preferred value is 0.01. (This technique can be applied in other directions, e.g. along directions indicated by lines 1970, 1971, and 1972 to find edges around all around wafer image 1910.) By examining data in columns in a similar manner to find adjacent edge points, a tangent line 1960 at edge point 1950 is created. The additional points, in the presence of non-uniform motion, may include some curvature, which can be determined through the use of well-known curve-fitting algorithms. A similar process leads to determining a tangent line 1966 at an edge point 1956. The direction of tangent line 1960 is related to the angle of the edge of wafer 500 and the wafer velocity. This process works for all edge points except at the wafer top, the wafer bottom, and at the midpoints. However, it works at all other points, which makes this technique suitable for correcting for distortion due to non-uniform wafer velocity when the streets are oriented for values of θ equal to 0°, 90°, 180°, or 270°.

For the second case, along dotted line 1923 in FIG. 19, consider a point 1930 in one of street images 1920 along with a tangent 1940 to street image 1920 at point 1930. Tangent 1940 depends on the rotation of wafer 500 during measurements, and of the rotational angle θ of wafer 500 at the moment of the measurement. The same methodology also leads to a tangent 1952 at a point 1954. As with case one, tangent 1940 and tangent 1952 are functions of the velocity and the rotational angle θ.

By obtaining tangents at two or more points on each chord across wafer image 1910, the image data in each chord can be corrected one chord at a time to yield a round wafer with straight streets.

Notch Finding

Once having corrected for distortions in wafer image 1910 it is highly desirable to identify the orientation of wafer image 1910. Since wafers include a notch to identify crystallographic orientation, the very high resolution of images formed with the apparatus of an embodiment renders this notch visible in wafer image 1910. Since wafers are usually loaded with the notch in a given position, the image of the notch is likely to be in a corresponding position. (However, the notch position can differ from the alignment of the wafer patterning by as much a degree or two).

Begin with the reflectance data 1900, and start from the top of the image and move down until wafer edge image 1905 is detected, as described above. Examine the reflectance at all wavelengths and using the highest reflectance compared to the threshold value. After finding wafer edge image 1905 along the top of wafer image 1910, the same edge finding technique is used again to find the bottom and the two sides of wafer image 1910.

Wafer 500 has a center point whose location is known to within a couple of millimeters, so a wafer image center point 1980 is also known to within a few pixels. To find the wafer image center 1980 of wafer image 1910, use chords across wafer image 1910. To identify exactly where wafer image center 1980 is, calculate the length of a chord extending across wafer image 1910 from a distance several pixels above the estimated location of wafer image center 1980 to several pixels below. The chord with the maximum length is a first diameter line that extends through the exact location of wafer image center 1980. Repeat this process for vertical chords to obtain a second diameter line. If the first diameter line and the second diameter line are the same (to within a couple of pixels), then the exact location of wafer image center 1980 is at the intersection of first diameter line and the second diameter line. If the first diameter line and the second diameter line are not the same (due to having stumbled upon the notch), then repeat the process of obtaining diameter lines along ±45 degree lines.

Having found the edges of wafer image 1910, the notch is found as follows. After determining the wafer center location, start at the top of wafer image 1910 and move around either clockwise or counter-clockwise. Each step involves moving either one pixel left or right or one pixel up or down, depending on where the center of the wafer is. For example, if starting at the top of wafer image 1910 then the wafer center is directly below. Pick a location in the column above the wafer center. If the point is not on the edge of wafer image 1910 (i.e., the point above is off the wafer and point below is on the wafer) then move either up or down until reaching the wafer edge image 1905. Once having found wafer edge image 1905, compute the squared value of the distance from the edge of the wafer to the center of the wafer and store it in memory. Then move one column to the left and again reacquire the edge by searching up and down until finding it. Then compute the center to edge distance squared of this new edge point and store it in memory.

Continue moving around the edge and computing the center to edge distance squared. Once having gone completely around the edge of the wafer, examine the accumulated center to edge distance squared data to find the notch. One way to find the notch involves examining the first derivative of the data. The first derivative is highest at the edges of the notch, and yields a good approximate location for the notch. To more precisely locate the notch once having found the notch using the first derivative, apply well-known curve-fitting algorithms to the tip of the notch.

Orienting Streets—Auto-Rotate

Once having determined where the notch is, it is highly desirable to more precisely align the streets so that measurements on small features can be made. An embodiment further includes such a process, which is called an "auto-rotate" process or algorithm. This algorithm involves accurately determining the rotational orientation of the spectral image of wafer 1*d*. This algorithm makes no assumption about spatial orientation, so this approach is particularly effective in processes such as CMP where wafers may slip during process.

The method described here takes advantage of the fact that wafer pattern features align orthogonally due to the step and repeat nature of patterns on partially processed integrated circuits. This effect is especially apparent in the streets regions between the die. When the features in the spectral image corresponding to streets are oriented so that they align substantially along the rows and columns of each slice of the spectral image, then a row or column summation preserves a signature indicative of these features. In contrast, if the wafer pattern features are not aligned, then the elements of the resulting row or column summation are more of an average from a much greater variety of areas of the wafer, and thus maintain much less feature differentiation.

To quantify this differentiation, and thus the degree to which the wafer features are aligned with the detector rows and columns, determine a single "Goodness-of-Alignment" value for a given orientation of the image of wafer 1d by: summing all of the reflectance values along each row to form a sequence of row sums; forming a difference column by calculating the difference between adjacent elements of the sequence of row sums, and determining the Goodness-of-Alignment value for the given orientation of the image of wafer 1d by summing each value in the difference row that exceeds a threshold value.

Figure 20:
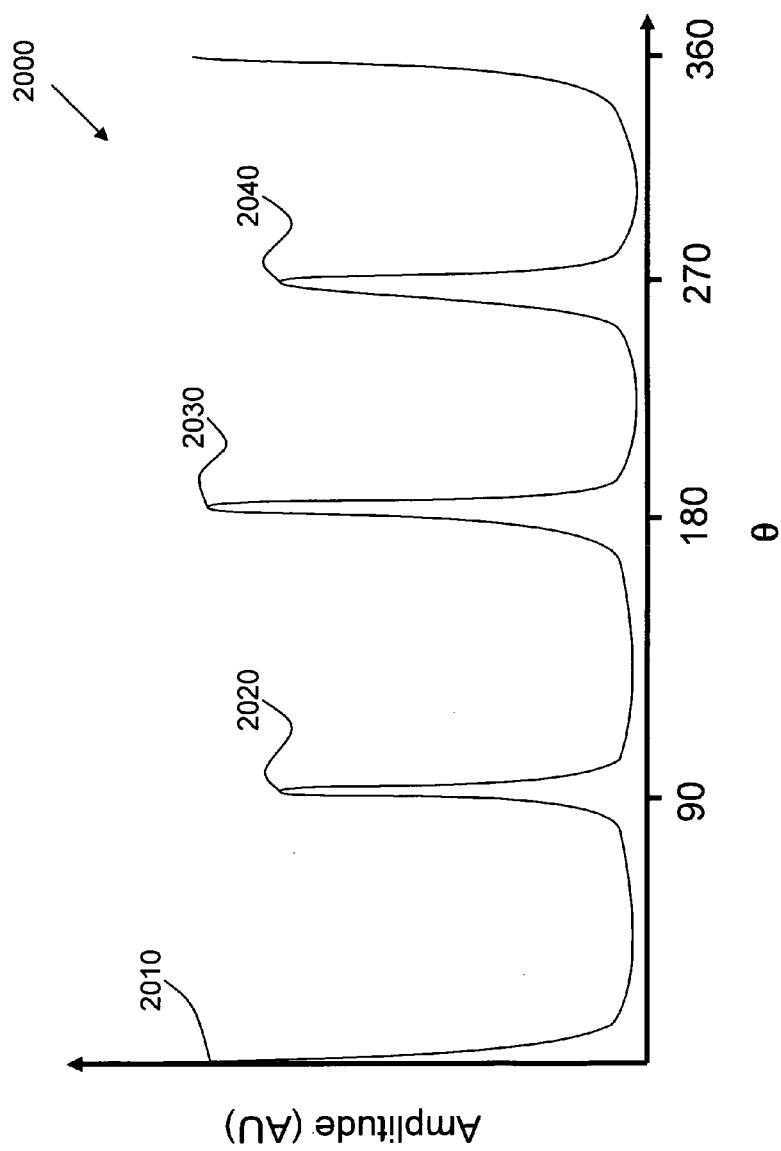
FIG. 20 shows an example of the Goodness-of-Alignment values as a function of rotational angle θ using the auto-rotate algorithm of the present invention.

Determining the orientation of the image of wafer 1d involves applying the above algorithm to the image of wafer 1d over a range of image rotations to generate a series of Goodness-of-Alignment values for different rotational orientations of the image of wafer 1d. The rotations are performed by applying the appropriate mathematical transformations to the image of wafer 1d. Such transformations are well known in the art, FIG. 20 shows an example of the resultant Goodness-of-Alignment values as a function of rotational angle θ. Notice that the Goodness-of-Alignment values have sharp maxima at ninety-degree intervals, which correspond to alignments between the pattern features and the rows and columns of the image of wafer 1d. These peaks are seen in practice. In FIG. 20, peak 2010 and peak 2030 correspond to vertical streets being oriented vertically, with peak 2030 corresponding to the wafer image being rotated 180 degrees from the orientation that produced peak 2010. Likewise, peaks 2020 and peak 2040 correspond to horizontal streets being oriented vertically with peak 2040 corresponding to the wafer image being rotated 180 degrees from the orientation that produced peak 2020. From this example it is clear that this method cannot easily determine the wafer rotation orientation angle uniquely, but rather it can determine that it is one of four different possible orientations.

In practice, however, the rotation angle is generally known to within 1–2 degrees (from notch-finding or a priori knowledge), so only a limited range of angles need to be analyzed, and the rotation angle can be determined uniquely to approximately 0.01 degrees of resolution. This resolution allows subsequent position finding steps to be done accurately and reliably.

An alternate approach to orienting the streets in the auto-rotate algorithm involves using light in a single narrow band is used instead of using all of the light. One suitable wavelength is 660 nm.

It is also possible to create a vertical or horizontal orientation line using more than one wavelength, or to use multiple wavelengths, i.e., spectra arising from light passing through multiple bandpass filters. Though summing the optical reflectance at each wavelength used is possible, summing the ratio of the optical reflectance at each of two wavelengths allows the creation of an orientation line with additional pattern dependent structure. One example is to use a relatively blue wavelength, for example 410 nm, and a relatively red wavelength, e.g. 660 nm.

An optional step within the autorotate algorithm is to obtain a die signature. Once the image of wafer 1d has been oriented, pattern recognition techniques are used to identify in wafer image 1d the locations of portions, e.g. quadrants of individual die. Unless each die is exactly symmetric about its center point, the reflectance in different quadrants of each die vary from quadrant to quadrant is asymmetric. These variations from quadrant to quadrant constitute a signature indicative of the orientation of each die. An additional technique is to use the ratio of reflection intensities at different wavelengths as described above.

Rotational Auto-Rotate

Yet another approach to obtaining an oriented wafer image is to analyze an image of a portion of a patterned wafer, where the portion of the wafer being examined includes a street at the radial distance from the wafer center, but at an unknown angle. There are two situations to consider. In both situations, the nominal location of the wafer center is known to within tens of microns, but the notch is at an unknown angle albeit at a known radius. In the first situation the wafer center lies within a center die, and in the second situation a street (either horizontal or vertical) traverses the center of the wafer. This rotational method of orienting wafers involves using system 100 to measure reference wafers and non-reference wafers with the same pattern as the reference wafer.

The rotational method includes positioning line imaging spectrometer 11 so that it images a portion of the wafer along a line perpendicular to a radial line extending from the center of wafer 1d to the edge of wafer 1d. Line imaging spectrometer 11 substantially straddles the radial line. If dealing with the first situation where the center of the wafer falls within the center die, line imaging spectrometer 11 is disposed to image a portion of wafer 1d at a half-die width equal to one half of the die height away from the wafer center. Thus, for some rotational angle θ the reflectance data pertains to light reflecting substantially from a street portion of wafer 1d. If dealing with the second situation, line imaging spectrometer 11 is disposed to straddle and to image the center of wafer 1d.

The rotational method then involves rotating the wafer about its center point with line imaging spectrometer 11 held at the half-die width (situation one) or at the wafer center (situation two). While rotating the wafer, computer 10 records reflectance data sensed by line imaging spectrometer 11. For each rotational angle θ, computer 10 forms an orientation signal by summing all the pixels in each row over all wavelengths.

A plot of the orientation signal as a function of rotational angle has peaks corresponding to the street being optimally aligned with the portion of wafer 1d being imaged. For situation one, two peaks are present, thus providing orientation to within ±180 degrees. For situation two, four peaks are present if the wafer center aligns with the intersection of both vertical and horizontal streets; otherwise only two peaks are present.

To account for situations where the known uncertainty in the portion of wafer 1d being imaged results in this portion not being substantially aligned with the streets of wafer 1d, a reference method is used. The reference method involves using the aforementioned rotational method to obtain a clear orientation signal referred that serves as a reference orientation signal, and is stored in memory. A subsequent measurement on another wafer having the same pattern on it is then measured to obtain a test orientation signal that is compared with the reference orientation signal. The test orientation signal is likely to exhibit a poorer quality indication that line imaging spectrometer 11 are aligned with the streets due to the uncertainty in the location of the wafer center. However, as long as the test orientation signal exhibits well-defined peaks, the reference method can be used to determine the proper orientation of the wafer.

Numerous techniques can be used to compare the test orientation signal with the reference orientation signal. One such technique is to use a one-dimensional cross-correlation function.

$$C_{tr}(\theta) = \overline{t(n)r(n-\theta)} = \frac{1}{N}\sum_{n=0}^{N-1} t(n)r(n-\theta)$$

where t(n) and r(n) are the test and reference orientation signals respectively, N is the number of pixels in a row, and θ is the correlation angle. The angle corresponding to maximum correlation corresponds to the desired rotational angle. Another comparison technique involves calculating a difference between t(n) and r(n−θ) and identifying the minimum such difference as corresponding to the desired rotational angle. Additional techniques using the method of least squares can also be used.

Calibrating Each Individual Column of the 1-D Spectrometer Independently with a Monochromatic Light Source The process of matching model spectra to measured spectra requires that the measured spectra are correct. It is also advantageous to perform the following calibration procedure to ensure that measured spectra are indeed mapped to the proper wavelengths. To perform such a calibration, the apparatus used for correcting for second order spectral overlap is used. In particular and referring to FIG. 1, light source 3 of system 100 is replaced with an LED or with broadband light passed through a bandpass filter to produce light with a 10–20 nm bandwidth. Consider the implementation where two-dimensional imager 8 is a CCD; the spatial dimension is the horizontal dimension, and the spectral dimension is the vertical dimension. Light from the 10–20 nm light source should give a uniform response from two-dimensional imager 8. In other words, the row element exhibiting the maximum response along the columns corresponding to the spectral dimension should be the same in each column across the spatial dimension of the array. Illumination with light having a 10–20 nm bandwidth is important so that several pixels sense the light, and well-known curve fitting algorithms can be used to find an exact peak location, thus improving the accuracy of the calibration procedure. If the response is non-uniform across two-dimensional imager 8, then the wavelength can be corrected by fitting the measured response to a second order polynomial.

Repeating this calibration procedure at several wavelengths in the range of sensitivity of two-dimensional imager 8 maximizes the accuracy of the calibration. This calibration process can be done at different wavelengths sequentially, or simultaneously.

Decreasing Minimum Pad Size Requirements

The evolution of integrated circuit (IC) technology has led to ever-decreasing critical dimensions. Associated with this reduction has been a reduction in the size of test sites, which are bond-pad like features that are typically large compared to device features. Typically, many such sites are located on each wafer on which ICs are being fabricated. Since most existing tools for measuring test sites involve the time-consuming and hence expensive serial data acquisition, few test sites are measured due to the time-consuming nature of existing metrology techniques. The embodiment described above and as shown in FIG. 1 and FIG. 3, as well as in U.S. patent application Ser. No. 09/899,383, and U.S. patent application Ser. No. 09/611,219, describes how to obtain large numbers of measurements on bond pads as small as 100 um. In spite of these embodiments, there remains a need for a capability of accurately and reliably measuring thin films at test sites on wafers, where the test sites are as small or smaller than 50 um.

To appreciate the benefits of several techniques described below to measure smaller test sites, it is useful to recall that optical systems such as those described herein involve an object (e.g. wafer) and a collection of optical elements disposed to create an image in an image plane that coincides with the sensing portion of a multiple-pixel, two-dimensional imager. Such systems also function in reverse, i.e., the collection of optical elements also images the multiple-pixel, two-dimensional imager (now viewed as an object) onto a second image plane that coincides with the plane of the wafer. Thus, one can view such a system from the perspective of a wafer image on the multiple-pixel, two-dimensional imager, or as a collection of pixel images on the wafer.

To provide accurate and reliable measurement capability on such test sites requires that a measurement spot size be as small or smaller than the test site, and that one or more measurement spots lie substantially within the test site. The measurement apparatus one uses determines this capability. The minimum test site area that can be measured is determined by the measurement spot size, which is equal to the size of the "pixel image" that is imaged onto the wafer surface by the imaging system 100. The pixel image size is primarily determined in an embodiment in the horizontal direction by the pixel width multiplied by the product of the magnification of lens assembly 4 and the magnification of lens assembly 6 and in the scan direction by the slit width multiplied by the magnification of lens assembly 4.

The ability of a measurement system to measure a test site also depends on the measurement spot density, i.e., the number of measurements made per unit area on wafer 1d. In particular, using the apparatus of an embodiment, the measurement spot density is determined primarily by the density of pixel images in the horizontal direction and the scan speed in the scan direction. Clearly, the measurement spot size and the measurement spot density are affected by the magnifications of the lenses 4 and 6. Hereinafter, discussion addresses the effects of other factors on the measurement spot size and the measurement spot density. Therefore for simplicity we assume unity magnification for lens assemblies 4 and 6; this assumption allows us to ignore the distinction between the pixel and slit sizes and the pixel image size. However, it is not necessary to limit the scope of an embodiment to unity magnification of lens assemblies 5 and 6.

Ensuring that one or more measurement spots lie substantially within a test site involves either performing extremely precise measurements at locations whose position is known a priori to a high degree of precision (which is expensive and time-consuming), or by increasing the measurement spot density and rapidly sifting through the measured data. An embodiment involves performing sufficiently numerous measurements in a very short period of time that the very density of measurements combined with the small measurement spot size of individual measurements ensures that accurate measurements at desired test sites are made. Methods already described in U.S. patent application Ser. No. 09/899,383, and U.S. patent application Ser. No. 09/611, 219, address the issue of efficiently sifting through measurement data to extract measurements at desired test sites.

Standard solid-state imagers have rectangular pixels whose width is equal to the horizontal pixel pitch. This relationship implies a 100% fill factor, i.e., there is no portion of the sensing region of the imager that is not sensitive to light. However, for a given imager, improving the measurement spot size requires innovation.

Figure 22:
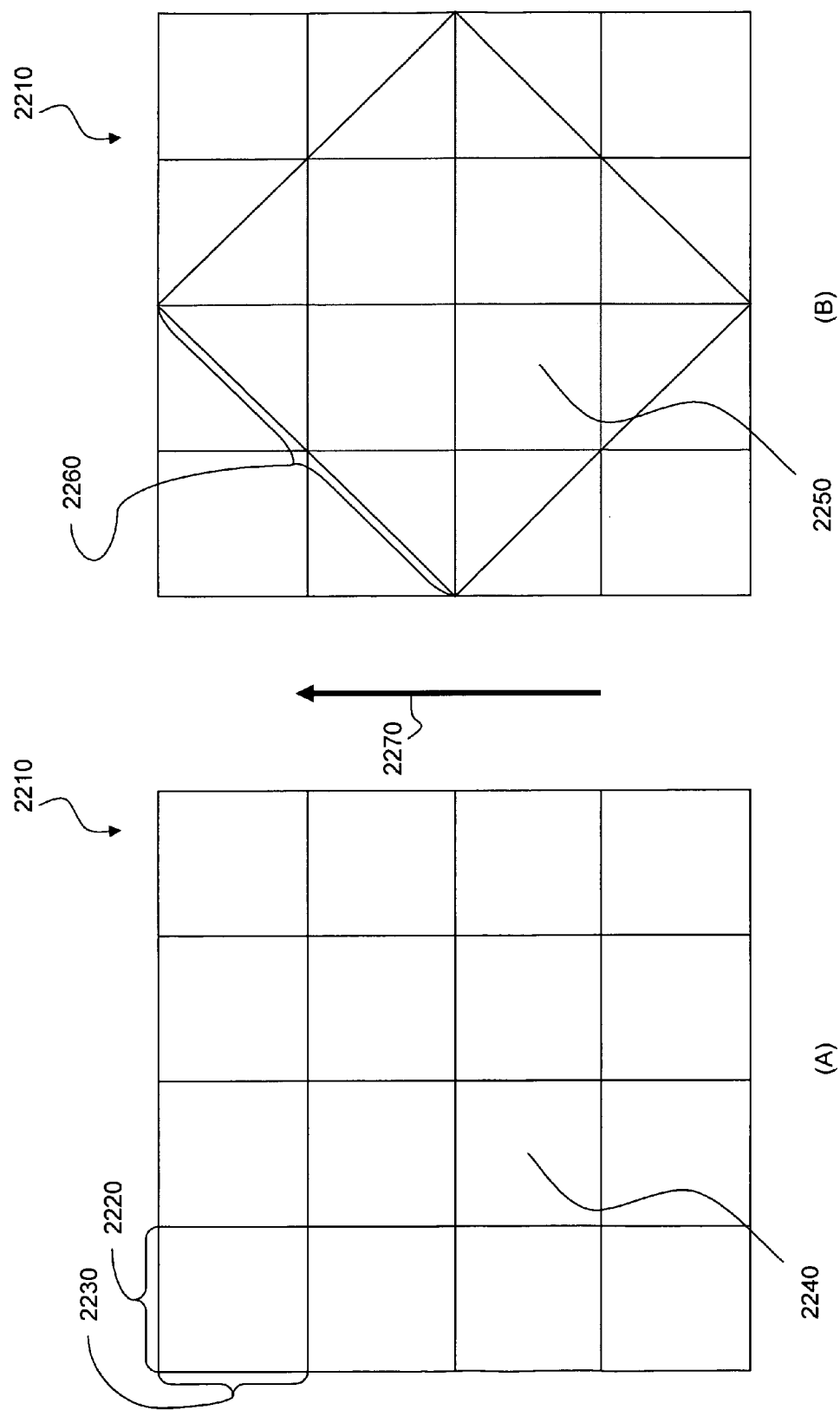
FIG. 22 shows measurement spot size for 100% fill factor imaging for (A) optimal wafer orientation, and (B) worst-case wafer orientation.

The measurement spot size depends in part on the orientation of the image of the measurement site compared to the orientation of the pixels in two-dimensional imager 8. FIG. 22(A) shows a 4×4 portion of a pixel array 2210 of two-dimensional imager 8 that has a 100% fill factor, and where each pixel has a horizontal dimension 2220 and a vertical dimension 2230. If the measurement sites are optimally oriented, as shown in FIG. 22(A), then the minimum measurement site image size is twice the pixel size. (Smaller site areas could straddle two pixels so that neither pixel would sense light from a single film stack, thus forming difficult or impossible to decipher measurements.) Pixel array 2210 moves in a scan direction indicated by an arrow designated by the numeral 2270. Superimposed on array 2210 is a measurement site image 2240. If the measurement site image size is any less than two times horizontal dimension 2220 or two times vertical dimension 2230 then there is a risk that a measurement will not include at least one pixel that is completely covered by the measurement site image.

However, it cannot be assumed that the measurement sites are optimally oriented since there is uncertainty in the orientation of wafer 1*d* on platform 2, even if wafer 1*d* is oriented prior to being placed on platform 2. The worst-case scenario is that the measurement sites are oriented at a 45-degree angle, as shown in FIG. 22(B), which shows a measurement site image 2250 oriented at a 45-degree angle to the pixels of pixel array 2210. Measurement site image 2250 has an edge dimension 2260 that has a minimum length of $2\sqrt{2}$ times horizontal dimension 2220.

To deal with the worst-case scenario, and to meet or exceed the minimum measurement spot size involves reducing the active area of the pixels that receive light. Embodiments described herein include several techniques that provide for this capability.

Pixel Masking

Decreasing the active area of the pixels that receive light can reduce the measurement spot size. For optimal results, this approach involves reducing the active area in both the horizontal and vertical directions. Masking the pixel area can achieve this reduction in the horizontal dimension. FIG. 23(A) shows a pixel 2310 to which an opaque material has been applied to form a mask 2320 and a mask 2330 that block light from reaching the active portion of pixel 2310, thus forming active area 2340 having a width 2345. Placing mask 2320 and mask 2330 near the outer edges of pixel 2310 optimizes the sensitivity of pixel 2310 to light and reduces electrical crosstalk between adjacent pixels, and it reduces resolution degradation caused by non-ideal optics (such as those that may be found in lens assemblies 4 and 6). The opaque material that forms mask 2320 and mask 2330 is deposited during the fabrication of two-dimensional array 8, using standard IC fabrication methods. Materials such as metals (aluminum, gold, silver, etc.) are suitable opaque materials. Advantageously, such materials are anti-reflection (AR) coated to suppress reflections.

Figure 23:
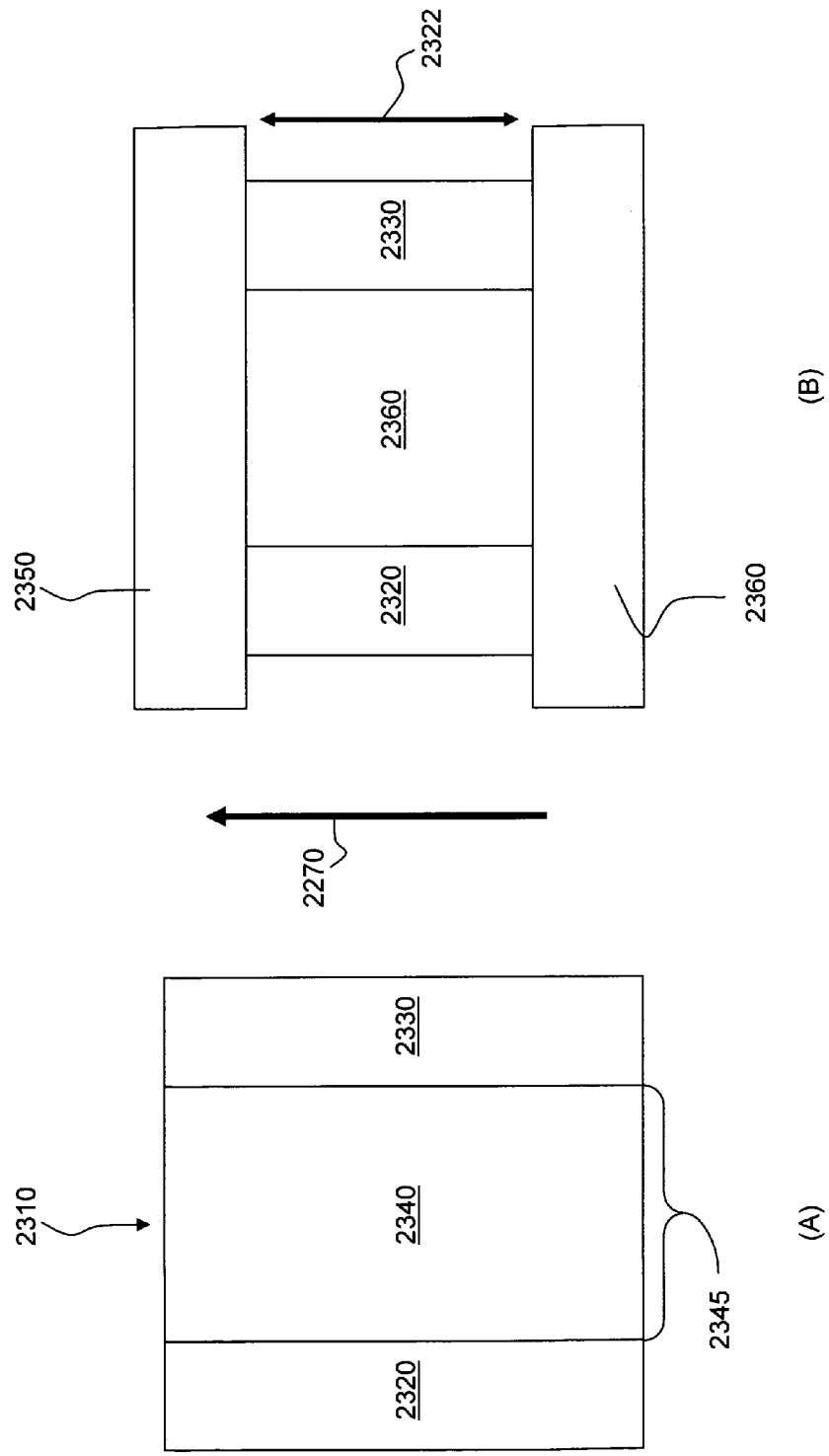
FIG. 23 shows how to mask individual pixels according to the present invention.

In the vertical dimension masking can also be used to reduce the pixel area. However, it is advantageous to adjust the slit width of slit 5, which has a blade 2350 and a blade 2360 separated by a height 2322 as shown in FIG. 23(B). The slit width of slit 5 is height 2322. This process results in an active area 2460 that is substantially smaller than the original active area of pixel 2310. Assuming that the resulting active area 2460 is square, then the minimum measurement site size is $\sqrt{2}$ times the sum of width 2345 plus height 2322. FIG. 24(A) shows a 4×4 portion of a pixel array 2410 of a two-dimensional imager that is identical to two-dimensional imager 8 except for the pixels being masked as shown in FIG. 23.

Pixel masking results in a decrease in fill factor to the product of height 2322 and width 2345 divided by the product of horizontal dimension 2220 and vertical dimension 2230. If height 2322 and width 2345 are one half of horizontal dimension 2220 and vertical dimension 2230 respectively, then the ensuing fill factor is 25%.

FIG. 24(B) shows a measurement site image 2450 oriented at a 45-degree angle to the pixels of pixel array 2410. Although measurement site image 2450 is nominally the same size as measurement site image 2250, measurement site image 2450 easily fits over four pixels in pixel array 2410, with considerable tolerance for rectilinear and/or rotational misalignment still yielding at least one pixel fully covered by measurement site image 2450.

Figure 24:
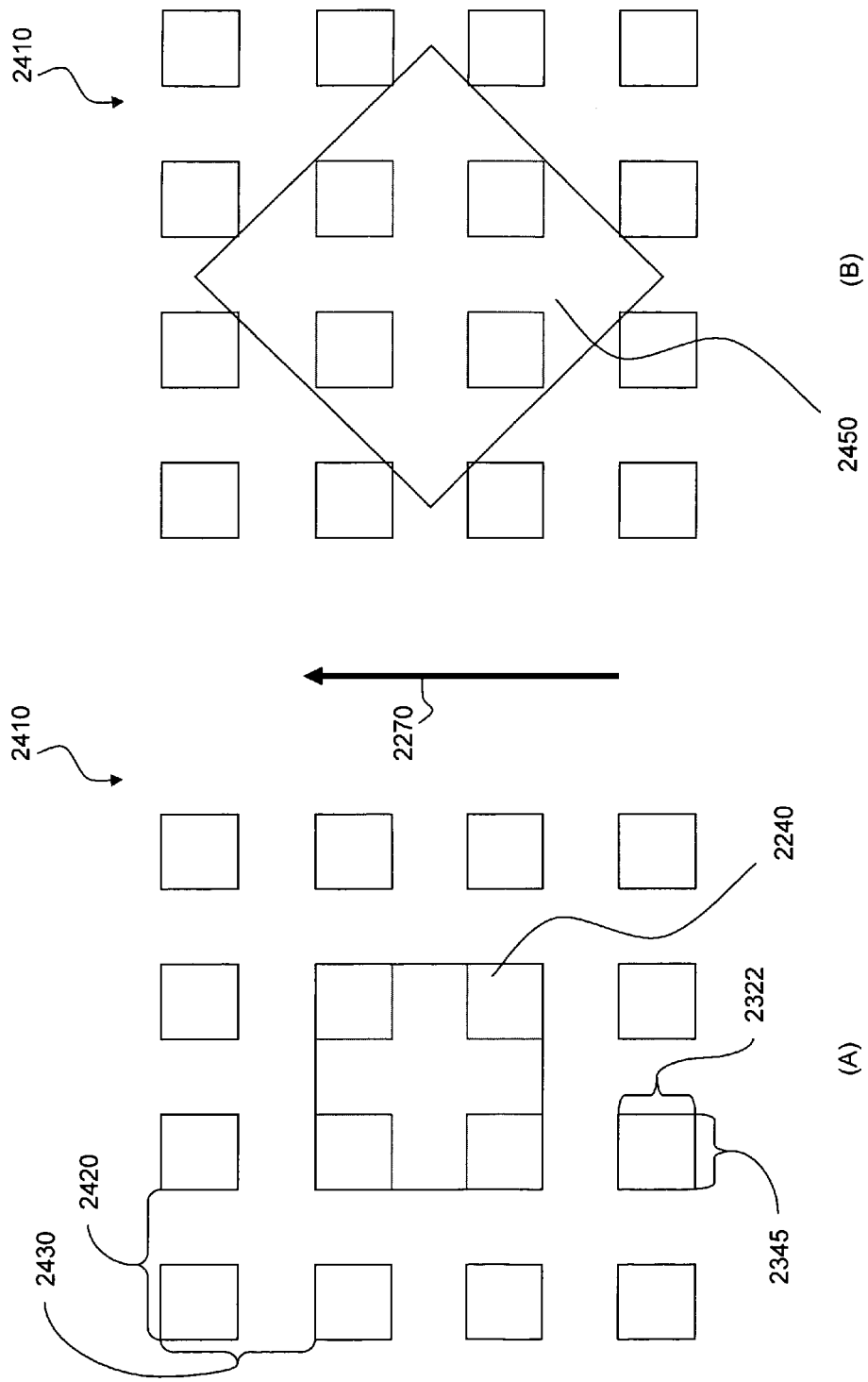
FIG. 24 shows measurement spot size for <100% fill factor imaging resulting from the use of masked pixels for (A) optimal wafer orientation, and (B) worst-case wafer orientation.

FIG. 24 shows the reduction in measurement spot size due to reducing each edge of active pixel area by one half, which leads to a 25% fill factor. Further reductions in active pixel area are possible, albeit with a corresponding decrease in the total amount of light that reaches the pixels. This reduction in light intensity can be compensated for by increasing the intensity of light source 3, or by using a more sensitive detector.

One very significant benefit to pixel masking is that the resulting reduced measurement spot size is much more likely to be entirely on a single film stack regardless of the orientation of any given measurement site relative to the pixels in imager 8. In contrast, large measurement spot sizes are much more likely to bridge two different film stacks, which result in a reflectance measurement that is difficult to decipher.

In operation, the scan speed is the same as its nominal speed. As wafer 1*d* moves, light from light source 3 reflects off wafer 1*d* and enters line imaging spectrometer 11 of system 100, where two-dimensional imager 8 has been replaced with two-dimensional imager 2410. Computer 10 receives spectral data from line imaging spectrometer 11, and generates spectral images of wafer 1*d* from which the film thickness of a film at desired measurement sites is determined, as described in U.S. patent application Ser. No. 09/899,383, and U.S. patent application Ser. No. 09/611,219.

Over-Sampling

There is in general no certainty that any given measurement spot will be on any one exact location on a wafer being measured. One reason for this uncertainty is a consequence of the already small spot size and the positional tolerances involved in wafer positioning and in mask alignment during normal processing conditions. A second reason has to do with tolerances in synchronizing data acquisition and wafer motion or positioning while collecting data.

Figure 25:
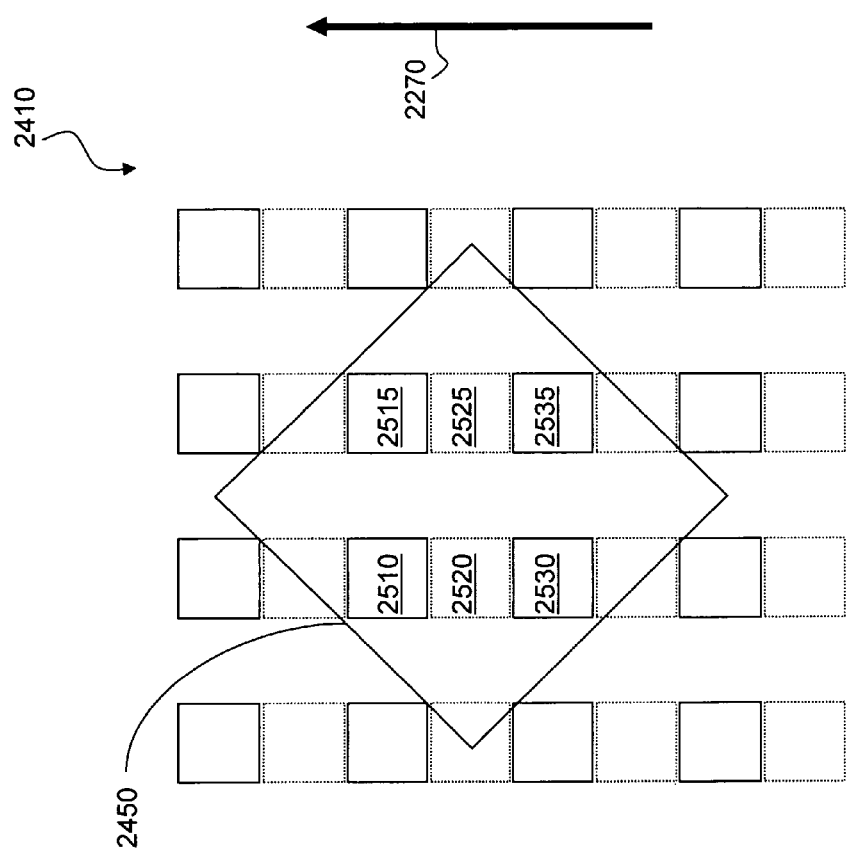
FIG. 25 illustrates the use of over-sampling to enhance vertical pixel image density using masked pixels according to the present invention.

A way to increase the probability that a measurement of wafer 1*d* using system 100 actually results in a measurement of a desired measurement site is to increase the measurement spot density by reducing the scan speed relative to the data acquisition rate. Although it is intuitive to set the scan speed to result in a measurement spot density that is equal in directions both parallel to and perpendicular to the scan direction, decreasing the scan speed by a factor of two while maintaining the data acquisition rate increases the measurement spot density by a factor of two. FIG. 25 shows measurement site image 2450 as well as pixel array 2410 at two sequential integration times. The first integration time corresponds to the dotted lines, and the second integration time corresponds to the solid lines. During the first integration time, a pixel 2520 and a pixel 2525 are entirely within measurement site image 2450. However, during the second integration time, a pixel 2510, a pixel 2515, a pixel 2530, and a pixel 2535 are entirely within measurement site image 2450. An ensemble image comprised of images recorded at both the first and second integration times leads to an image that includes six pixels that are covered entirely by measurement site image 2450 measurement site image 2450, which is a significant increase in the probability that a single sweep of measurements across wafer 1d results in high quality measurements at desired test sites. Further reducing the scan speed can lead to the case of "overlapping", i.e., where the measurement spots begin to overlay in the scan direction. Overlapping further reduces the minimum measurement site size.

The example just described serves to show how a 50% reduction in scan speed doubles the number of measurements made during a single sweep across wafer 1d using system 100, thus increasing the spatial resolution of measurements. Further decreasing the available light sensitive area by scaling each pixel down is one way to obtain additional resolution. Another way to obtain further increases in spatial resolution is to further reduce the active area of pixels by masking more of each pixel. Reducing height 2322 by adjusting blade 2350 and/or a blade 2360 appropriately leads to nominally square light sensitive regions. Further reducing the scan speed results in more measurements on wafer 1d. Depending on how much masking is done it may be necessary to increase the intensity of light generated by light source 3.

In operation, the scan speed is reduced to one half of its nominal speed. As wafer 1d moves, light from light source 3 reflects off wafer 1d and enters line imaging spectrometer 11 of system 100, where two-dimensional imager 8 has been replaced with two-dimensional imager 2410. Computer 10 receives spectral data from line imaging spectrometer 11, and generates spectral images of wafer 1d from which the film thickness of a film at desired measurement sites is determined, as described in U.S. patent application Ser. No. 09/899,383, and U.S. patent application Ser. No. 09/611,219.

Row Staggering

Figure 26:
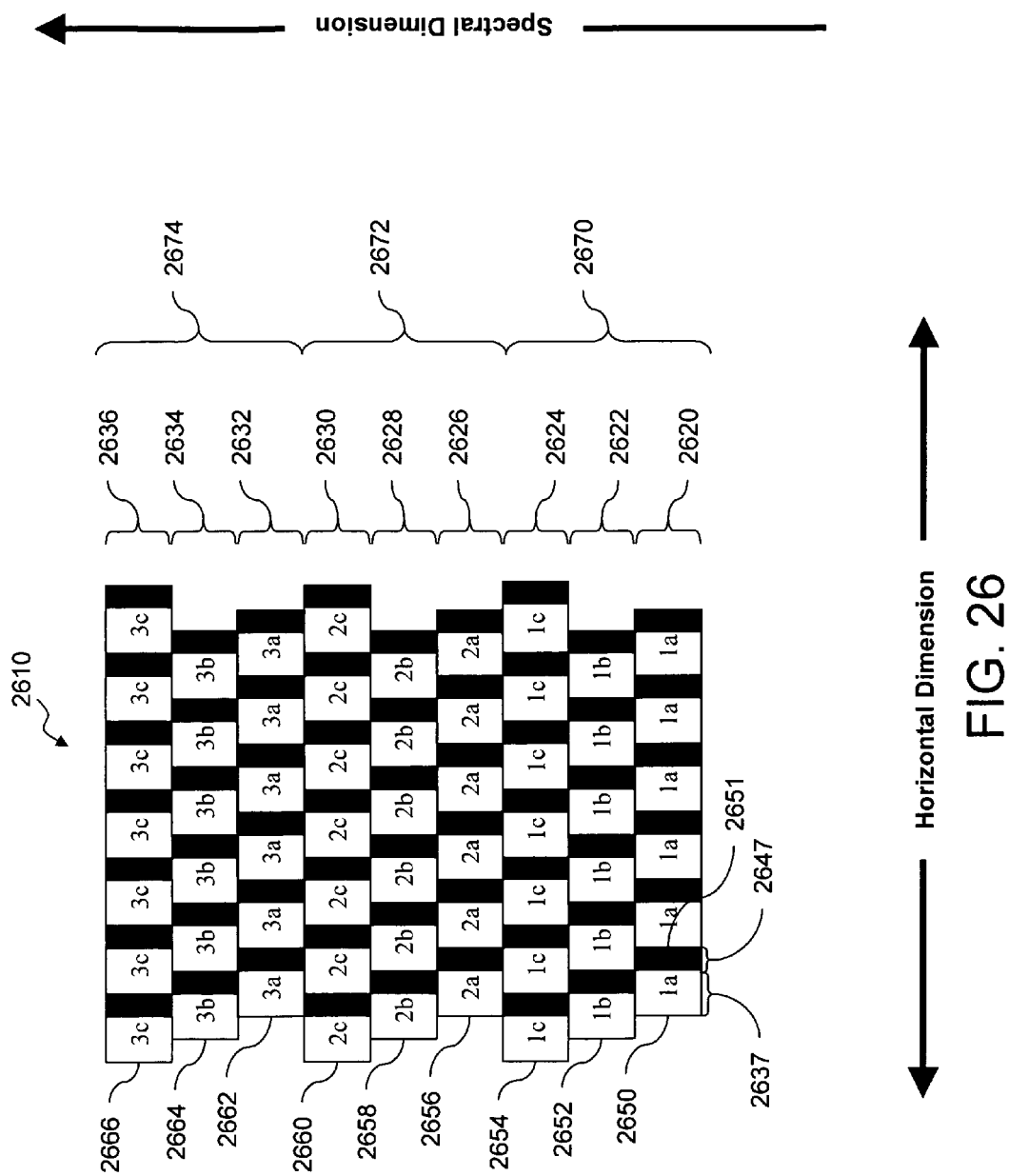
FIG. 26 shows the technique of row staggering based on the use of masked pixels to enhance the horizontal pixel image density according to the present invention.
Figure 27:
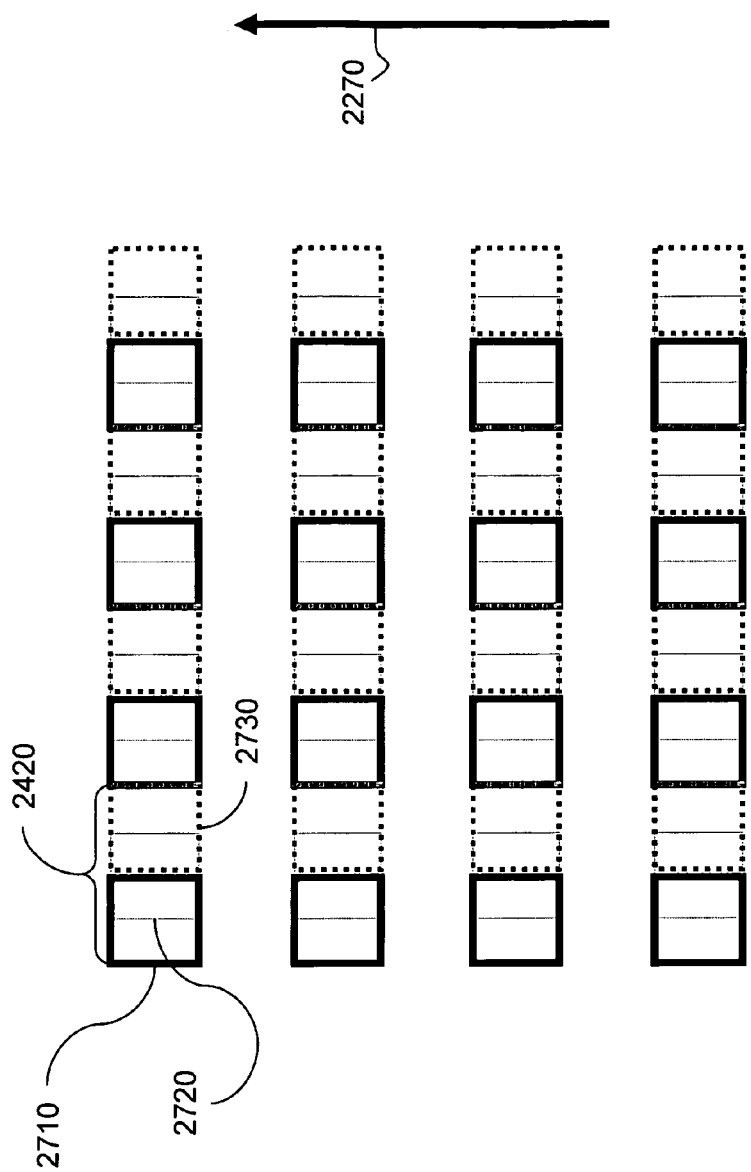
FIG. 27 illustrates another method of enhancing the horizontal pixel image density.

One limitation of simply over-sampling as described above is that there is no increase in the measurement spot density in the horizontal direction. To mitigate this problem, two-dimensional imager 8 of system 100 is replaced with a two-dimensional imager having a plurality of staggered rows of masked pixels that can be used like a single horizontal row with a higher pitch density. Preferably, each pixel is masked on a single side, as described above and using known methods. Adjacent rows are offset by the width of the mask. An example of a two-dimensional imager with staggered rows is shown in FIG. 26, which shows a portion of two-dimensional imager 2610 having a three-fold increase in measurement spot density in the horizontal direction. In use, pixels disposed along the horizontal direction correspond to a spatial dimension and pixels disposed along the vertical direction correspond to the spectral dimension, as indicated in the figure. Pixels in every third row sense light from the same physical location on wafer 1d, but at different wavelengths. The ensemble of spectral measurements at all the wavelengths available from every third vertically aligned pixels constitutes the spectrum of light reflected from the physical location on wafer 1d.

In particular, two-dimensional imager 2610 includes a pixel row 2620 that includes a pixel 2650 having a width 2637 with a mask 2651 having a width 2647. Two-dimensional imager 2610 further includes pixel rows 2622, 2624, 2626, 2628, 2630, 2632, 2634, and 2636. Pixel rows 2620, 2622, and 2624 form a row group 2670. Pixel rows 2626, 2628, and 2630 form a row group 2672. Pixel rows 2632, 2634, and 2636 form a row group 2674. Likewise, pixel row 2622 and pixel row 2624 of row group 2670 include a pixel 2652 and a pixel 2654 respectively. Pixel row 2626, pixel row 2628 and pixel row 2630 of row group 2672 include a pixel 2656, a pixel 2658, and a pixel 2660 respectively. Pixel row 2632, pixel row 2634, and pixel row 2636 of row group 2674 include a pixel 2662, a pixel 2664, and a pixel 2666 respectively.

Each pixel dimension as well as the dimensions and position of the mask on each pixel of each row is identical to that of pixel 2651 and mask 2647. Width 2647 of pixel 2651 is preferably chosen to be one third of the width of pixel 2651 so that pixels in every third row align vertically. However, it is not necessary that width 2647 be one third of the width of pixel 2651; other fractional proportions such as one half and one fourth also work, which lead to pixels in every second or fourth row respectively being aligned.

Preferably, two-dimensional imager 2610 includes 32 row groups. If each row group includes three pixel rows per row group, then 96 rows are needed to provide spectral measurements at 32 distinct wavelengths. Individual pixel rows receive light at slightly a different wavelength than adjacent pixel rows. This difference is small, and even though it does mean that physically adjacent points have 32-point spectra associated with them, there is a slight shift in wavelength from site to adjacent site. This difference is inconsequential. In practice, such differences can be accounted for by calibration procedures.

In operation, the scan speed is reduced to one third of its nominal speed. As wafer 1d moves, light from light source 3 reflects off wafer 1d and enters line imaging spectrometer 11 of system 100, where two-dimensional imager 8 has been replaced with two-dimensional imager 2610. Computer 10 receives spectral data from line imaging spectrometer 11, and generates spectral images of wafer 1d from which the film thickness of a film at desired measurement sites is determined, as described in U.S. patent application Ser. No. 09/899,383, and U.S. patent application Ser. No. 09/611,219.

Slant Scanning

Yet another approach to enhancing the density of measurements so that accurate measurements of small features can be obtained involves slant scanning, i.e. by orienting the measurement spots at an angle to the scan direction as opposed to perpendicular to it. To appreciate the need for this approach, consider that when using a scanning 1-D imaging spectrometer such as the Filmetrics STMapper system, the distance between sample spots in the direction perpendicular to the scan direction is related to the pixel-to-pixel spacing of the imaging system. As described above, imaging system 100 uses slit 5 of line imaging spectrometer 11 to define an object slit (not shown) on the wafer where measurements are made. At its simplest, slit 5 and the object slit are parallel, though this orientation is not essential. If the system is configured so that the object slit is oriented perpendicular to the scan direction, then, when simple 1:1 imaging is used (as described in the Dual-Offner sections of this document), the distance between sample spots is equal to the pixel-to-pixel spacing of the imaging system. Getting closer spacing between the sample spots generally requires complex magnifying optics, but these are expensive, and they also increase the NA and decrease the depth-of-filed at the wafer.

Figure 31:
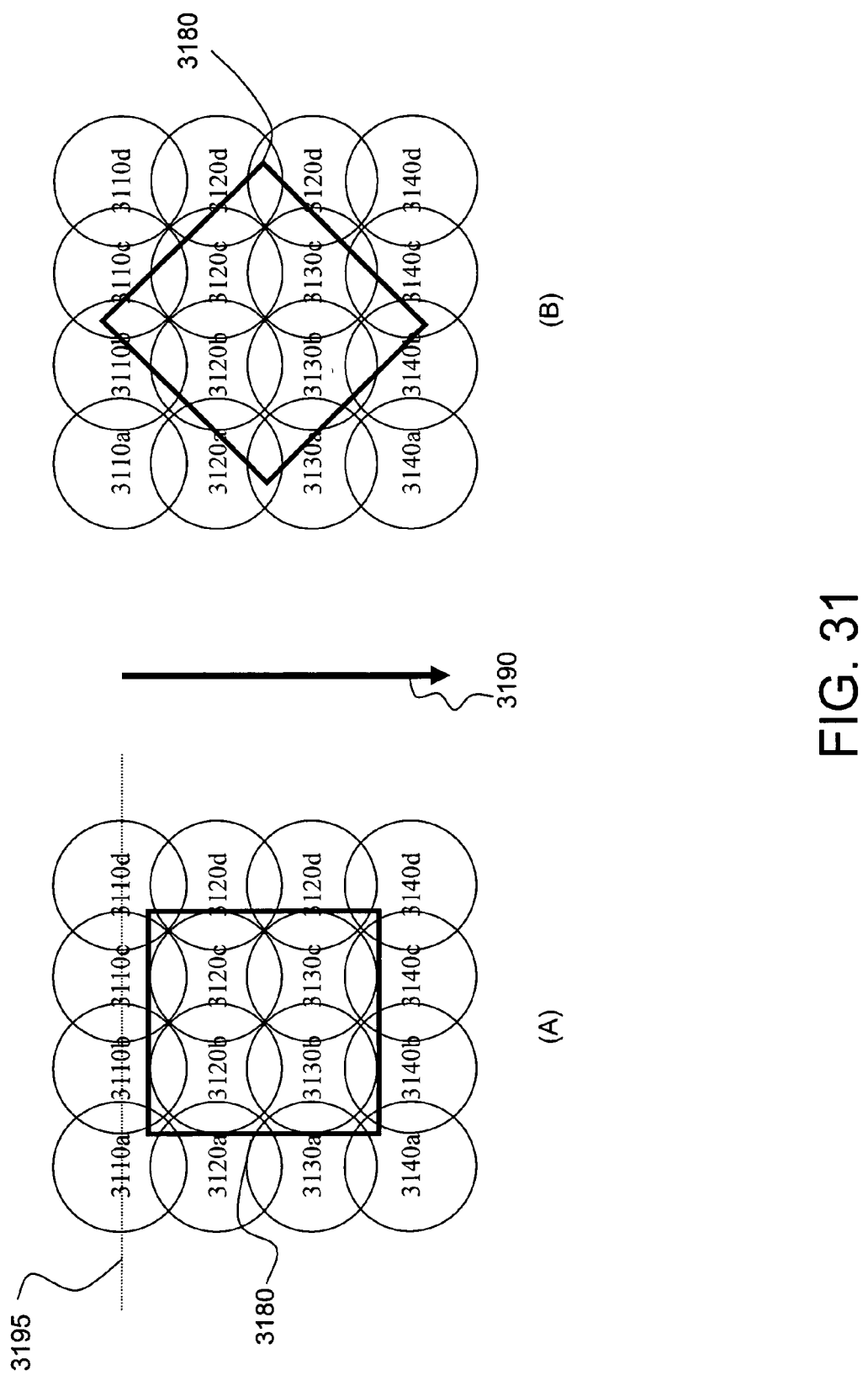
FIG. 31 shows a target on a portion of a wafer along with the measurement spots using an imaging system according to the present invention.

FIG. 31 shows a target 3180 on a portion of a wafer along with the measurement spots using imaging system 100 of an embodiment. (Note, however, that the technique of angled incidence employed in imaging system 100 is not necessary to practice slant scanning.) In the example shown in FIG. 31, each measurement spot size is 17 microns in diameter (due to pixel size and imaging optics effects), and target 3180 is a square having an edge dimension of 30 microns. Imaging system 100 is oriented such that slit 5 acts as an aperture stop that defines the object slit that is perpendicular to the scan direction. The scan direction is from top to bottom, and is designated by arrow 3190. Operation of imaging system 100 yields a series of rows of measurement spots, where each row includes a plurality of measurement spots that are aligned with the object slit. FIG. 31(A) further shows a portion of each of four such rows: a row 3110 that is obtained first, then a row 3120, a row 3130, and a row 3140, which is obtained last. Specifically, these rows include measurement spots 3110a–3110d, measurement spots 3120a–3130d, measurement spots 3130a–3130d, and measurement spots 3140a–3140d. The object slit has a midpoint about which lie the measurement spots. A representative midpoint is designated in FIG. 31(A) by dotted line 3195. FIG. 31(A) shows an optimal arrangement of spots, with successive rows of spots covering target 3180. Four measurement spots fall entirely within target 3180: measurement spot 3120b, 3120c, 3130b, and 3130c. However, in general, the rows cannot be aligned so exactly with the features on the wafer. In a worst-case scenario, which is shown in FIG. 31(B), target 3180 is at a 45-degree angle to the object slit to which rows 3110, 3120, 3130, and 3140 are aligned, and none of the measurement spots fall entirely within target 3180. With only portions of some of the measurement spots falling on feature 3180, there is significant potential for the ensuing calculations of film properties such as film layer thickness to be prone to error.

To solve this problem, line imaging spectrometer 11 of imaging system 100 is rotated about optical axis 31 so that slit 5 forms an object slit that is no longer perpendicular to scan direction 3190. Though rotating line imaging spectrometer 11 by any angle greater than 0 degrees and less than 90 degrees enhances the density of measurement spots, angles near 0 degrees offer only modest enhancement and angles near 90 degrees lead to significant measurement spot overlap and a need for multiple scans that decrease throughput. Optimal results depend on the spot size, the spot pitch, and the minimum feature size. One example orientation involves line imaging spectrometer 11 being rotated so that the object slit forms an angle of approximately 45 degrees to the scan direction. With this orientation, the effective center-to-center distance between the measurement locations is 70.7% of the distance between measurement spots in the direction parallel to the object slit.

Figure 32:
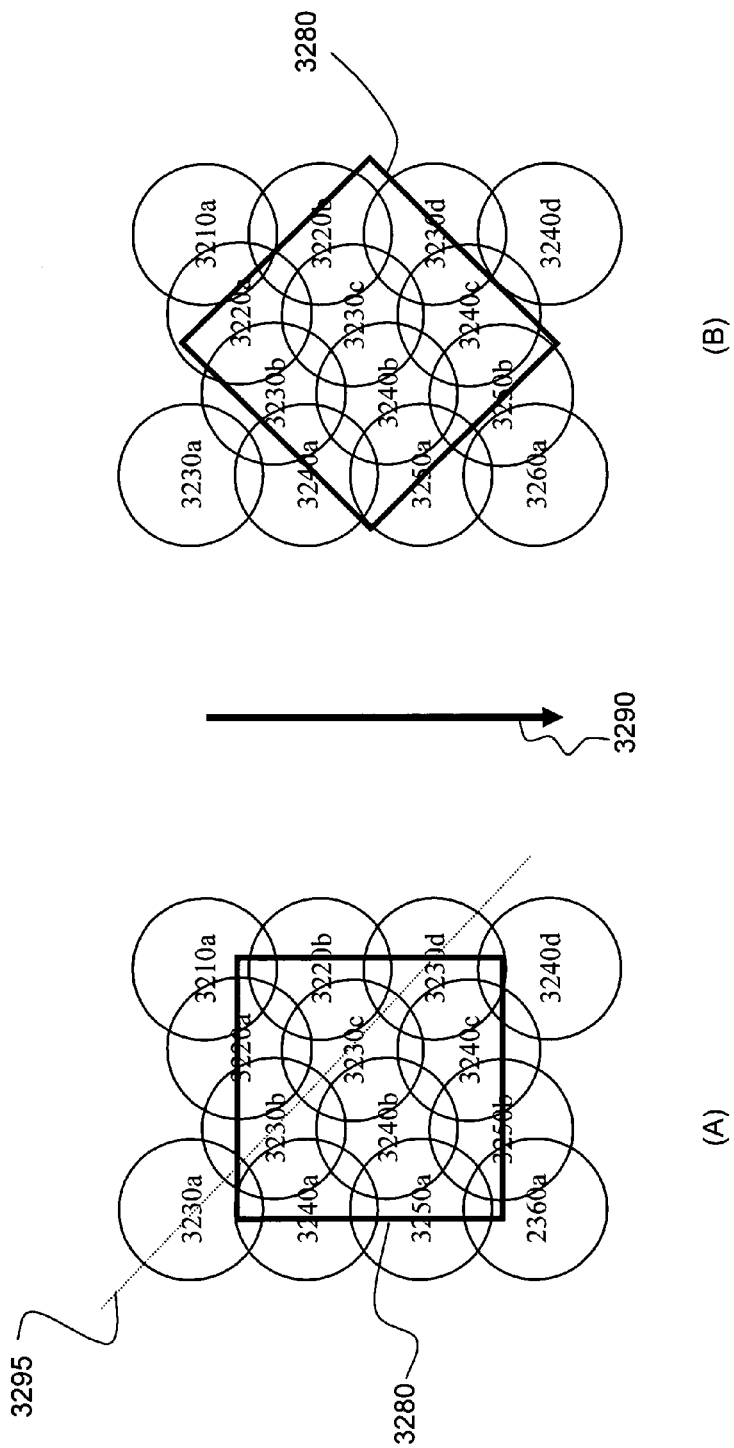
FIG. 32 illustrates a series of scan rows covering the target of FIG. 31.

FIG. 32 illustrates how rotating line imaging spectrometer 11 so that the object slit forms a 45 degree angle to the scan direction improves the quality of measured data. FIG. 32 shows a series of scan rows covering target 3280, which is aligned to scan direction 3290 in FIG. 32(A), and is oriented at a 45 degree angle to scan direction 3290 in FIG. 32(B). A representative midpoint is designated in FIG. 32(A) by dotted line 3295. In operation, imaging system 100 causes relative motion between the object slit and the wafer on which target 3280 lies so that the object slit traverses the wafer along scan direction 3290 while line imaging spectrometer 11 collects measurement data in a series of rows. First, imaging system 100 collects and records measurement data to form row 3210. Imaging system 100 then records in sequential order measurement rows 3220, 3230, and 3240. FIG. 32 shows only those portions of 3210, 3220, 3230, and 3240 that cover at least a portion of target 3280, viz., measurement spot 3210a of row 3210, measurement spots 3220a and 3220b of measurement row 3220, measurement spots 3230a–3230d of measurement row 3230, measurement spots 3240a–3240d of measurement row 3240, measurement spots 3250a and 3250b of measurement row 3250, and measurement spot 3260a of row 3260. In both FIG. 32(A) and FIG. 32(B) slant scanning leads to at least one measurement spot that falls entirely within target 3280.

For the dimensions of the example shown in FIG. 32, i.e., 17 um measurement spots and a target having an edge dimension of 30 um, two measurement spots fall within the target. In general, the number of measurement spots that fall within the target depends on the size of the target and on the measurement spot size. However, the use of slant scanning significantly increases the probability that a measurement spot falls entirely within a given target, which is very important because having a measurement spot fall entirely within a target means that the detected signal is much easier to analyze, regardless whether the detected signal is an optical reflectance signal or an ellipsometric signal. Superficially, it might appear that by reducing the number of measurement spots that fall entirely within the target, as shown by FIG. 31(A) versus FIG. 32(A), overall measurement quality declines. And, while four measurement spots on a target is better than only one, using slant scanning to obtain at least one measurement on a target represents a significant improvement because valid measurements can be obtained on targets that otherwise could be erroneous due to signal distortion from film stacks adjacent to the target. An additional advantage of slant scanning is that it effectively decreases the minimum feature size of a structure that can be measured.

It should be noted that the benefits of slant scanning depend on the relative non-perpendicular motion between the object slit and the wafer. Equivalently, it can be said that the benefits of slant scanning depend on the relative non-perpendicular motion between the wafer image and the detector, i.e., it comes about when there is a motion component of the wafer image presented to the slit 5 that is parallel to the slit 5, in addition to the motion component perpendicular to the slit 5.

Wafer Paddle Motion Damper

The process of acquiring high-speed, high-density reflectance data from a patterned wafer involves sensing light reflected from the surface of the patterned wafer. Since the wafer must move relatively to light source 3 and line imaging spectrometer 11, there is opportunity for such relative motion to degrade the sensed reflectance due to increased measurement area. Typically, such unwanted motion is in a direction transverse to the X direction 12.

Figure 28:
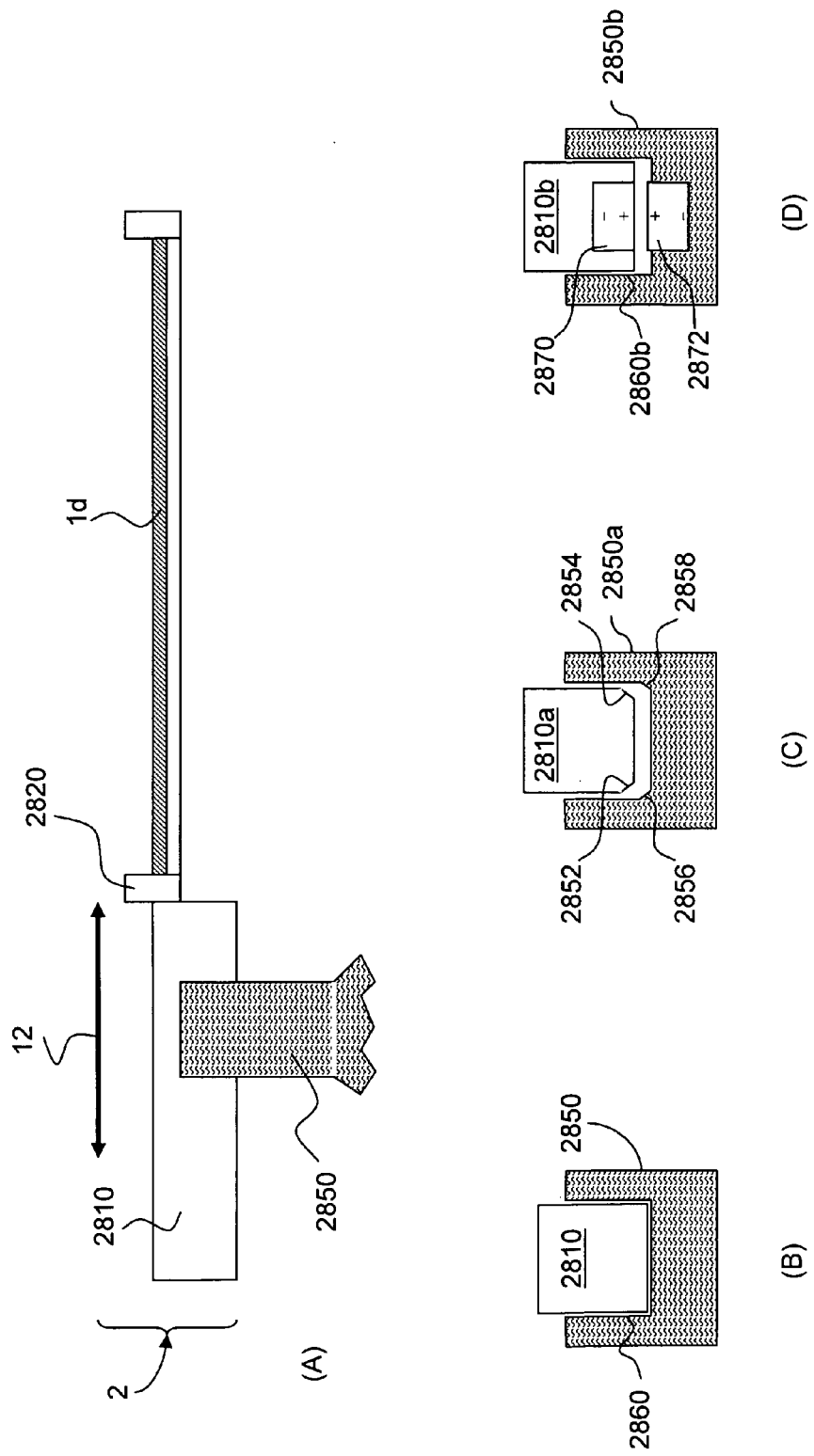
FIG. 28 shows a wafer paddle motion dampening system.

To suppress such undesirable motion an embodiment provides for a mechanism that reduces this motion. As shown in FIG. 28(A), platform 2 of system 100 further includes an arm 2810 to which a wand 2820 is mechanically attached. Wand 2820 serves to secure wafer 1d. In addition, platform 2 further includes a fixture 2850 that serves to limit unwanted motion while simultaneously allowing wafer 1d to be translated in the X direction 12 upon command from computer 10. FIG. 28 shows three exemplary ways limit unwanted motion.

FIG. 28(B) shows fixture 2850 in cross section, and in particular shows a groove 2860 that has been formed in fixture 2850. Groove 2860 is formed to conform to the shape of arm 2810 so that as computer 10 causes translation mechanism 53 to move wafer 1d, arm 2810 moves along fixture in the X direction 12. Motion in directions transverse to the X direction 12 is suppressed by groove 2860 and by slight downward pressure applied by translation mechanism 53 to keep arm 2810 in groove 2860.

Though groove 2860 is shown as being rectangular, a wide variety of other shapes also work provided that they conform to the shape of arm 2810. Example cross-sectional shapes include round, triangular, etc. In practice, only nominal shape conformality is needed: so long as at least two portions of groove 2860 are present that present stable supporting points that limit the transverse motion of arm 2810 in groove 2860, the objective of stabilizing the motion of wafer 1d is satisfied. The use of Teflon™ or wheels or bearings can also be used to reduce the sliding friction.

FIG. 28(C) shows a variation on the embodiment shown in FIG. 28(B) wherein arm 2810 has been modified to include a beveled edge 2852 and a beveled edge 2854, thus forming arm 2810a. Fixture 2850 has been likewise modified to include a beveled edge 2856 and a beveled edge 2858 that match beveled edges 2852 and 2854 respectively. The addition of these beveled edges further restricts translational motion while facilitating the ability of translational mechanism 53 to position arm 2810 within groove 2860 of fixture 2850.

FIG. 28(D) shows yet another way to stabilize transverse motion. An arm 2810b is formed by modifying arm 2810 to include a magnet 2870 disposed substantially within arm 2810c, as shown in FIG. 28(D). Magnet 2870 is oriented so that one pole, designated with a "+" in FIG. 28(D), is oriented away from arm 2810b. A fixture 2850b is formed by disposing a magnet 2872 within fixture 2850b so that magnet 2872 is flush with the surface of a groove 2860b, as shown in the figure. Magnet 2872 is oriented so that one pole, designated with a "+" in FIG. 28(D), is oriented toward arm 2810b. Essential to the operation of this embodiment is that like poles face each other so as to form a magnetic bearing.

In operation, translation mechanism 53 presses arm 2810b into groove 2860 and the opposing force induced by the close proximity of like poles in magnets 2870 and 1872 along with the structure of groove 2860b suppresses transverse motion.

Considerable variations on the embodiment shown in FIG. 28 are possible. The placement of additional pairs of magnets in the sidewalls of groove 2860b with like poles facing each other further stabilizes transverse motion. In addition, placing pairs of magnets in groove 2860b with opposite poles facing each other can be used advantageously to provide an attractive force. Such a construct, in combination with pairs of magnets with like poles facing each other, can be used to draw arm 2810b into groove 2860b, yet keep arm 2810b from actually contacting groove 2860b due to the magnetic bearing effect. This combination adds further stability against transverse motion.

The magnetic fields necessary to accomplish such stabilization are small. Likewise, so too are the relative speeds, viz., 40 mm/s. Thus, any induced currents are small and unlikely to cause damage to devices being formed in wafer 1d, especially since wand 2820 is typically made from non-conducting materials such as Teflon™ (or is otherwise electrically isolated from arm 2810).

Looking Thorough a Viewport

Embodiments described herein further provide enhanced visibility of wafer 1d when using system 101 in FIG. 3. In the absence of specific design, implementing viewport 18 with a bi-planar glass plate, as is the practice in the art, leads to a degraded image due to wavelength dependent optical path length differences (dispersion) as light refracts through viewport 18. Coating viewport 18 with an AR coating is not sufficient to solve the problem. To overcome this problem, viewport 18 is treated as an integral component of the optical elements used in system 101, and the optical design parameters of lens assembly 4, and lens assembly 6 if necessary, are adjusted to compensate for the dispersion in viewport 18. Thus, designing lens assembly 4 so that is takes into account the optical effects of viewport 18 can result in non-degraded images. Such design parameters can be optimized using commercially available software such as Zemax (ZEMAX Development Corporation, San Diego, Calif.).

Optionally, viewport 18 can be viewed as having a top surface 18t with a curvature Rt, and a bottom surface 18b having a curvature Rb, and the design process can be performed to optimize curvature Rt of top surface 18t, and/or optimizing curvature Rb of bottom surface 18b.

Figure 29:
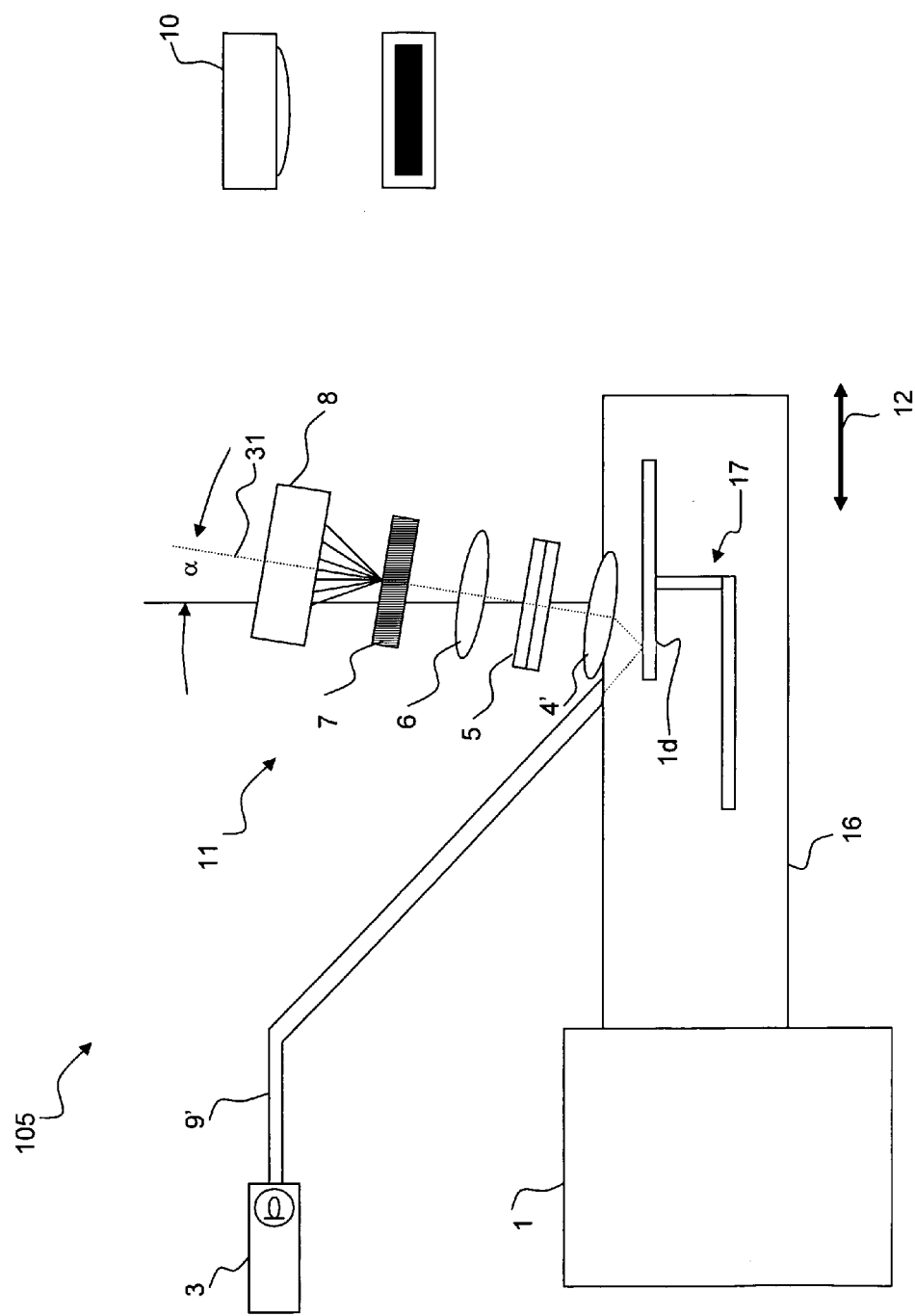
FIG. 29 shows the integration of a process chamber viewport into the optical system of the line imaging spectrometer according to the present invention.

An alternative approach is to integrate lens assembly 4 of line imaging spectrometer 11 and viewport 18 into a single piece. This approach is shown in FIG. 29, which shows system 105, which is identical to system 101 except that lens assembly 4 and viewport 18 have been replaced with lens assembly 4' that combines the functionality of lens assembly 4 and viewport 18 into a single element. Fiber bundle 9 has also been modified as fiber bundle 9' so that it is optically and mechanically coupled to transfer chamber 16. Lens assembly 4' includes one or more lenses, each having front and back surfaces having curvature that is optimized to provide a clear image of the portion of wafer 1d being illuminated by light source 3. The operation of system 105 is identical to that of system 101.

Dual-Offner

The need for obtaining measurements on very small measurement sites on wafers drives two conflicting factors. One factor is the need for sensing light from very small areas without optical contamination from nearby areas, and the second factor is the need for simple, low-cost optics. Conventional single-spot microscope-based measurement systems typically use refractive (i.e., transmissive) lens systems to provide a small, well-defined measurement spot. These lens systems are complex and expensive because the refractive index of the glass materials used to make the lenses varies with wavelength, and to be able to image a small spot over a wide range of wavelengths requires a lens system that consists of numerous (typically five or more) precision lenses that are positioned in a low-tolerance assembly.

The optical system for an imaging spectrometer is even more complex and expensive because the size of the area that they must image precisely is several orders of magnitude larger than that of a single-spot system (because each line image consists of thousands of the single-spot sized images.) The optical systems of the resolution required for the imaging micron-sized structures such as those found on ICs include three or more concave and convex mirrors that are set at precise angles to one another, which adds to the parts cost and increases the complexity of assembly due to tight alignment tolerances, which further increases system cost. In addition, such systems typically include at least one mirror element that is not spherical (i.e., that is aspherical), which adds significantly to the cost. The combination of angled positioning and aspherical mirrors lead to prohibitive cost and complexity that are inconsistent with a low-cost, high performance measurement system.

It is possible, however, to circumvent the above problems by taking advantage of two essential factors. First, the detector pixel size is comparable to the size of the measurement pads, which means that imaging with a magnification of approximately 1:1 is needed. Second, optical systems that use reflection alone eliminate the dispersion associated with refractive optics. However, the use of reflective surfaces alone is insufficient to address the above problems. Such surfaces must also minimize optical defects such as spherical aberration and coma; otherwise the problem of wavelength dispersion is replaced by another problem, viz., image distortion.

There exists a simple two-element, concentric, spherical, reflective optical system that provides 1:1 magnification and the wide-wavelength-range resolution used for an embodiment. This two-element reflective system is called an Offner system, and is described in U.S. Pat. No. 3,748,015. An Offner imaging system is a catoptic system with unit magnification with high resolution provided by convex and concave spherical mirrors arranged with their centers of curvature at a single point. Such systems use reflective optical elements configured to substantially eliminate spherical aberration, coma, and distortion. They are also free from third order astigmatism and field curvature. In practice, some flexibility in the magnification of an Offner system is possible: magnification of approximately 1.2:1 can be used without excessively degrading optical performance.

However, if used without modification, the traditional Offner imaging system simply re-images aberrant light from an object. An embodiment solves this problem with a dual-Offner system. A first Offner system replaces lens 4 of system 100, i.e. it re-images light reflected from a wafer being tested onto a slit that performs a spatial filtering function. A second Offner system replaces lens 6, and serves to re-image the spatially filtered light to the entrance aperture of a one-dimensional imaging system, which then disperses the light into its constituent wavelengths for subsequent analysis. In combination, this dual-Offner system provides near defect free image light to the one-dimensional imaging system, thus essentially stripping the recorded image of aberrations.

Figure 30:
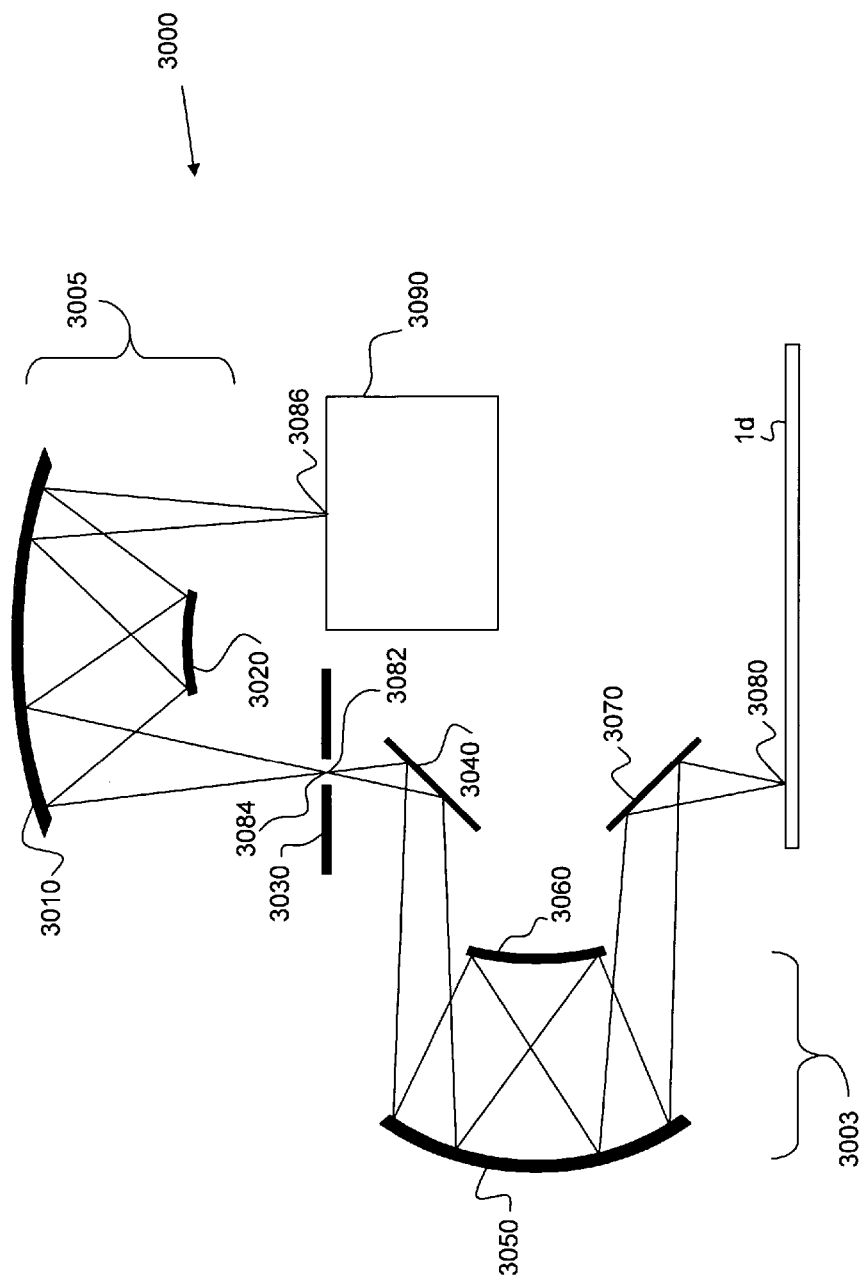
FIG. 30 shows a dual-Offner imaging system for enhancing the quality of images recorded with the line imaging spectrometer of the present invention.

FIG. 30 shows a dual Offner imaging system 3000 according to an embodiment that includes a folding mirror 3070, a first Offner group 3003, a folding mirror 3040, a slit 3030, a second Offner group 3005, and a one-dimensional imaging system 3090 having an entrance aperture.

Folding mirror 3070 and folding mirror 3030 are front surface mirrors that serve to fold the optical path of light emanating from wafer 1d to reduce the size of dual Offner imaging system 3000.

Slit 3030 is an adjustable mechanical assembly having a pair of straight edges opposing each other and adjustable to maintain a fixed distance between the straight edges.

One-dimensional imaging system 3090 has an entrance aperture that receives light. Light entering the aperture along an axis perpendicular to the direction of propagation is dispersed within one-dimensional imaging system 3190 to form a spatial-spectral image.

First Offner group 3003 includes a convex mirror 3060 and a concave mirror 3050, both of which have a radius of curvature and a focal point located at the center of curvature. Convex mirror 3060 and concave mirror 3050 are disposed within system 3000 so that their focal points are coincident. First Offner group 3003 has a focal point 3080 and a focal point 3082.

Second Offner group 3005 includes a convex mirror 3020 and a concave mirror 3010, both of which have a radius of curvature and a focal point located at the center of curvature. Convex mirror 3020 and concave mirror 3010 are disposed within system 3000 so that their focal points are coincident. Second Offner group 3005 has a focal point 3084 and a focal point 3086. Second Offner group 3005 is disposed within system 3000 so that focal point 3082 and focal point 3084 coincide within slit 3040. Focal point 3086 is disposed within system 3000 at the entrance aperture of one-dimensional imaging system 3080.

In operation, wafer 1d is positioned within system 3000 so that portions of wafer 1d that include one or more measurement test sites pass through focal point 3080 of first Offner group 3003. Mirror 3070 reflects light reflected from wafer 1d at focal point 3080 and directs it toward concave mirror 3050 whereupon it is reflected toward convex mirror 3060. The light then undergoes a reflection back toward concave mirror 3050, and in so doing it starts to converge. The light reflects off concave mirror 3050 in a second reflection from this mirror. Subsequent to this reflection, the light reflects off folding mirror 3040, as it converges to focal point 3082. The blades of slit 3030, having been adjusted to approximately 10 um of separation, spatially filter the light passing through slit 3030. Once passing through focal point 3082 (and focal point 3084), the light diverges toward concave mirror 3010 of second Offner group 3005, which reflects the light toward convex mirror 3020. Upon reflection from convex mirror 3020, the light undergoes a second reflection from concave mirror 3010 before converging to focal point 3086. One-dimensional imaging system 3090 then receives the light and forms a spatial-spectral image of wafer 1d.

The lack of refractive optical elements in first Offner group 3003 and in Offner group 3005 means that system 3000 is particularly well suited for use with UV light.

Double-Pass Single-Offner

The use of two Offner systems allows tremendous improvements in signal quality as it provides nominal 1:1 magnification and wide-wavelength range resolution with substantially eliminated spherical aberration, coma, and distortion and zero third order astigmatism and field curvature. However, the requirement of two such systems increases the overall system cost and system size. When integrating a metrology system into a wafer processing tool, it is highly desirable to reduce the size of the metrology system since space in the processing tool is limited. With a dual-Offner system both Offner systems perform substantially the same operation, viz., they perform a very high quality re-imaging process. What is needed is a way to eliminate the requirement of the second Offner system while retaining the functionality of a dual-Offner system. An embodiment accomplishes these objectives while requiring only a single Offner system.

Figure 33:
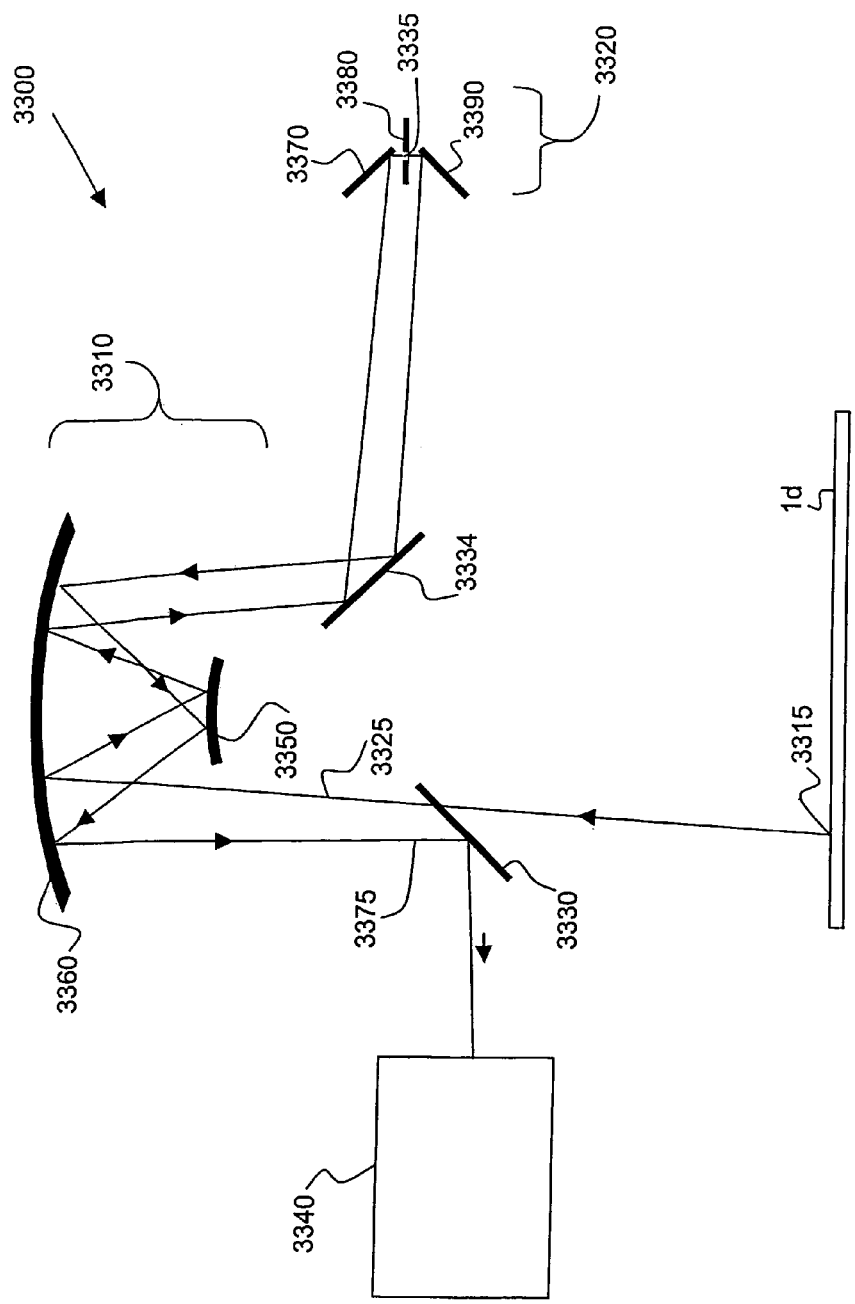
FIG. 33 shows one embodiment of a double-pass Offner system according to the invention.

FIG. 33 shows a specially configured image detection system 3300 that includes an Offner system 3310, a retro-reflector assembly 3320, a beam splitter 3330, a mirror 3334 and a detector 3340.

Offner system 3310 includes a convex mirror 3350 and a concave mirror 3360, both of which have a radius of curvature and a focal point located at the center of curvature. Convex mirror 3350 and concave mirror 3360 are disposed within system 3300 so that their focal points coincide. Offner system 3310 has a focal point 3315 arranged within system 3300 to coincide with the plane of wafer 1d, and a focal point 3335 positioned within retro-reflector assembly 3320. Offner system 3310 has a first aperture 3320 that receives light emanating from focal point 3315, and from the immediate vicinity of focal point 3315. Offner system 3310 also has a second aperture 3330 that receives light emanating from focal point 3335, and from the immediate vicinity of focal point 3335.

Retro-reflector assembly 3320 includes a mirror 3370, a slit 3380, and a mirror 3390. Both mirror 3370 and mirror 3390 are front surface mirrors that serve in combination to redirect incident light from Offner system 3310 back in the direction of Offner system 3310. Mirror 3370 is disposed within system 3300 between concave mirror 3360 and focal point 3335 so that light exiting from concave mirror 3360 and passing through second aperture 3330 of Offner system 3310 strikes mirror 3370 before converging at focal point 3335. Upon reflection from mirror 3370, light propagates to slit 3380, which has two blades that allow the slit to serve as a system aperture. Slit 3380 is positioned so that focal point 3335 is between the blades of the slit. Thus, slit 3380 restricts the light that eventually reaches detector 3340 to light from a desired portion of wafer 1d. Mirror 3390 is disposed within system 3300 between concave mirror 3360 and focal point 3335 so that light passing through slit 3380 is reflected back through second aperture 3330 of Offner system 3310 and to concave mirror 3360.

Detector 3340 is a one-dimensional spectral imaging system having an entrance aperture that includes diffraction grating 622 and two-dimensional imager 624.

The elements of system 3300 are arranged along an optical path beginning with focal point 3315 and extending sequentially through beamsplitter 3330 to Offner system 3310 to mirror 3334, and then to retro-reflector assembly 3320, back to Offner system 3310, and then to beamsplitter 3330 and then to detector 3340.

In operation, a portion of light emanating from wafer 1d near focal point 3315 passes through beamsplitter 3330, and enters Offner system 3310 through first aperture 3320. Light emanating from wafer 1d that reflects from beamsplitter 3330 is lost from the system. Light entering Offner system 3310 through first aperture 3320 undergoes a first reflection from concave mirror 3360, a second reflection from convex mirror 3350, a third reflection from concave mirror 3360. This sequence of reflections constitutes a first pass through Offner system 3310. Light undergoing the third reflection within Offner system 3310 at the completion of the first pass through Offner system 3310 then exits Offner system 3310, whereupon it undergoes reflection first by mirror 3334, and then by retro-reflection assembly 3320. This reflection within retro-reflector assembly involves the light first reflecting off mirror 3370, being filtered by slit 3380, and then reflected by mirror 3390 back towards mirror 3334, whereupon it propagates into second aperture 3330 of Offner system 3310. Light entering second aperture 3330 of Offner system 3310 completes a second pass through Offner system 3310 by undergoing a reflection from concave mirror 3360, a reflection from convex mirror 3350, and another reflection from concave mirror 3360. Upon completing the second pass through Offner system 3310 as a result of these three reflections, the light exits Offner system 3310, and reflects off of beamsplitter 3330 before being sensed by detector 3340.

Figure 34:
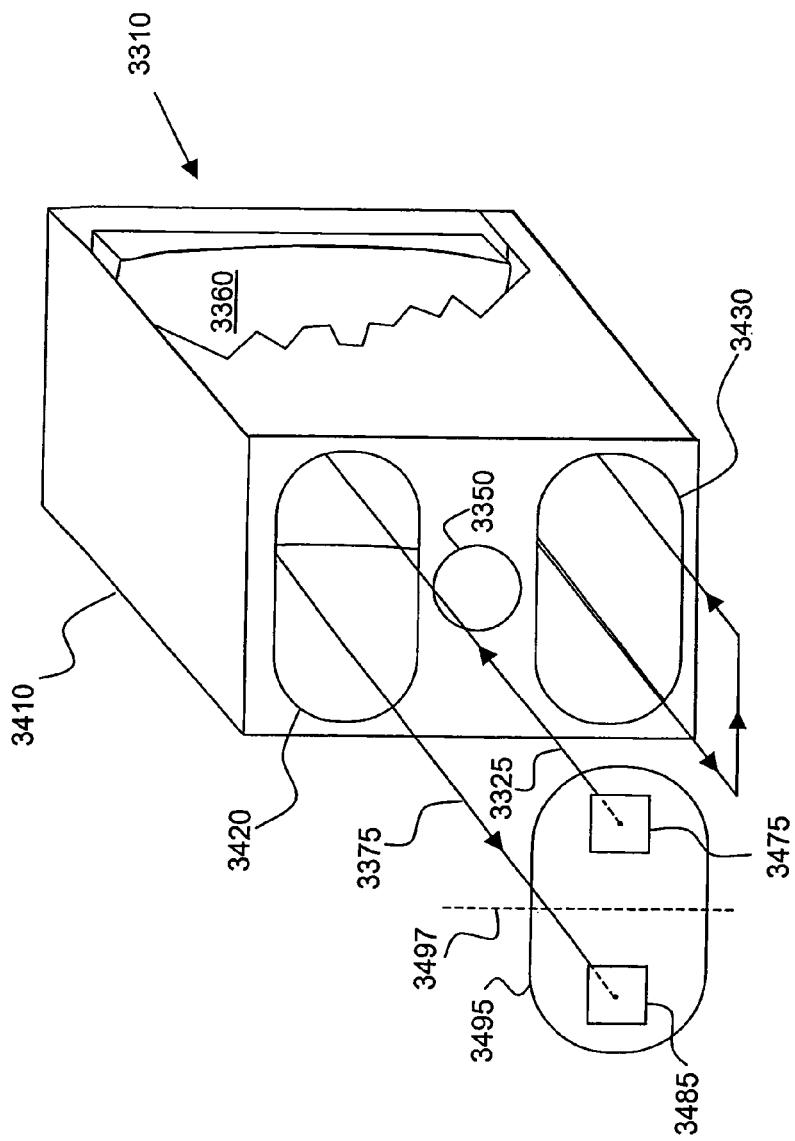
FIG. 34 shows a perspective view of the Offner system of FIG. 33.

FIG. 34 shows a perspective view of Offner system 3310 that further includes a housing 3410 and shows first aperture 3420, and second aperture 3430. For clarity, one face of housing 3410 has been rendered in cut-away format to facilitate viewing the inside of housing 3410. Housing 3410 has a first face having an interior portion to which is attached convex mirror 3350. First aperture 3420 and second aperture 3430 are formed in the first face on opposite sides of convex mirror 3350. Housing 3410 also has a second face opposing the first face. The second face has an interior portion that opposes the interior portion of the first face, and to which concave mirror 3360 is secured. FIG. 34 also shows light beam 3325 passing through first aperture 3420. For clarity, retro-reflection assembly 3320 has been omitted, but the functionality of light passing out of Offner system 3310 through second aperture 3430 and returning through this aperture is shown. Light exiting first aperture 3420 after undergoing the second pass through Offner system 3310 forms light beam 3375.

Referring to FIG. 33, beamsplitter 3330 serves to redirect a portion of light incident upon it from Offner system 3310 towards detector 3340. Beamsplitter 3330 can be replaced with a mirror provided that the mirror is positioned to reflect light exiting from first aperture 3420 of Offner system 3310 toward detector 3340, but also so it does not block light emanating from focal point 3315 that is propagating towards first aperture 3420 of Offner system 3310. One way to realize this objective is to restrict the light emanating from wafer 1d around focal point 3315 to only a fraction of the imaging area of the Offner.

FIG. 34 shows how such restriction can be accomplished in practice. In particular, FIG. 34 shows a field 3495, which represents the focal plane in which focal point 3315 lies. Light emanating from field 3495 enters first aperture 3420, and includes light from a desired object area 3475 of wafer 1d. Upon following optical path 3325 into Offner system 3310, undergoing retro-reflection via mirrors 3370 and 3390, the light exits Offner system 3310 along optical path 3375 to yield an image 3485. In the absence of a reflector, image 3485 would end up near object area 3475. However, one attribute of an embodiment is that the combination of Offner system 3310 and retro-reflector assembly 3320 is that image 3485 is displaced from object area 3475. By positioning a mirror in optical path 3375 and along dotted line 3497, image 3485 is deflected toward detector 3340. With the apparatus of an embodiment, field 3495 is approximately 26 mm, slit 3380 limits light from object area 3475 to approximately 5 mm×100 um, and detector 3340 is designed to image an area approximately 5 mm in diameter, which allows the apparatus of an embodiment to sense image 3485. Thus, the arrangement of a single Offner system in combination with a retro-reflector assembly and a beamsplitter (or mirror) allows a significant reduction in overall footprint by eliminating the requirement of a second Offner system.

In addition to reductions in system size and cost, a further benefit of the dual-Offner configuration is that some of the optical non-idealities introduced by the first pass through the Offner can be significantly reduced (aka reversed) by the second (return) pass through the same Offner. This is especially true when care is taken that the first and second passes through the Offner take essentially the same, but reversed, path. This quality is aided by the telecentric nature of the Offner, and can be helpful in correcting some of the real-world errors in implementing the Offner system.

Scanning System with Distance Sensor

One-dimensional spectral imaging systems operate by causing relative motion between a line imaging spectrometer and a wafer being measured, recording the spectral reflectance of a series of one or more spectral line images from one or more portions of the wafer that form spectral images, and analyzing the spectral images corresponding to these portions to deduce images of film layer properties such as film layer thickness within the portions. For a one-dimensional spectral imaging system to provide optimum feature resolution within a given object area requires that the object area be positioned well within the depth of field of the imaging system, preferably very near to the focal point of the system.

During operation, two primary factors cause the surface of the wafer to be displaced that degrade the performance of the one-dimensional spectral imaging system. One factor pertains to imperfections of the wafers, and the second factor pertains to imperfections in translation mechanisms used to position wafers.

As wafers are undergo each manufacturing step, layers of materials are added or added and selectively removed. Each layer has intrinsic stresses due to the material deposited and the nature of deposition. Intimate contact between adjacent layers of differing materials leads to additional stresses. These stresses vary during the manufacturing process with each process step as additional layers are modified through film layer deposition, etching, polishing, etc. The difference between the stresses on one side of the wafer and the opposing side cause the wafer to bow and/or warp. In addition, wafers are not manufacturer perfectly flat, and also gravity and wafer chucks can cause wafers to bow. What is needed is a way to accommodate wafer bowing and warping so that the object area remains within the depth of field of the line imaging spectrometer.

Imperfections in positioning mechanisms used to provide relative motion between the wafer and the line imaging spectrometer provide an additional source of defocusing. The extent of such imperfections depends in part on the quality of the positioning mechanisms used, but usually there is a significant increase in cost associated with reducing displacement tolerance of positioning mechanisms.

The combined sum of displacement arising from wafer warping and bowing as well as from positioning mechanisms amounts to hundreds of microns and can be a significant cause of defocusing. These variations are a slowly varying function of position across the wafer. Such defocusing degrades the quality of the resulting images, which can significantly affect the minimum feature size that can be measured. What is needed is a way to compensate for such defocusing, especially while acquiring one-dimensional spectral image data.

Since wafer warp and bow cannot be eliminated and some positioning tolerance of positioning mechanisms always exists, systems that require precise positioning of wafers must accommodate imperfections in wafer planarity and tolerance of positioning mechanisms.

For high NA systems, such as microscope objective based systems having a NA of approximately 0.75, the displacement tolerance afforded by the depth of field of such systems is on the order of a few microns. Such a small depth of field means that such systems require expensive, high-precision translation mechanisms to keep object areas within focus. What is needed is a way to obtain high-precision automatic focusing at low to moderate cost.

An embodiment solves these problems by integrating a distance sensor into a one-dimensional spectral imaging system, and using distance measurements obtained with the distance sensor to adjust the one-dimensional spectral imaging system so that image resolution is optimized. Given the information on the distance from the sensor to the wafer there are several ways the spectral images can be optimized. One way is to adjust the height of the wafer within the system. A second way is to adjust the line imaging spectrometer height. A third way is to adjust the focal distance within the imaging system. The first two ways are substantially similar, and it is well known in the art how to implement the other if one is understood. The third approach requires more discussion.

Figure 35:
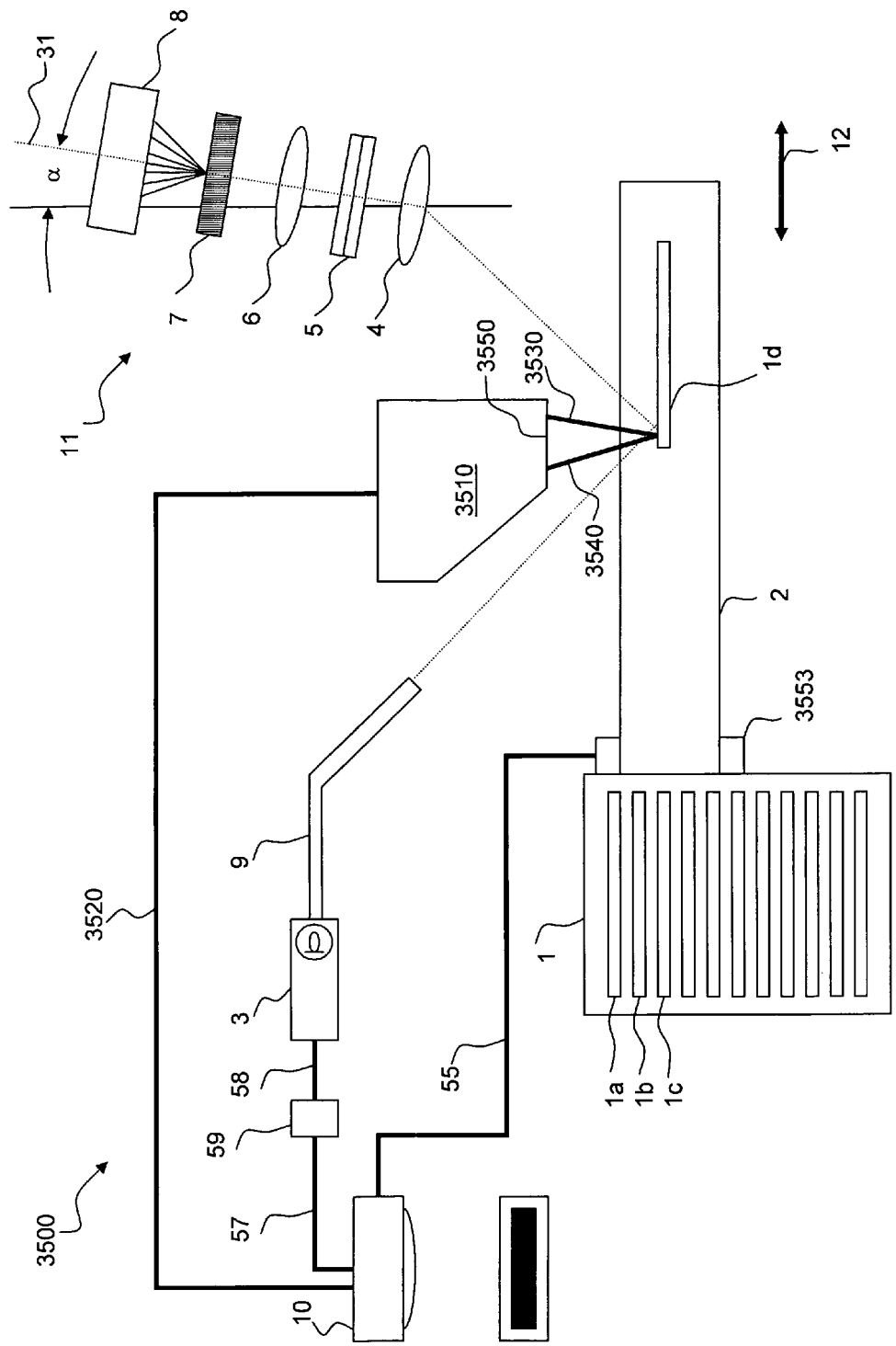
FIG. 35 shows one embodiment of a system according to the invention having an integral distance sensor for adjusting the height of a wafer.

With respect to optimizing image resolution by adjusting the wafer height, FIG. 35 shows a system 3500 for dynamically optimizing image resolution by adjusting the height of a wafer being measured. System 3500 is identical to system 100, except for the addition of a distance sensor 3510 that is electrically connected to computer 10 using a connection 3520. In addition, translation stage 53 is replaced with translation stage 3553.

Translation stage 3553 serves to position wafer 1*d* within a three dimensional volume within platform 2. Motion in two of these dimensions allows light imaging spectrometer 11 to scan wafer 1*d*. Motion in the third dimension determines the wafer height, which affects measurement spot sizes on wafer 1*d*. Those of skill in the art will appreciate that motion in the third dimension can also be accomplished by mounting light imaging spectrometer 11 to a translation stage.

Line imaging spectrometer 11, which has a nominal focal length, is oriented at small angle α, and is designed to have a numerical aperture of 0.10 or less, which allows it to operate with a depth of field of approximately 25 to 50 microns. Line imaging spectrometer 11 is disposed within system 100 so that it senses light from a desired line area on wafer 1*d*.

Distance sensor 3510 serves to provide measurements of the relative height of wafer 1*d*. Distance sensor 3510 can be implemented using any of many commercially available distance sensors, including an Acuity Research AccuRange200-6M available from Schmitt Measurement Systems, Inc. (Portland, Oreg.). This distance sensor is modestly priced, which significantly reduces overall system cost. Distance sensor 3510 includes a face 3550, a laser (not shown) that emits a light beam 3530 from face 3550, and a light detector (not shown). The light detector senses a reflected light beam 3540, which is a portion of the light emitted from the laser that reflects from wafer 1*d*. The sensor can be set at an angle so to measure distances to both diffuse and specular surfaces. The light detector is a line image detector within distance sensor 3510 that creates a distance signal that is communicated to computer 10 via connection 3520. In addition, distance sensor 3510 has a standoff distance and a span. The span is the working distance over which accurate measurements can be obtained, and is 6.35 mm for the AccuRange 200-6M. The standoff distance is 21 mm, and extends from distance sensor 3510 to the mid-point of the span. Preferably, the surface of wafer 1*d* intersects the mid-point of the span. The AccuRange 200-6M has a resolution of 1.9 um, which allows it to provide distance measurements so that wafer 1*d* can by precisely positioned at the focal point of one-dimensional spectral imager 11 to within less than 2 um. The light detector of distance sensor 3510 generates the distance signal at a rate of 600 to 1250 samples per second, which means that distance measurements can be accurately obtained while wafer 1*d* and line imaging spectrometer 11 undergo relative motion.

Distance sensor 3510 is disposed within system 3500 so that face 3550 opposes wafer 1*d* at a nominal distance equal to the standoff distance, and near the so that distance sensor 3510

In operation, computer 10 sends commands to translation stage 3553 that cause wafer 1*d* on platform 2 on wafer station 1 to move. As translation stage 3553 moves wafer 1*d* to a position where light from the laser within distance sensor 3510 reflects from wafer 1*d*, distance sensor 3510 generates distance signals that are communicated to computer 10. Computer 10 compares the reported distance measurements to the nominal distance, and instructs translation stage 3553 to adjust the distance between distance sensor 3510 and wafer 1*d*. These adjustments reflect the variations in wafer topology due to wafer bow and warp, as well as to fluctuations in height due to the translation mechanism within translation stage 3553. When wafer 1*d* is positioned in a desired location, computer 10 sends synchronization commands to synchronization circuit 59, which cause light source 3 to emit pulses of light that propagate fiber bundle 9 to wafer 1*d*. Computer 10 also sends configuration commands to two-dimensional imager 8 that include the integration time and a command to initiate data collection. The pulses of light emitted by light source 3 are short enough compared to the speed of wafer 1*d* that the light collected by line imaging spectrometer 11 comes from a minimally sized spot on wafer 1*d*. Furthermore, the pulses of light from light source 3 are synchronized with the integration time and the data acquisition command so that each pulse is emitted only during the integration time. One-spatial-dimension imaging spectrometer 11 in turn communicates the spectral and spatial information to the computer 10 over one or more signal lines or through a wireless interface. Spectral reflectance data is continually taken in this way while the wafer 1*d* is moved under the one-spatial-dimension imaging spectrometer by the platform 2 under the action of translation stage 53 and upon command from computer 10. During spectral reflectance data acquisition, distance sensor 3510 continues to communicate distance measurements to computer 10, which subsequently issues height adjustment commands to translation stage 3553 as necessary to accommodate defocusing during the data acquisition process. Thus, wafer 1*d* is maintained in a position that allows optimum image resolution.

Figure 36:
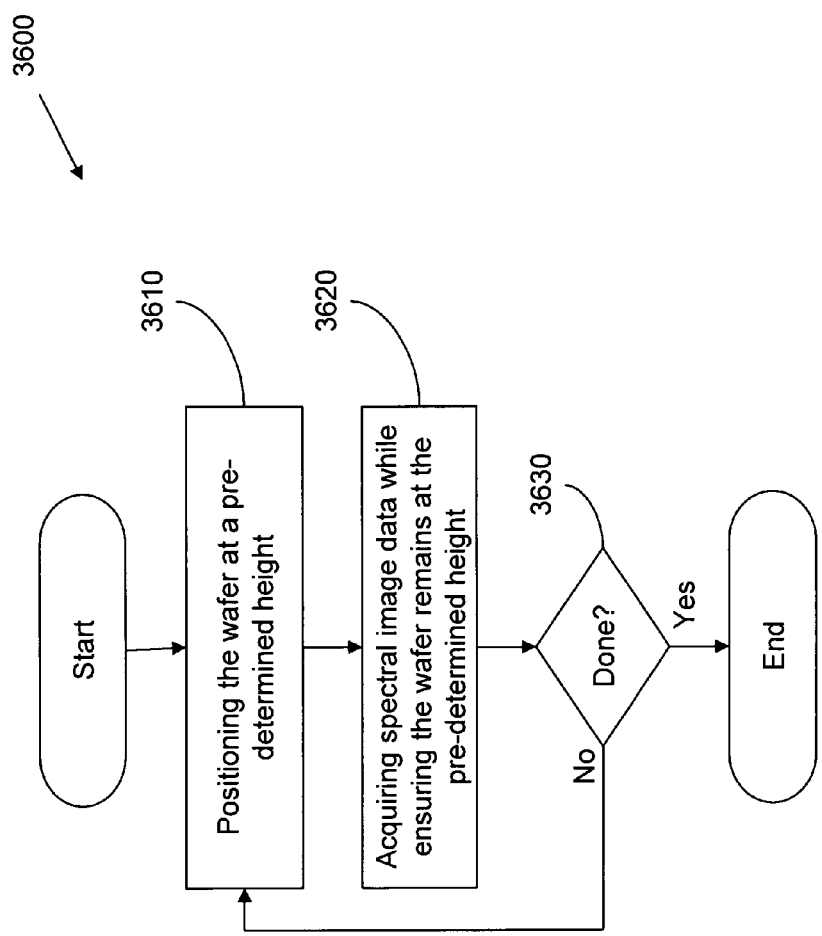
FIG. 36 shows one embodiment of a method of acquiring spectral images according to the present invention.

FIG. 36 shows a method 3600 of acquiring spectral images of wafer 1*d* while maintaining optimum feature size in the acquired spectral images.

Step 3610 involves computer 10 issuing commands to translation stage 3553 that cause translation stage 3553 to position wafer 1*d* on stage 2 beneath line imaging spectrometer 11. Step 3610 further involves distance sensor 3510 sensing the presence of wafer 1*d* by indicating an initial height and communicating the initial height to computer 10. Computer 10 then issues commands to translation stage 3553 to adjust the distance between distance sensor 3510 and wafer 1*d* to position wafer 1*d* at a pre-determined height, e.g. at the focal point of line imaging spectrometer 11. The pre-determined height has a tolerance, e.g. the focal distance of line imaging spectrometer 11 plus or minus the resolution of distance sensor 3510. In addition, step 3610 involves additional height adjustments to ensure wafer 1*d* remains at the focal point of line imaging spectrometer 11 while translation stage 3553 positions wafer 1*d* so that line imaging spectrometer 11 images a desired portion of wafer 1*d*.

Step 3620 involves system 100 acquiring spectral image data while ensuring the wafer remains at the pre-determined height. During this step, line imaging spectrometer 11 and wafer 1*d* are oriented to allow line imaging spectrometer 11 to image the desired portion of wafer 1*d*. Either before and/or during the time system 100 acquires spectral image data, computer 10 receives distance signals from distance sensor 3510, and issues commands to translation stage 3553 to adjust the position of wafer 1*d* to ensure that wafer 1*d* remains at the pre-determined height. Optionally, step 3620 omits any height adjustment and simply acquires spectral image data.

Step 3630 involves assessing whether additional spectral image data is required. If so, then the logic of method 3600 moves to step 3610 so that spectral image data at other locations on wafer 1*d* can be acquired. If not, then method 3600 terminates.

To implement the third approach, a dynamic one-dimensional spectral imaging (DODSI) system is used. The DODSI system comprises system 3500 in combination with a double pass single Offner system that has been modified to allow the retro-reflector and slit position of the double pass single Offner system to be adjusted dynamically. These adjustments allow the focal point of lens 4 and lens 5 to be adjusted in a controlled manner. Note that it is also unnecessary to replace translation stage 53 with translation stage 3553 in the DODSI system.

Figure 37:
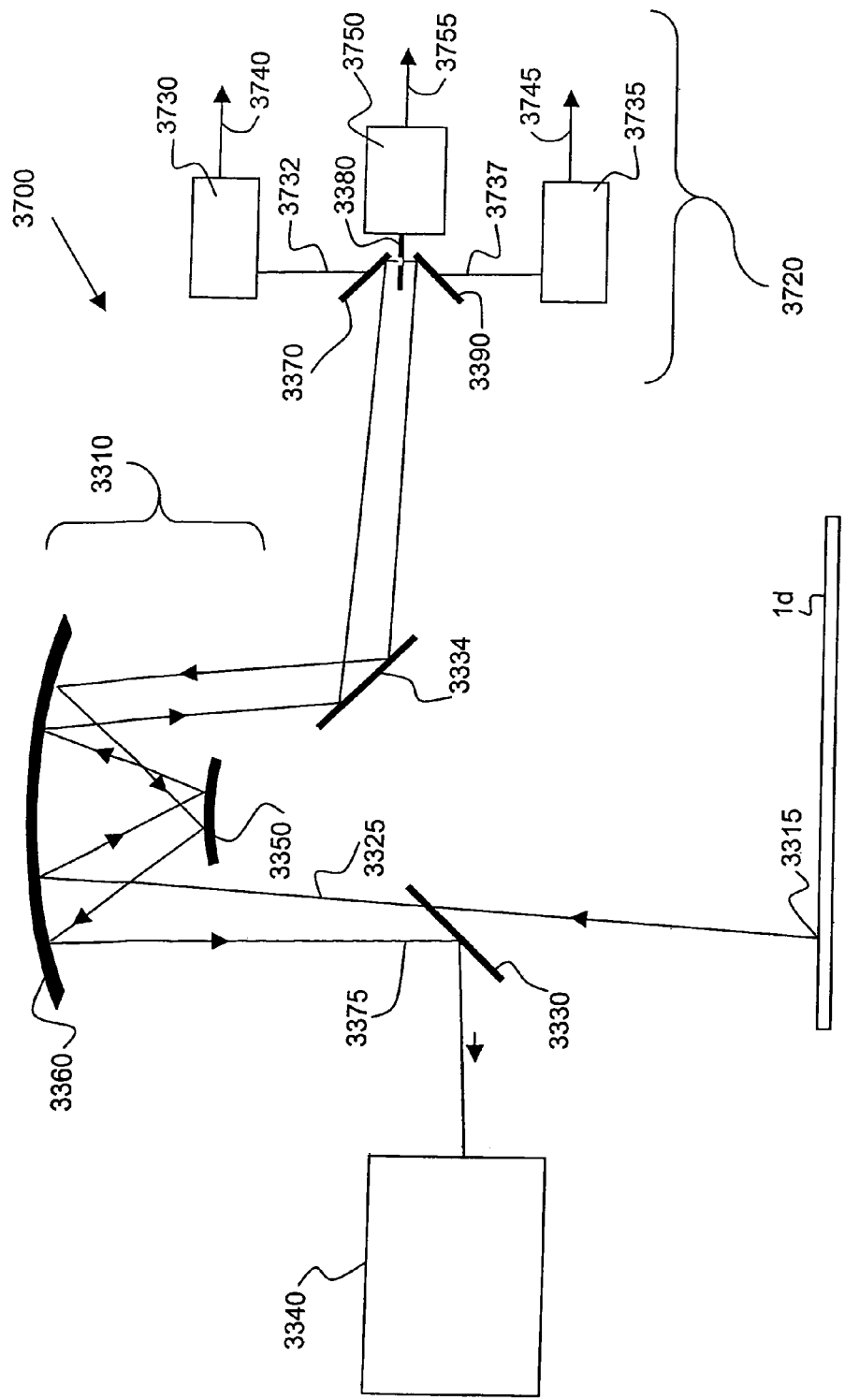
FIG. 37 illustrates another embodiment of an image detection system according to the invention.

To combine these systems, image detection system 3300 is modified to form image detection system 3700, shown in FIG. 37, by integrating line imaging spectrometer 11 into detector 3340 along with optional beam folding mirrors to reduce package size. In addition, retro-reflector assembly 3320 is replaced by an adjustable retro-reflector assembly 3720. Adjustable retro-reflector assembly 3720 is identical to retro-reflector assembly 3320 except for the addition of a motor 3730 mechanically coupled to mirror 3370 with a coupler 3332, a motor 3735 mechanically coupled to mirror 3390 with a coupler 3337, and motor 3750 that adjusts the position of slit 3380. In addition, motor 3730 and motor 3735 are electronically coupled to computer 10 via an electronic coupler 3740 and an electronic coupler 3745 respectively.

In practice, mirror 3370 and mirror 3390 can be combined into a single retro-reflecting assembly that is adjusted by a single motor under the control of computer 10. Those of skill in the art will appreciate that numerous alternative ways can be used to implement positional control of mirror 3370, mirror 3390, and slit 3380.

Operation of the DODSI system is substantially the same as that of system 3500 except that instead of computer 10 issuing commands to translation stage 3553 to adjust the distance between distance sensor 3510 and wafer 1*d*, computer 10 issues commands to motor 3730 and motor 3735 that cause the optical path length to change in accordance with the distance measurement reported by distance sensor 3510, thus adjusting the focal length of line imaging spectrometer 11. In particular, in the absence of any defocusing, distance sensor 3310 measures a distance value that defines a reference distance. In the presence of defocusing, distance sensor 3310 measures a distance that differs from the reference distance. Computer 10 calculates a difference value equal to the difference between the reference distance and the distance and issues commands to adjust the optical path length by an amount equal to this difference value. In addition, computer 10 issues commands to motor 3750 to keep slit 3380 focused onto the imager 3340.

Figure 38:
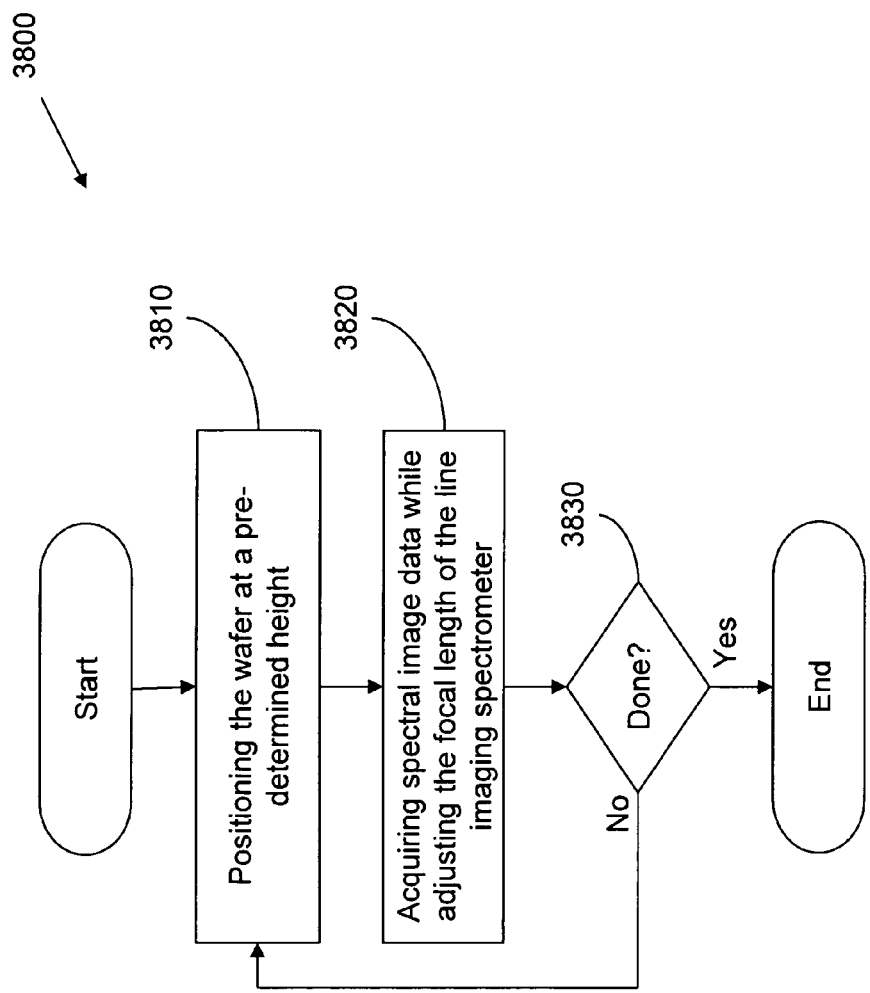
FIG. 38 shows another embodiment of a method of acquiring spectral images according to the present invention.

FIG. 38 shows a method 3800 of using the DODSI system. It is identical to method 3600, except step 3620 has been replaced with step 3820. Step 3820 involves system

100 acquiring spectral image data while adjusting the focal length of line imaging spectrometer 11 in accordance with the distance signals. In particular, the focal length is changed by the same amount that the distance measurements changes from the nominal focal length. Optionally, step 3820 omits any height adjustment and simply acquires spectral image data.

The various embodiments described herein have been described in the context of rectilinear wafer motion. Though such motion is often accomplished using linear translation stages, other mechanisms such as R-θ stages can also be used. Advantageously, R-θ stages also allow the overall system footprint of a given embodiment to be reduced compared to the system footprint using linear translation stages. Implementing system 100, system 101, system 102, system 103, system 104, or system 105 with R-θ stages involves moving one or both of optical system 11 wafer 1*d* with the R-θ stage.

It should also be clear that the methods and embodiments described herein can be used to measure film properties on all or on only a portion of a wafer or other structure having a stack of thin films.

Determining Wafer Orientation from Spectral Images

In other embodiments, systems and methods are provided for determining wafer orientation from a spectral image. This embodiment uses any of the systems and/or methods described above to obtain a two-dimensional image of a portion of a wafer surface, wherein the obtained image includes at least one spectral dimension. A spectral image contains more information than a video image obtained by conventional means. Thus, a spectral image of a wafer surface can be better analyzed to determine additional features such as wafer orientation and the position of measurement pads.

One such analysis method involves modeling the reflectance spectra as a film stack and then determining one or more film stack properties such as thickness, by varying model parameters and comparing the resulting modeled spectra to the measured spectra (as described above). The method then determines a GOF value based on the comparison. A GOF value indicates how well the model film stack represents the actual film stack. GOF values are typically assigned between 0 and 1. A perfect GOF is generally assigned a value of 1, whereas 0 represents the worst case fit.

During wafer processing, the method derives one or more properties based on the film stack (such as thickness or GOF) from the spectral image. Then, a map is generated according to the derived property or properties and compared to a previously-generated map or maps. This allows maps to be produced that are relatively invariant as film properties change during processing. For example, where the property is film thickness, as the thickness in an area changes as a result of CMP, the film stack model adjusts for the derived thickness when it solves for the layers. The result is a high GOF as long as the model is appropriate for the area being analyzed.

The previously generated map comprises a standard GOF map produced using the same system and methods used to generate the map that is under comparison. One or more standard GOF maps may be generated for each wafer pattern, such that each standard GOF map corresponds to a particular region of interest on the wafer surface. The pattern on a standard GOF map is learned using commercially available pattern recognition (e.g. edge and shape detection) software, such as PatMax, developed by Cognex Corp. of Natick, Mass. Once the software learns to recognize patterns of the previously generated map or maps, the system can compare subsequently fabricated wafers for GOF. For further information on pattern recognition, see "Contrast Variations Pose No Problem for Advanced Vision Systems," Cognex Corp., Jun. 17, 1999. Based on the comparison to a previously-generated GOF map, the method locates a region of interest having specified characteristics by means of the pattern recognition software. In one example, the region of interest is the location of a measurement pad. In another aspect, the wafer orientation is determined.

Figure 39:
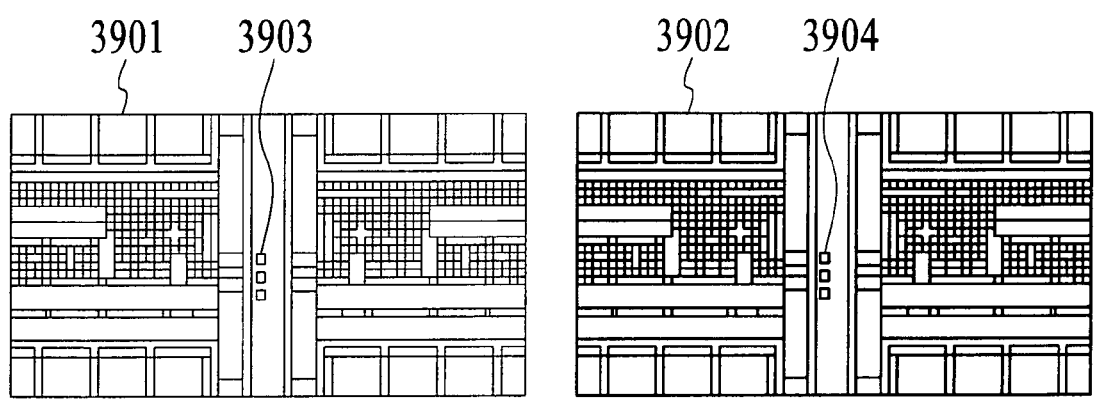
FIG. 39 shows visual images of different areas of the same wafer using prior art imaging methods.
Figure 40:
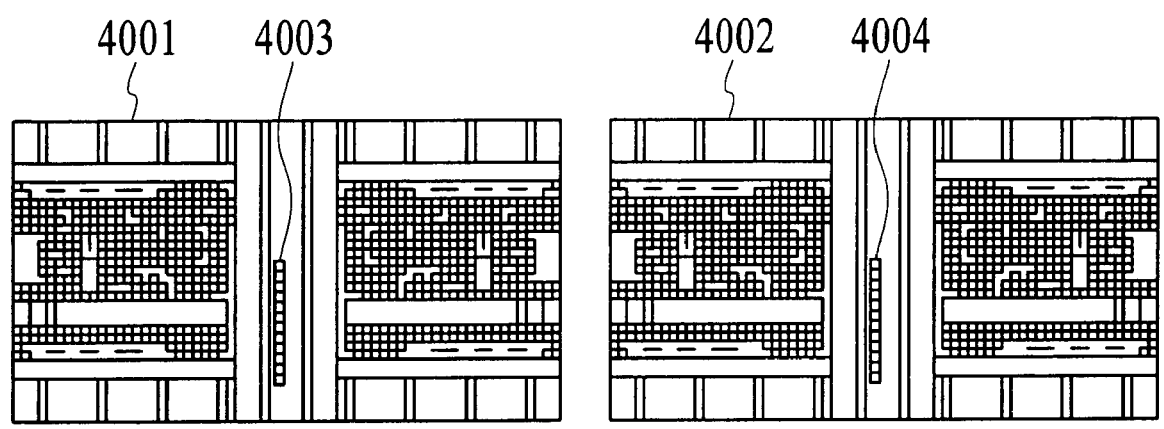
FIG. 40 shows GOF maps of the wafer areas of FIG. 39 using methods according to the present invention.
Figure 41:
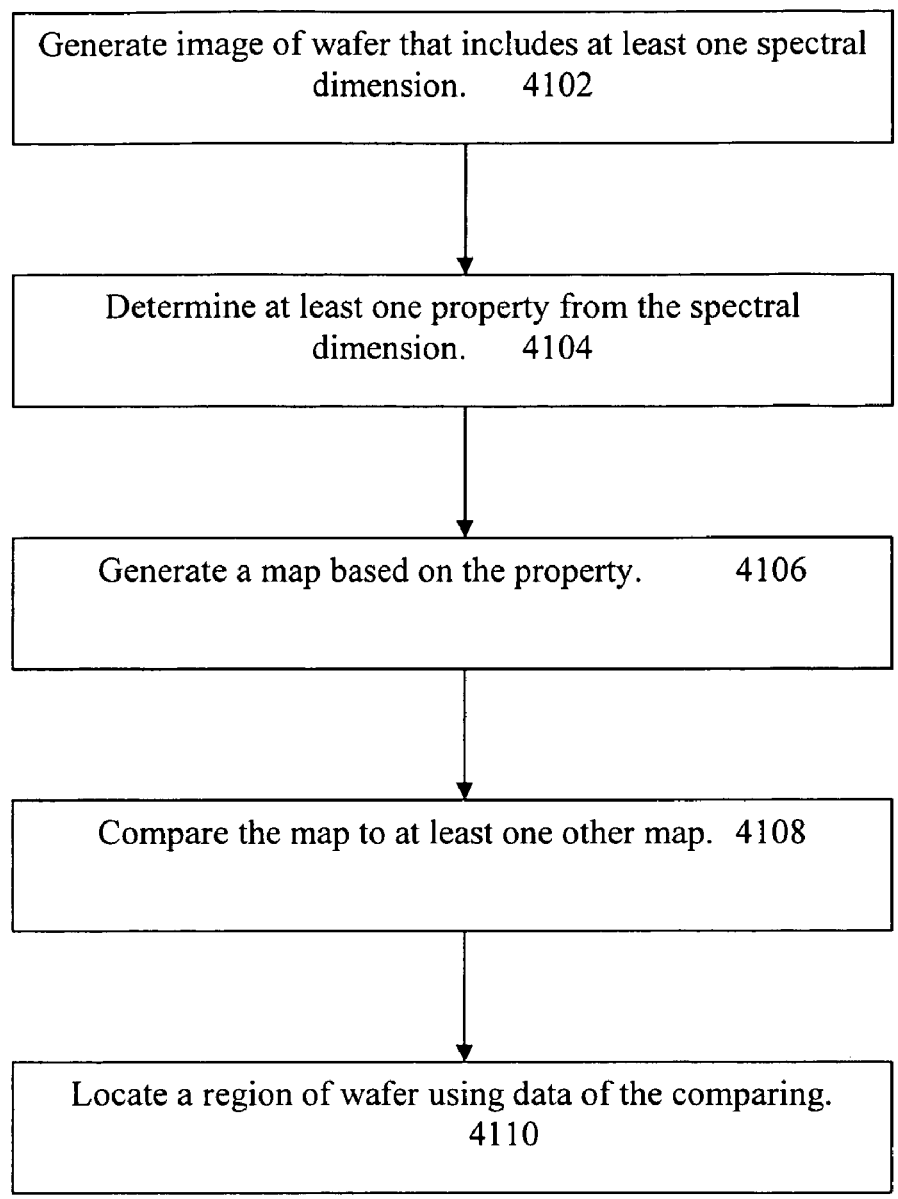
FIG. 41 is a flow diagram for determining wafer orientation from a spectral image, under an embodiment.

The advantage of this method can be better understood with reference to FIGS. 39 and 40. FIG. 39 shows visual images 3901 and 3902 of different areas of the same wafer using prior art imaging methods. Measurement pads 3903 and 3904 appear near the image centers, as indicated. In FIG. 39, images 3901 and 3902 contain similar patterns but have different film thicknesses. The difference in thickness causes a noticeable difference in contrast between image 3901 and 3902. In particular, the contrast difference between measuring pads 3903 and 3904 will lead to pattern recognition difficulty. FIG. 40 shows GOF maps of the wafer areas of FIG. 39 using methods according to the embodiments described herein. Note that in FIG. 40, the GOF map images 4001 and 4002 shown therein are virtually indistinguishable in spite of changes in the film stack thicknesses. Measurement pads 4003 and 4004 appear very similar, and can be easily recognized by pattern recognition software. FIG. 41 is a flow diagram for determining 4100 wafer orientation from a spectral image, under an embodiment.

The imaging of an embodiment includes a system for measuring one or more properties of a film. The system of an embodiment includes a light source for directing light to the film. The system of an embodiment includes a one-dimensional imaging spectrometer for receiving light reflected from a one dimensional pattern of spatial locations on the film, and determining therefrom a reflectance spectrum for one or more of the spatial locations in the pattern, the spectrometer configured to provide resolution of one millimeter or better along both first and second spatial dimensions. The system of an embodiment includes a translation mechanism for relatively translating the film with respect to the spectrometer. The system of an embodiment includes a processor for one or more of: obtaining from the spectrometer reflectance spectra for a plurality of one dimensional patterns of spatial locations along the film; aggregating these reflectance spectra to obtain reflectance spectra for a two dimensional area on the film, the reflectance spectra for the area having spatial resolution of one millimeter or better; and/or determining one or more properties of the film.

The translation mechanism of an embodiment is configured to move a platform supporting the film relative to the light source and spectrometer.

The translation mechanism of an embodiment is configured to move the light source and spectrometer relative to a platform supporting the film.

The processor of an embodiment is configured to determine the one or more properties of the layer at one or more desired measurement locations.

The processor of an embodiment is configured to locate the one or more desired measurement locations at least in part by analyzing at least a portion of the reflectance spectra for the two dimensional area.

The processor of an embodiment is configured to determine the one or more properties at a location by comparing a modeled reflectance spectrum with an actual reflectance spectrum at or within an area surrounding the location.

The processor of an embodiment is configured to vary one or more modeling assumptions or the location of the actual reflectance spectrum until the actual reflectance spectrum and modeled reflectance spectrum are within a predetermined tolerance.

The processor of an embodiment is configured to determine film thickness at the one or more desired measurement locations.

The processor of an embodiment is configured to determine an optical constant at the one or more desired measurement locations.

The processor of an embodiment is configured to determine doping density at the one or more desired measurement locations.

The processor of an embodiment is configured to determine a refractive index at the one or more desired measurement locations.

The processor of an embodiment is configured to determine an extinction coefficient at the one or more desired measurement locations.

The translation mechanism of an embodiment is integral with equipment for manufacturing semiconductor microelectronics.

The spectrometer of an embodiment is configured to determine reflectance spectra for a one dimensional pattern of spatial locations in the shape of a line. The line of an embodiment is linear. The line of an embodiment is non-linear.

The reflectance spectra of an embodiment for the two dimensional area is aggregated from the reflectance spectra of successive lines.

The spectrometer of an embodiment is configured to communicate reflectance spectra to the processor through a wireless interface.

The spectrometer of an embodiment is configured to communicate reflectance spectra to the processor through a wireline interface.

The spectrometer of an embodiment is configured to communicate reflectance spectra to the processor through one or more optical communications links.

The imaging of an embodiment includes a method for measuring one or more properties of a film. The method of an embodiment includes directing light to the film. The method of an embodiment includes receiving light reflected from a one dimensional pattern of spatial locations on the film, and determining from the light a reflectance spectrum for one or more of the one dimensional spatial locations in the pattern. The method of an embodiment includes obtaining reflectance spectra for additional one dimensional patterns of spatial locations on the film. The method of an embodiment includes aggregating these reflectance spectra to obtain reflectance spectra for a two dimensional area on the film, the reflectance spectra for the area having spatial resolution of one millimeter or better. The method of an embodiment includes determining one or more properties of the film.

The method of an embodiment includes determining the one or more properties of the film at one or more desired measurement locations.

The method of an embodiment includes locating the one or more desired measurement locations at least in part by analyzing at least a portion of the reflectance spectra for the two dimensional area.

The method of an embodiment includes determining the one or more properties at a location by comparing a modeled reflectance spectrum with an actual reflectance spectrum at or within an area surrounding the location.

The method of an embodiment includes varying one or more modeling assumptions or the location of the actual reflectance spectrum until the actual reflectance spectrum and modeled reflectance spectrum are within a predetermined tolerance.

The method of an embodiment includes determining film thickness at the one or more desired measurement locations.

The method of an embodiment includes determining an optical constant at the one or more desired measurement locations.

The method of an embodiment includes determining doping density at the one or more desired measurement locations.

The method of an embodiment includes determining a refractive index at the one or more desired measurement locations.

The method of an embodiment includes determining an extinction coefficient at the one or more desired measurement locations.

The method of an embodiment includes obtaining reflectance spectra for successive one dimensional patterns of contiguous spatial locations along the surface of the film in the shape of a line. The line of an embodiment includes is linear. The line of an embodiment includes is non-linear.

The method of an embodiment includes aggregating the reflectance spectra for successive lines to form the reflectance spectra for the two dimensional area.

The imaging of an embodiment includes a system for measuring one or more properties of a film. The system of an embodiment includes a light source for directing light to the film. The system of an embodiment includes a one-dimensional imaging spectrometer for receiving light reflected from a one dimensional pattern of spatial locations on the film, and determining from the light a reflectance spectrum for one or more of the spatial locations in the pattern, the spectrometer configured to receive light from an angle near normal to the film and to provide resolution of one millimeter or better along both first and second spatial dimensions. The system of an embodiment includes a translation mechanism for relatively translating the film with respect to the spectrometer. The system of an embodiment includes a processor for one or more of: obtaining from the spectrometer reflectance spectra for a plurality of one dimensional patterns of spatial locations along the film; aggregating these reflectance spectra to obtain reflectance spectra for a two dimensional area on the film, the reflectance spectra for the area having spatial resolution of one millimeter or better; and determining one or more properties of the film.

The imaging of an embodiment includes a system for measuring one or more properties of a film. The system of an embodiment includes a light source for directing light to the film. The system of an embodiment includes a first polarizer disposed between said light source and the film. The system of an embodiment includes a second polarizer disposed to transmit light reflected from the film. The system of an embodiment includes a one-dimensional imaging spectrometer for receiving light reflected from a one dimensional pattern of spatial locations on the film and transmitted through said second polarizer, and determining a reflectance spectrum for one or more of the spatial locations in the pattern, the spectrometer configured to receive light from a non-normal angle to the film and to provide resolution of one millimeter or better along both first and second spatial dimensions. The system of an embodiment includes a translation mechanism for relatively translating the film with respect to the spectrometer. The system of an embodiment includes a processor for one or more of: obtaining from the spectrometer reflectance spectra for a plurality of one dimensional patterns of spatial locations along the film; aggregating these reflectance spectra to obtain reflectance spectra for a two dimensional area on the film, the reflectance spectra for the area having spatial resolution of one millimeter or better; and determining one or more properties of the film.

The imaging of an embodiment includes a method for measuring erosion in an array of conductive lines in a transparent film. The method of an embodiment includes illuminating the array with polarized light. The method of an embodiment includes detecting light reflected from a plurality of locations within and around the array by means of a line imaging spectrometer, said line imaging spectrometer configured to record polarized light. The method of an embodiment includes recording reflectance data from the plurality of locations within the array. The method of an embodiment includes determining from the reflectance data a first location from a substantially un-eroded region near the array. The method of an embodiment includes calculating a first thickness value of the transparent film at the first location. The method of an embodiment includes calculating from the reflectance data a set of thickness values of the transparent film. The method of an embodiment includes determining from the set of thickness values a minimum thickness value. The method of an embodiment includes calculating an erosion value from the difference between the first thickness value and the minimum thickness value.

The imaging of an embodiment includes a method for correcting for second order diffraction errors. The method of an embodiment includes providing a diffraction grating structured to diffract first and second order light. The method of an embodiment includes providing a detector disposed to receive the first and second order light, said detector having a minimum wavelength sensitivity and a cutoff wavelength. The method of an embodiment includes illuminating said diffraction grating with a narrow spectral source, the spectral source having a spectral source wavelength between the minimum wavelength and one-half of the cutoff wavelength. The method of an embodiment includes recording a first order reflectance intensity at the spectral source wavelength and a second order reflectance intensity at twice the spectral source wavelength. The method of an embodiment includes calculating a ratio of said first order reflectance intensity to said second order reflectance intensity. The method of an embodiment includes repeating illuminating said diffraction grating with a narrow spectral source, recording a first order reflectance intensity at the spectral source wavelength and a second order reflectance intensity at twice the spectral source wavelength, and calculating a ratio of said first order reflectance intensity to said second order reflectance intensity at a plurality of spectral source wavelengths, each spectral source wavelength having a value between the minimum wavelength and one-half of the cutoff wavelength, thereby obtaining a plurality of ratios. The method of an embodiment includes calculating a wavelength dependent correction factor from said ratios for wavelengths ranging from twice the minimum wavelength to the cutoff wavelength.

The imaging of an embodiment includes a method for compensating for non-constant wafer velocity while acquiring an image of a patterned wafer. The method of an embodiment includes providing an image of the patterned wafer, said wafer having straight vertical streets and straight horizontal streets. The method of an embodiment includes identifying a first edge of said wafer image. The method of an embodiment includes identifying a first tangent at said first edge. The method of an embodiment includes identifying a second edge of said wafer image, said second edge lying along a column of reflectance points from said first edge. The method of an embodiment includes identifying a second tangent at said second edge. The method of an embodiment includes calculating a correction factor for all locations in said column. The method of an embodiment includes repeating the identifying described above for all columns in said wafer image.

The imaging of an embodiment includes a method for finding a center point of a patterned semiconductor wafer. The method of an embodiment includes providing an image of the patterned wafer, the image comprising a plurality of pixels of reflectance measurements, and having top, bottom, first side, and second side edge image locations. The method of an embodiment includes estimating a center point of the patterned wafer image from the edge image locations. The method of an embodiment includes calculating a succession of horizontal chord lengths, each length extending across the wafer image, the series beginning at a distance several pixels above the estimated center point and ending at a distance several pixels below the estimated center point. The method of an embodiment includes identifying a maximum horizontal chord length from the succession of horizontal chord lengths. The method of an embodiment includes calculating a succession of vertical chord lengths, each length extending across the wafer image, the series beginning at a distance several pixels from a first side of the estimated center point and ending at a distance several pixels from a second side of the estimated center point opposite the first side. The method of an embodiment includes identifying a maximum vertical chord length from the succession of vertical chord lengths. The method of an embodiment includes locating the center point at an intersection of the maximum horizontal chord length and the maximum vertical chord length.

The imaging of an embodiment includes a method for finding a notch in an image of a wafer. The method of an embodiment includes providing an image of the patterned wafer, the image having a center point, the image further comprising a plurality of columns, each column having a first end and a second end and comprising a plurality of reflectance measurements. The method of an embodiment includes for each column: comparing the plurality of reflectance measurements in a column to a reflectance measurement at the first end of the column to determine a first edge; comparing the plurality of reflectance measurements in the column to a reflectance measurement at the second end of the column to determine a second edge; calculating a first radial distance from the center point to the first edge; storing the first radial distance; calculating a second radial distance from the center point to the second edge; storing the second radial distance; and repeating these steps for each column of reflectance measurements.

The imaging of an embodiment includes a method for aligning an image of a patterned wafer. The method of an embodiment includes providing an image of the patterned wafer, said image comprising a plurality of rows of reflectance measurements, each row having a first end and a second end. The method of an embodiment includes identifying an initial orientation angle. The method of an embodiment includes determining a single "Goodness-of-Alignment" value for a given orientation of said image by one or more of: summing all of the reflectance measurements along each row to form a sequence of row sums;

forming a difference row by calculating a difference between adjacent elements of the sequence of row sums; determining said Goodness-of-Alignment value for the given orientation of said image by summing each value in the difference row that exceeds a threshold value; determining a rotation angle; rotating said image by an incremental angle; repeating the determining of Goodness-of-Alignment and summing all reflectance measurements described above as appropriate until said rotation angle exceeds a maximum rotation angle; identifying a maximum "Goodness-of-Alignment" value and an optimal rotation angle corresponding to the maximum "Goodness of Alignment" value; and rotating said wafer image from the initial orientation angle to the optimal rotation angle.

The imaging of an embodiment includes an apparatus for reducing measurement size. The apparatus of an embodiment includes a linear array of pixels disposed to receive light from approximately normal incidence, each pixel in the array having a central region, a left region, a right region, a top region, and a bottom region. The apparatus of an embodiment includes a mask that blocks light from reaching portions of said pixels in said right region and in said left region. The apparatus of an embodiment includes a slit having a first edge and a second edge, said slit disposed so that said first edge and said second edge are parallel and aligned with said linear array of pixels, where said first edge blocks light from reaching the top region of each pixel and where said second edge blocks light from reaching the bottom region of each pixel.

The imaging of an embodiment includes a sensor array for increased horizontal measurement density, comprising an array of pixels arranged in a plurality of groups of N rows, wherein each pixel in each row has a pixel width and a mask having a mask width, said mask width being less than said pixel width and said mask obscuring a portion of each pixel in the array, and wherein each row of each group is offset by said pixel width divided by N.

The imaging of an embodiment includes an apparatus for restricting wafer motion to one dimension. The apparatus of an embodiment includes a wand for securing the wafer. The apparatus of an embodiment includes an arm mechanically attached to said wand for moving the wafer, said arm having a cross sectional profile and a component for reducing friction. The apparatus of an embodiment includes a translation mechanism mechanically linked to said arm. The apparatus of an embodiment includes a fixture having a groove, the groove extending in the dimension of desired motion and dimensionally configured to mate with the cross sectional profile of the arm, the fixture further comprising a component for reducing friction.

The imaging of an embodiment includes a line imaging spectrometer for imaging a wafer in a chamber. The spectrometer of an embodiment includes a viewport embedded in the chamber that provides optical access to the wafer, said viewport having optical properties. The spectrometer of an embodiment includes an optical axis disposed at an angle away from perpendicular to the wafer and passing through said viewport. The spectrometer of an embodiment includes a first lens assembly disposed along said optical axis to receive light from said viewport, said first lens assembly having optical parameters that depend on said viewport. The spectrometer of an embodiment includes a slit having a slit width and disposed along said optical axis to receive light from said first lens assembly, said slit width restricting light passing through it to a narrow portion of the wafer. The spectrometer of an embodiment includes a second lens assembly disposed along said optical axis to receive light from said slit, said second lens assembly having optical parameters that depend on said viewport. The spectrometer of an embodiment includes a diffraction grating disposed along said optical axis, said grating disposed to receive light from said second lens and to diffract the light in a direction perpendicular to said slit and said optical axis. The spectrometer of an embodiment includes a two-dimensional imager disposed along said optical axis to receive light from said diffraction grating.

The imaging of an embodiment includes an apparatus for producing a line image of a portion of a patterned substrate. The apparatus of an embodiment includes a first Offner group having a first focal point and a second focal point, where said first focal point coincides with said portion of said patterned substrate. The apparatus of an embodiment includes a folding mirror disposed between said second focal point and said first Offner group. The apparatus of an embodiment includes a second Offner group having a third focal point and a fourth focal point, wherein said third focal point coincides with said second focal point. The apparatus of an embodiment includes a slit having two straight edges arranged with a distance between, wherein said slit is disposed in a plane perpendicular to the direction of propagation of light at said second and said third focal points. The apparatus of an embodiment includes a one-dimensional imaging system having an entrance aperture disposed at said fourth focal point.

The imaging of an embodiment includes a system for measuring one or more properties of a film. The system of an embodiment includes a light source for directing light to the film. The system of an embodiment includes a one-dimensional imaging spectrometer for receiving light reflected from a one dimensional pattern of spatial locations on the film and where the one dimensional pattern has an orientation, and determining a reflectance spectrum for one or more of the spatial locations in the pattern, the spectrometer configured to provide resolution of one millimeter or better along both first and second spatial dimensions. The system of an embodiment includes a translation mechanism for relatively translating the film with respect to the spectrometer, where the translation is at an angle non-perpendicular relative to the orientation of the one dimensional pattern. The system of an embodiment includes a processor for one or more of (a) obtaining from the spectrometer reflectance spectra for a plurality of one dimensional patterns of spatial locations along the film; (b) aggregating these reflectance spectra to obtain reflectance spectra for a two dimensional area on the film; and (c) determining one or more properties of the film.

The imaging of an embodiment includes a method for measuring one or more properties of a film. The method of an embodiment includes directing light to the film. The method of an embodiment includes receiving light reflected from a one dimensional pattern of spatial locations on the film, where the one dimensional pattern has an orientation, and determining therefrom a reflectance spectrum for one or more of the one dimensional spatial locations in the pattern. The method of an embodiment includes obtaining reflectance spectra for additional one dimensional patterns of spatial locations on the film along a direction non-perpendicular to the orientation of the one dimensional pattern. The method of an embodiment includes aggregating these reflectance spectra to obtain reflectance spectra for a two dimensional area on the film, the reflectance spectra for the area having spatial resolution of one millimeter or better. The method of an embodiment includes determining one or more properties of the film.

The imaging of an embodiment includes an apparatus for producing a line image of a portion of a patterned substrate. The apparatus of an embodiment includes a retro-reflecting assembly that includes a first mirror, a slit having two straight edges arranged with a distance between said straight edges, and a second mirror, said first mirror disposed to direct incident light through said slit to said second mirror. The apparatus of an embodiment includes an Offner group having a first focal point, a second focal point, a first aperture and a second aperture, where said first focal point coincides with the portion of the patterned substrate, said second focal point coincides with said slit, said first aperture receives light from the patterned substrate and said second aperture receiving light from said second mirror. The apparatus of an embodiment includes a reflector for deflecting a portion of light reflected from said second aperture. The apparatus of an embodiment includes an imaging system having an entrance aperture disposed to receive light deflected by said reflector.

The imaging of an embodiment includes an auto-focusing, one-dimensional spectral imaging system for imaging a substrate. The system of an embodiment includes a one-dimensional spectral imaging system having a line imaging spectrometer and a distance sensor disposed within said one-dimensional spectral imaging system, wherein said distance sensor provides a measurement of a distance between said line imaging spectrometer and the substrate. The system of an embodiment includes an adjustor for adjusting said distance to a pre-determined distance.

The imaging of an embodiment includes a method of using an auto-focusing, one-dimensional spectral imaging system for imaging a portion of a substrate. The imaging of an embodiment includes positioning the substrate at a pre-determined height. The imaging of an embodiment includes acquiring spectral image data while ensuring the wafer remains at the pre-determined height. The imaging of an embodiment includes repeating the positioning and acquiring until spectral image data for all of the portion of the substrate has been acquired.

The imaging of an embodiment includes an auto-focusing, one-dimensional spectral imaging system for imaging a substrate. The system of an embodiment includes a one-dimensional spectral imaging system having a line imaging spectrometer with a focal length that is adjustable from a nominal focal length. The system of an embodiment includes a distance sensor disposed within said one-dimensional spectral imaging system at a reference distance away from the substrate, where said distance sensor provides a measurement of a distance between said line imaging spectrometer and the substrate. The system of an embodiment includes an adjustor for adjusting said nominal focal length by an amount equal to a difference between said measurement and said reference distance.

The imaging of an embodiment includes a method for acquiring spectral images of a portion of a substrate. The method of an embodiment includes providing an auto-focusing, one-dimensional spectral imaging system having a line imaging spectrometer with an adjustable focal length. The method of an embodiment includes positioning the substrate at a pre-determined distance from the line imaging spectrometer so that said line imaging spectrometer images a part of the portion. The method of an embodiment includes using a distance sensor to determine a deviation of the substrate from the pre-determined distance. The method of an embodiment includes adjusting the focal length by an amount equal to said deviation. The method of an embodiment includes acquiring spectral image data of the wafer. The method of an embodiment includes repeating the process described herein until spectral image data for all of the portion of the substrate has been acquired.

The imaging of an embodiment includes a system for processing a substrate having a film layer. The system of an embodiment includes a semiconductor processing tool that performs a process step, wherein said tool includes a one-dimensional spectral imaging system disposed within the tool, where said one-dimensional spectral imaging system has a line imaging spectrometer and a distance sensor disposed within said one-dimensional spectral imaging system, wherein said distance sensor provides a measurement of a distance between said line imaging spectrometer and the substrate to said one-dimensional spectral imaging system. The system of an embodiment includes an adjustor for adjusting said distance to a pre-determined distance to obtain a spectral image of the substrate. The system of an embodiment includes a component for calculating from said spectral image a film layer property. The spectral image of an embodiment is obtained in situ or in-line.

The imaging of an embodiment includes a method for locating a region of a wafer. The method of an embodiment includes generating an image of a wafer that includes at least one spectral dimension. The method of an embodiment includes determining at least one property from the spectral dimension. The method of an embodiment includes generating a map based on the property. The method of an embodiment includes comparing the map to at least one other map. The method of an embodiment includes locating a region of the wafer using data of the comparing.

The property of an embodiment includes a film stack property of a film of the wafer.

The property of an embodiment is film thickness of a film of the wafer.

The map of an embodiment is a goodness-of-fit (GOF) map of the spectral dimension.

The map of an embodiment is a two-dimensional map.

The map of an embodiment corresponds to a portion of a surface of the wafer.

The other map of an embodiment is a goodness-of-fit map.

The comparing of an embodiment comprises comparing the map to goodness-of-fit (GOF) criteria.

The image of an embodiment is a two-dimensional image.

The image of an embodiment includes an image of a portion of a surface of the wafer.

The method of an embodiment further comprises generating the other map by generating a model of reflectance spectra of the wafer as a film stack.

The comparing of an embodiment includes pattern recognition.

The region of an embodiment includes a structure of the wafer. The structure of the wafer can include a measurement pad for example.

The method of an embodiment further comprises determining wafer orientation using data of the comparing.

The wafer of an embodiment includes at least one thin film on a substrate.

The imaging of an embodiment includes a system comprising an imaging spectrometer configured to determine a reflectance spectrum for one or more spatial locations of a film of the wafer using reflected light of the wafer. The system of an embodiment includes an imager configured to generate an image of an area of the film, the image including a spectral dimension. The system of an embodiment includes a processor configured to determine from the image at least one property of the film and generate a map based on the property, and locate a pre-specified region of the wafer using data of a comparison between the map and a goodness-of-fit map.

The reflected light of an embodiment is reflected from a one-dimensional pattern of spatial locations on the film.

The imager of an embodiment is further configured to generate reflectance spectra for a plurality of one-dimensional patterns of the spatial locations along the film using the reflectance spectrum for each spatial location. The imager of an embodiment is further configured to aggregate the reflectance spectra to generate another reflectance spectra for a two-dimensional area on the film.

The system of an embodiment further comprises a translation mechanism for translating the film relative to the spectrometer.

The comparison of an embodiment includes pattern recognition.

The pre-specified region of an embodiment includes a measurement pad.

The processor of an embodiment is configured to determine orientation of the wafer using data of the comparison.

The property of an embodiment includes a film stack property of a film of the wafer.

The property of an embodiment is film thickness of a film of the wafer.

The map of an embodiment is a goodness-of-fit (GOF) map of the spectral dimension.

The map of an embodiment is a two-dimensional map.

The image of an embodiment is a two-dimensional image.

The wafer of an embodiment includes at least one thin film on a substrate.

The imaging of an embodiment includes machine readable media including executable instructions that when executed in a processing system generate an image of a wafer that includes at least one spectral dimension. The instructions of an embodiment when executed determine at least one property from the spectral dimension. The instructions of an embodiment when executed generate a map based on the property. The instructions of an embodiment when executed compare the map to at least one other map. The instructions of an embodiment when executed locate a region of the wafer using data of the comparing.

The property of an embodiment includes a film stack property of a film of the wafer.

The map of an embodiment is a goodness-of-fit (GOF) map of the spectral dimension.

The map of an embodiment corresponds to a portion of a surface of the wafer.

Comparing the map to at least one other map of an embodiment comprises comparing the map to goodness-of-fit (GOF) criteria.

The image of an embodiment includes an image of a portion of a surface of the wafer.

Comparing the map to at least one other map of an embodiment comprises pattern recognition.

The region of an embodiment includes a structure of the wafer.

Execution of the executable instructions of an embodiment in a processing system determines wafer orientation using data of the comparing.

Aspects of the imaging described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the imaging include: microcontrollers with memory (such as electronically erasable programmable read only memory (EEPROM)), embedded microprocessors, firmware, software, etc. Furthermore, aspects of the imaging may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that the various components disclosed herein may be described and expressed (or represented) as data and/or instructions embodied in various computer-readable media. Computer-readable media in which such data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the imaging is not intended to be exhaustive or to limit the imaging to the precise form disclosed. While specific embodiments of, and examples for, the imaging are described herein for illustrative purposes, various equivalent modifications are possible within the scope of the imaging, as those skilled in the relevant art will recognize. The teachings of the imaging provided herein can be applied to other processing systems and methods, not only for the systems and methods described above.

The elements and acts of the various embodiments described above can be combined to provide further embodiments. These and other changes can be made to the imaging in light of the above detailed description.

In general, in the following claims, the terms used should not be construed to limit the imaging to the specific embodiments disclosed in the specification and the claims, but should be construed to include all processing systems that operate under the claims. Accordingly, the imaging is not limited by the disclosure, but instead the scope of the imaging is to be determined entirely by the claims.

While certain aspects of the imaging are presented below in certain claim forms, the inventors contemplate the various aspects of the imaging in any number of claim forms. For example, while only one aspect of the imaging is recited as embodied in machine-readable medium, other aspects may likewise be embodied in machine-readable medium. Accordingly, the inventors reserve the right to add additional claims after filing the application to pursue such additional claim forms for other aspects of the imaging.

What is claimed is:

1. A method comprising:
generating an image of a wafer that includes at least one spectral dimension;
determining at least one property from the spectral dimension;
generating a map based on the property;
comparing the map to at least one other map; and
locating a region of the wafer using data of the comparing.

2. The method of claim 1, wherein the property includes a film stack property of a film of the wafer.

3. The method of claim 1, wherein the property is film thickness of a film of the wafer.

4. The method of claim 1, wherein the map is a goodness-of-fit (GOF) map of the spectral dimension.

5. The method of claim 1, wherein the map is a two-dimensional map.

6. The method of claim 1, wherein the map corresponds to a portion of a surface of the wafer.

7. The method of claim 1, wherein the other map is a goodness-of-fit map.

8. The method of claim 1, wherein the comparing comprises comparing the map to goodness-of-fit (GOF) criteria.

9. The method of claim 1, wherein the image is a two-dimensional image.

10. The method of claim 1, wherein the image includes an image of a portion of a surface of the wafer.

11. The method of claim 1, further comprising generating the other map by generating a model of reflectance spectra of the wafer as a film stack.

12. The method of claim 1, wherein the comparing includes pattern recognition.

13. The method of claim 1, wherein the region includes a measurement pad.

14. The method of claim 1, further comprising determining wafer orientation using data of the comparing.

15. The method of claim 1, wherein the wafer includes at least one thin film on a substrate.

16. A system comprising:
an imaging spectrometer configured to determine a reflectance spectrum for one or more spatial locations of a film of the wafer using reflected light of the wafer;
an imager configured to generate an image of an area of the film, the image including a spectral dimension; and
a processor configured to determine from the image at least one property of the film and generate a map based on the property, and locate a pre-specified region of the wafer using data of a comparison between the map and a goodness-of-fit map.

17. The system of claim 16, wherein the reflected light is reflected from a one-dimensional pattern of spatial locations on the film.

18. The system of claim 17, wherein the imager is further configured to:
generate reflectance spectra for a plurality of one-dimensional patterns of the spatial locations along the film using the reflectance spectrum for each spatial location;
aggregate the reflectance spectra to generate another reflectance spectra for a two-dimensional area on the film.

19. The system of claim 16, further comprising a translation mechanism for translating the film relative to the spectrometer.

20. The system of claim 16, wherein the comparison includes pattern recognition.

21. The system of claim 16, wherein the pre-specified region includes a measurement pad.

22. The system of claim 16, wherein the processor is configured to determine orientation of the wafer using data of the comparison.

23. The system of claim 16, wherein the property includes a film stack property of a film of the wafer.

24. The system of claim 16, wherein the property is film thickness of a film of the wafer.

25. The system of claim 16, wherein the map is a goodness-of-fit (GOF) map of the spectral dimension.

26. The system of claim 16, wherein the map is a two-dimensional map.

27. The system of claim 16, wherein the image is a two-dimensional image.

28. The system of claim 16, wherein the wafer includes at least one thin film on a substrate.

29. Machine readable media including executable instructions that when executed in a processing system:
generate an image of a wafer that includes at least one spectral dimension;
determine at least one property from the spectral dimension;
generate a map based on the property;
compare the map to at least one other map; and
locate a region of the wafer using data of the comparing.

30. The machine readable media of claim 29, wherein the property includes a film stack property of a film of the wafer.

31. The machine readable media of claim 29, wherein the map is a goodness-of-fit (GOF) map of the spectral dimension.

32. The machine readable media of claim 29, wherein the map corresponds to a portion of a surface of the wafer.

33. The machine readable media of claim 29, wherein comparing the map to at least one other map comprises comparing the map to goodness-of-fit (GOF) criteria.

34. The machine readable media of claim 29, wherein the image includes an image of a portion of a surface of the wafer.

35. The machine readable media of claim 29, wherein the comparing the map to at least one other map comprises pattern recognition.

36. The machine readable media of claim 29, wherein the region includes a structure of the wafer.

37. The machine readable media of claim 29, wherein execution of the executable instructions in a processing system determines wafer orientation using data of the comparing.

* * * * *